United States Patent
Samsoondar

(10) Patent No.: US 8,206,650 B2
(45) Date of Patent: *Jun. 26, 2012

(54) JOINT-DIAGNOSTIC SPECTROSCOPIC AND BIOSENSOR METER

(75) Inventor: James Samsoondar, Markham (CA)

(73) Assignee: Chromedx Inc., Markham (CA)

( * ) Notice: Subject to any disclaimer, the term of this patent is extended or adjusted under 35 U.S.C. 154(b) by 284 days.

This patent is subject to a terminal disclaimer.

(21) Appl. No.: 11/415,284

(22) Filed: May 2, 2006

(65) Prior Publication Data

US 2006/0228259 A1  Oct. 12, 2006

Related U.S. Application Data

(63) Continuation-in-part of application No. 11/103,619, filed on Apr. 12, 2005, and a continuation-in-part of application No. 11/108,912, filed on Apr. 19, 2005.

(30) Foreign Application Priority Data

| May 13, 2005 | (CA) | ....... 2507323 |
| Aug. 26, 2005 | (CA) | ....... 2517299 |
| Oct. 7, 2005 | (CA) | ....... 2523486 |

(51) Int. Cl.
*G01N 21/00* (2006.01)

(52) U.S. Cl. ........ 422/82.05; 422/82.01; 422/119; 422/404; 422/503; 422/552; 422/554; 435/287.3; 436/66; 436/68; 600/300; 600/368; 600/324; 600/326

(58) Field of Classification Search ............... None
See application file for complete search history.

(56) References Cited

U.S. PATENT DOCUMENTS

| 3,874,850 | A | | 4/1975 | Sorenson et al. |
| 4,013,417 | A | * | 3/1977 | Raffaele ............... 422/67 |
| 4,040,421 | A | | 8/1977 | Young |
| 4,046,145 | A | | 9/1977 | Choksi et al. |
| 4,088,448 | A | | 5/1978 | Lilja et al. |
| 4,409,106 | A | | 10/1983 | Furuta et al. |
| 4,613,422 | A | | 9/1986 | Lauks |
| 4,668,399 | A | | 5/1987 | Duggins |
| 4,695,274 | A | | 9/1987 | Fox |

(Continued)

FOREIGN PATENT DOCUMENTS

CA   2281909 C   9/1998

(Continued)

OTHER PUBLICATIONS

K.A. Erickson and P. Wilding, Clinical Chemistry 39(2): 283-287, 1993.*

(Continued)

*Primary Examiner* — In Suk Bullock
*Assistant Examiner* — Timothy G Kingan

(57) ABSTRACT

Some embodiments of the invention provide a system comprising a meter and a disposable cartridge for analyzing a fluid sample typically blood that is drawn into the cartridge by capillary action, negative pressure, positive pressure, or a combination thereof. The cartridge has at least one flow path, and includes at least one optical chamber for spectroscopic measurement, and at least one biosensor for biosensor measurement. The meter has a sample slot for receiving the disposable cartridge. The cartridges have electrical output contacts, and the meter slot has electrical input contacts. When the output contacts mate with the input contacts, the optical chamber becomes positioned for spectroscopic measurement. The present invention can provide joint-diagnostic spectroscopic and biosensor measurements.

14 Claims, 23 Drawing Sheets

U.S. PATENT DOCUMENTS

| | | | |
|---|---|---|---|
| 4,743,233 A | 5/1988 | Schneider | |
| 4,756,884 A | 7/1988 | Hillman et al. | |
| 4,849,340 A | 7/1989 | Oberhardt | |
| 4,900,310 A | 2/1990 | Ogle, II | |
| 5,096,669 A * | 3/1992 | Lauks et al. | 204/403.02 |
| 5,112,455 A * | 5/1992 | Cozzette et al. | 205/778 |
| 5,361,758 A | 11/1994 | Hall et al. | |
| 5,430,542 A * | 7/1995 | Shepherd | 356/246 |
| 5,456,255 A | 10/1995 | Abe et al. | |
| 5,507,288 A | 4/1996 | Boecker et al. | |
| 5,553,616 A | 9/1996 | Ham et al. | |
| 5,638,828 A | 6/1997 | Lauks et al. | |
| 5,690,893 A * | 11/1997 | Ozawa et al. | 422/67 |
| 5,725,574 A | 3/1998 | Nguyen | |
| 5,725,774 A | 3/1998 | Neyer | |
| 5,772,586 A | 6/1998 | Heinonen et al. | |
| 5,840,020 A | 11/1998 | Heinonen et al. | |
| 5,891,024 A | 4/1999 | Jarman et al. | |
| 5,957,579 A | 9/1999 | Kopf-Sill et al. | |
| 5,976,433 A | 11/1999 | Komatsu et al. | |
| 6,066,243 A * | 5/2000 | Anderson et al. | 422/82.01 |
| 6,130,098 A * | 10/2000 | Handique et al. | 436/180 |
| 6,143,247 A | 11/2000 | Sheppard et al. | |
| 6,155,991 A | 12/2000 | Beat et al. | |
| 6,262,798 B1 | 7/2001 | Shepherd et al. | |
| 6,319,469 B1 * | 11/2001 | Mian et al. | 422/64 |
| 6,348,156 B1 | 2/2002 | Vishnoi et al. | |
| 6,393,310 B1 | 5/2002 | Kuenstner | |
| 6,484,046 B1 | 11/2002 | Say et al. | |
| 6,581,441 B1 | 6/2003 | Paul | |
| 6,695,147 B1 | 2/2004 | Yager et al. | |
| 6,787,368 B1 * | 9/2004 | Wong et al. | 436/518 |
| 6,822,097 B1 * | 11/2004 | Norman et al. | 546/153 |
| 6,878,271 B2 | 4/2005 | Gilbert | |
| 6,962,823 B2 | 11/2005 | Empedocies et al. | |
| 6,966,880 B2 | 11/2005 | Boecker et al. | |
| 7,018,838 B2 | 3/2006 | Murphy et al. | |
| 7,027,848 B2 | 4/2006 | Robinson et al. | |
| 7,094,345 B2 | 8/2006 | Gilbert et al. | |
| 7,258,774 B2 | 8/2007 | Chou et al. | |
| 7,314,718 B1 | 1/2008 | Dasgupta et al. | |
| 7,682,833 B2 | 3/2010 | Miller et al. | |
| 2002/0020206 A1 | 2/2002 | Mason et al. | |
| 2002/0025576 A1 | 2/2002 | Northrup et al. | |
| 2002/0042125 A1 * | 4/2002 | Petersen et al. | 435/287.2 |
| 2002/0045272 A1 * | 4/2002 | McDevitt et al. | 436/518 |
| 2002/0091057 A1 | 7/2002 | Westberg et al. | |
| 2002/0099281 A1 * | 7/2002 | Bahr et al. | 600/323 |
| 2002/0100714 A1 | 8/2002 | Staats | |
| 2002/0106786 A1 | 8/2002 | Carvalho et al. | |
| 2002/0142471 A1 * | 10/2002 | Handique et al. | 436/53 |
| 2002/0143437 A1 * | 10/2002 | Handique et al. | 700/266 |
| 2002/0164824 A1 | 11/2002 | Xiao et al. | |
| 2002/0177135 A1 | 11/2002 | Doung et al. | |
| 2002/0187072 A1 * | 12/2002 | Karp | 422/60 |
| 2002/0187074 A1 * | 12/2002 | O'Connor et al. | 422/82.05 |
| 2002/0193671 A1 | 12/2002 | Ciurczak et al. | |
| 2002/0197167 A1 * | 12/2002 | Kornelsen | 417/53 |
| 2003/0049862 A1 | 3/2003 | He et al. | |
| 2003/0073089 A1 * | 4/2003 | Mauze et al. | 435/6 |
| 2003/0123047 A1 | 7/2003 | Petterssen et al. | |
| 2003/0175990 A1 * | 9/2003 | Hayenga et al. | 436/180 |
| 2003/0209451 A1 | 11/2003 | Dineen et al. | |
| 2003/0215855 A1 * | 11/2003 | Dubrow et al. | 435/6 |
| 2004/0019431 A1 | 1/2004 | Sterling et al. | |
| 2004/0089616 A1 | 5/2004 | Kellogg et al. | |
| 2004/0176704 A1 | 9/2004 | Stevens et al. | |
| 2004/0176705 A1 * | 9/2004 | Stevens et al. | 600/584 |
| 2004/0189311 A1 * | 9/2004 | Glezer et al. | 324/444 |
| 2004/0224362 A1 | 11/2004 | Gjerde et al. | |
| 2004/0254419 A1 | 12/2004 | Wang et al. | |
| 2005/0026273 A1 * | 2/2005 | Zarur et al. | 435/286.1 |
| 2005/0054078 A1 * | 3/2005 | Miller et al. | 435/287.1 |
| 2005/0067277 A1 * | 3/2005 | Pierce et al. | 204/403.01 |
| 2005/0070771 A1 | 3/2005 | Rule et al. | |
| 2005/0130226 A1 | 6/2005 | Ahn et al. | |
| 2005/0130292 A1 | 6/2005 | Ahn et al. | |
| 2005/0152808 A1 * | 7/2005 | Ganesan | 422/99 |
| 2005/0153434 A1 * | 7/2005 | Andersson et al. | 435/287.2 |
| 2005/0175505 A1 * | 8/2005 | Cantor et al. | 422/68.1 |
| 2005/0203356 A1 | 9/2005 | Samsoondar | |
| 2005/0233352 A1 | 10/2005 | Zoval | |
| 2005/0252773 A1 * | 11/2005 | McBride et al. | 204/450 |
| 2006/0228258 A1 | 10/2006 | Samsoondar | |
| 2006/0233667 A1 | 10/2006 | Samsoondar | |
| 2006/0254962 A1 | 11/2006 | Samsoondar | |
| 2006/0257941 A1 * | 11/2006 | McDevitt et al. | 435/7.2 |
| 2006/0276724 A1 | 12/2006 | Freeman et al. | |
| 2007/0052956 A1 | 3/2007 | Blair | |
| 2007/0150223 A1 * | 6/2007 | Abraham-Fuchs et al. | 702/108 |
| 2007/0232995 A1 | 10/2007 | Samsoondar | |
| 2007/0284298 A1 | 12/2007 | Samsoondar | |
| 2008/0006009 A1 | 1/2008 | Kiern et al. | |
| 2008/0097243 A1 | 4/2008 | Samsoondar | |
| 2008/0180658 A1 | 7/2008 | Samsoondar | |
| 2010/0245803 A1 | 9/2010 | Samsoondar | |

FOREIGN PATENT DOCUMENTS

| | | | |
|---|---|---|---|
| CA | 2460898 A1 | | 9/2005 |
| CA | 2523486 A1 | | 10/2006 |
| CA | 2507323 A1 | | 11/2006 |
| CA | 2517299 A1 | | 2/2007 |
| JP | 60-011166 | * | 1/1985 |
| JP | 11076241 A | | 3/1999 |
| WO | 9412095 A3 | | 8/1994 |
| WO | 03022442 A8 | | 10/2003 |
| WO | 2005084527 A1 | | 9/2005 |
| WO | 2005081165 A3 | | 12/2005 |

OTHER PUBLICATIONS

Waters Medical Systems, "OXIMETRY" http://www.watersmed.com/oximetry.html dated Sep. 30, 2004.

Office Action issued in connection with co-pending U.S. Appl. No. 11/108,912, filed Apr. 19, 2005, mailed on Jul. 10, 2008.

Office Action issued in connection with co-pending U.S. Appl. No. 11/103,619, filed Apr. 12, 2005, mailed on Jun. 25, 2008.

Co-pending U.S. Appl. No. 11/432,616, "Diagnostic Whole Blood and Plasma Apparatus", May 12, 2006.

Co-pending U.S. Appl. No. 11/466,588, "Hollow Needle Assembly", filed Aug. 23, 2006.

Co-pending U.S. Appl. No. 11/738,889, "Hollow Needle Assembly" (CIP), filed Apr. 23, 2007.

Co-pending U.S. Appl. No. 11/835,631, "Plasma Extraction Apparatus" (CIP), filed Aug. 8, 2007.

Co-pending U.S. Appl. No. 12/016,315, "Spectroscopic Sample Holder" CIP, filed Jan. 18, 2008.

Co-pending U.S. Appl. No. 11/108,912, "Joint-Diagnostic Spectroscopic and Biosensor Cartridge", filed Apr. 19, 2005.

Co-pending U.S. Appl. No. 11/103,619 "Blood Collection and Measurement Apparatus", filed Apr. 12, 2005.

Office Action issued in connection with co-pending U.S. Appl. No. 11/432,616, filed May 12, 2006, mailed on Oct. 7, 2008.

Office Action issued in connection with co-pending U.S. Appl. No. 11/835,631, filed Aug. 8, 2007, mailed on Oct. 6, 2008.

Office Action issued in connection with co-pending U.S. Appl. No. 12/016,315, filed Jan. 18, 2008, mailed on Oct. 20, 2008.

Response filed in connection with co-pending U.S. Appl. No. 11/103,619, filed Apr. 12, 2005.

Office Action issued in connection with co-pending U.S. Appl. No. 11/466,588, filed Aug. 23, 2006, mailed on Feb. 20, 2009.

Office Action issued in connection with co-pending U.S. Appl. No. 12/016,315, filed Jan. 18, 2008, mailed on Apr. 2, 2009.

Office Action issued in connection with co-pending U.S. Appl. No. 11/432,616, filed May 12, 2006, mailed on Apr. 16, 2009.

Office Action issued in connection with co-pending U.S. Appl. No. 11/432,616, mailed on Sep. 17, 2009.

Office Action issued in connection with co-pending U.S. Appl. No. 12/016,315, mailed Sep. 24, 2009.

Office Action issued in connection with co-pending U.S. Appl. No. 12/016,315, filed Jan. 18, 2008, mailed on Sep. 24, 2009.

Office Action issued in connection with co-pending U.S. Appl. No. 11/466,588, filed Aug. 23, 2006, mailed on Jun. 22, 2009.

Office Action issued in connection with co-pending U.S. Appl. No. 11/835,631, filed Aug. 8, 2007, mailed on Jun. 19, 2009.
Office Action issued in connection with co-pending U.S. Appl. No. 11/103,619, filed Apr. 12, 2005, mailed on Jan. 5, 2009.
Advisory Office Action issued in connection with co-pending U.S. Appl. No. 12/016,315, filed Jan. 18, 2008, mailed on Jun. 26, 2009.
Restriction Requirement Office Action issued in connection with co-pending U.S. Appl. No. 11/477,588, filed Aug. 23, 2006, mailed on Feb. 20, 2010.
Office Action issued in connection with co-pending U.S. Appl. No. 11/835,631, filed Aug. 8, 2007, mailed on Mar. 25, 2010.
Co-pending U.S. Appl. No. 12/752,048, "Blood Sample Holder for Spectroscopic Analysis", filed Mar. 31, 2010.
Restriction Requirement Office Action received in connection with co-pending U.S. Appl. No. 11/738,889, filed May 2, 2006, mailed on May 26, 2010.
Notice of Allowance Office Action issued in connection with co-pending U.S. Appl. No. 11/432,616, filed May 12, 2006, mailed on Mar. 25, 2010.
Notice of Allowance Office Action issued in connection with co-pending U.S. Appl. No. 12/016,315, filed Jan. 1, 2008, mailed on Mar. 26, 2010.
Notice of Allowance issued in connection with co-pending U.S. Appl. No. 11/432,616, filed May 12, 2006, mailed on Jun. 14, 2010.
Notice of Allowance issued in connection with co-pending U.S. Appl. No. 11/835,631, filed Aug. 8, 2007, mailed on Jul. 1, 2010.
Office Action issued in connection with U.S. Appl. No. 11/738,889, dated Oct. 4, 2010.
Co-pending U.S. Appl. No. 12/897,581, "Plasma Extraction Apparatus", filed Oct. 4, 2010.
Co-pending U.S. Appl. No. 12/813,207, "Blood Sample Holder for Spectroscopic Analysis", filed Jun. 10, 2010.
Written Opinion of the International Searching Authority for related international application No. PCT/CA2005/000326, mailed Jul. 7, 2005.
International Preliminary Report on Patentability (IPRP) for related international application No. PCT/CA2005/000326, mailed Jul. 7, 2005.
International Search Report for related International application No. PCT/CA2005/000326, mailed Jul. 7, 2005.
Co-pending U.S. Appl. No. 11/071,247, "Joint-diagnostic in vivo and in vitro apparatus", filed Mar. 4, 2005.
Restriction Requirement issued in connection with co-pending U.S. Appl. No. 11/071,247, filed Mar. 4, 2005, mailed Jun. 12, 2009.
Office Action in connection with co-pending U.S. Appl. No. 11/071,247, filed Mar. 4, 2005, mailed Dec. 23, 2009.
Office Action in connection with co-pending U.S. Appl. No. 11/071,247, filed Mar. 4, 2005, mailed Aug. 19, 2010.
Office Action issued in connection with co-pending U.S. Appl. No. 11/738,889, filed Apr. 23, 2007, mailed Mar. 7, 2011.

* cited by examiner

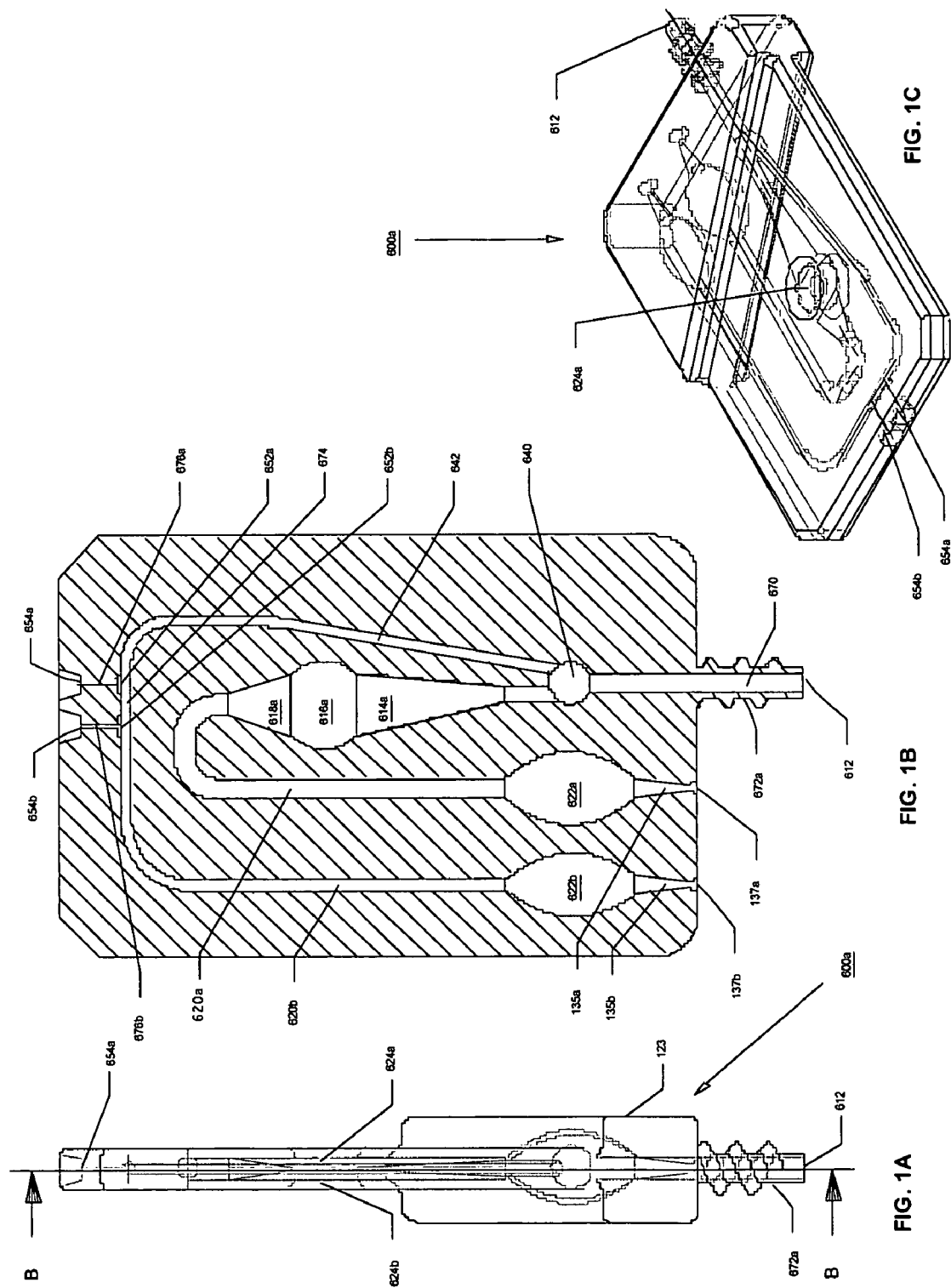

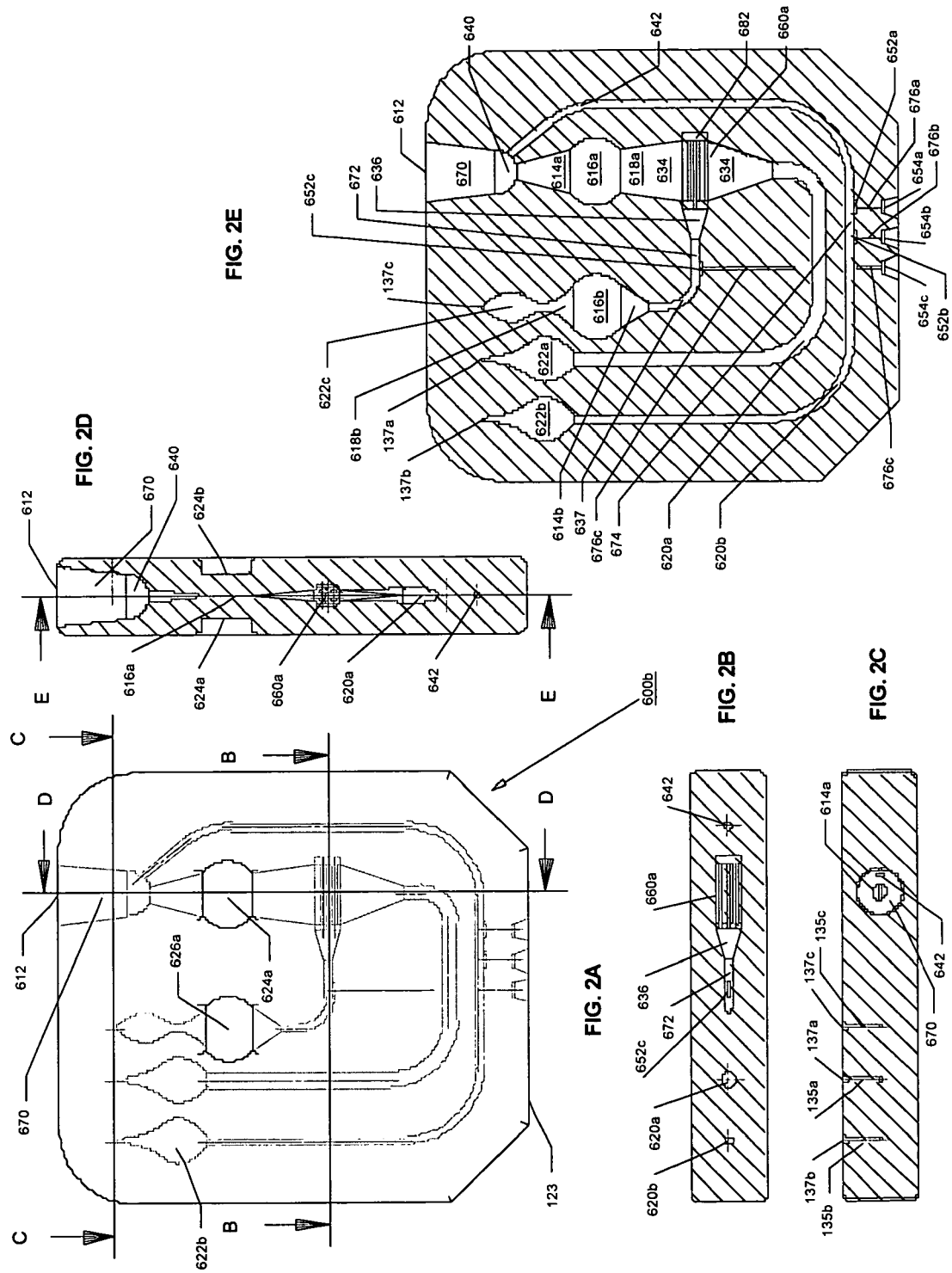

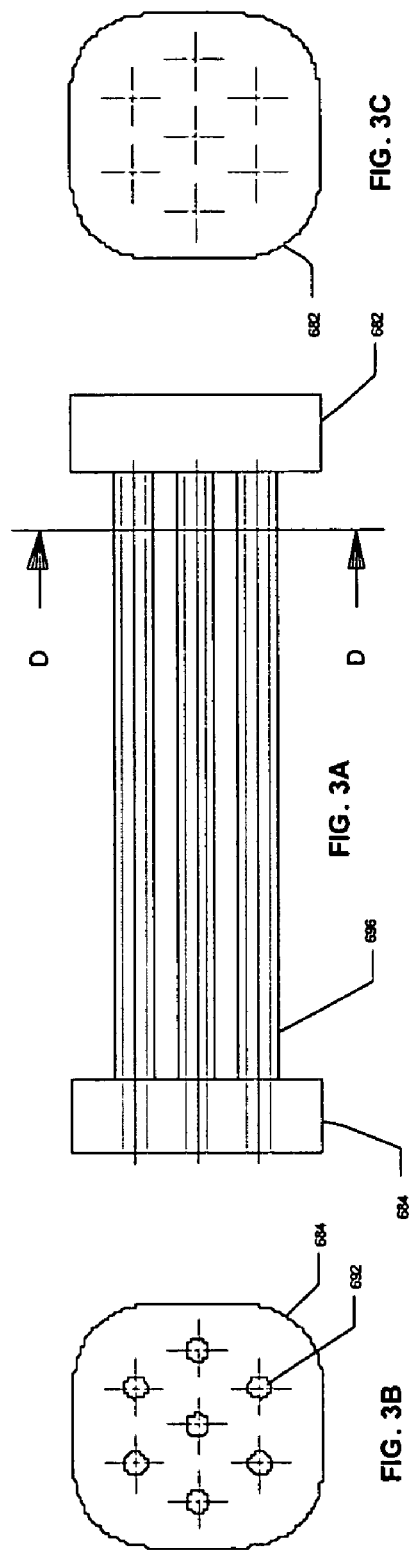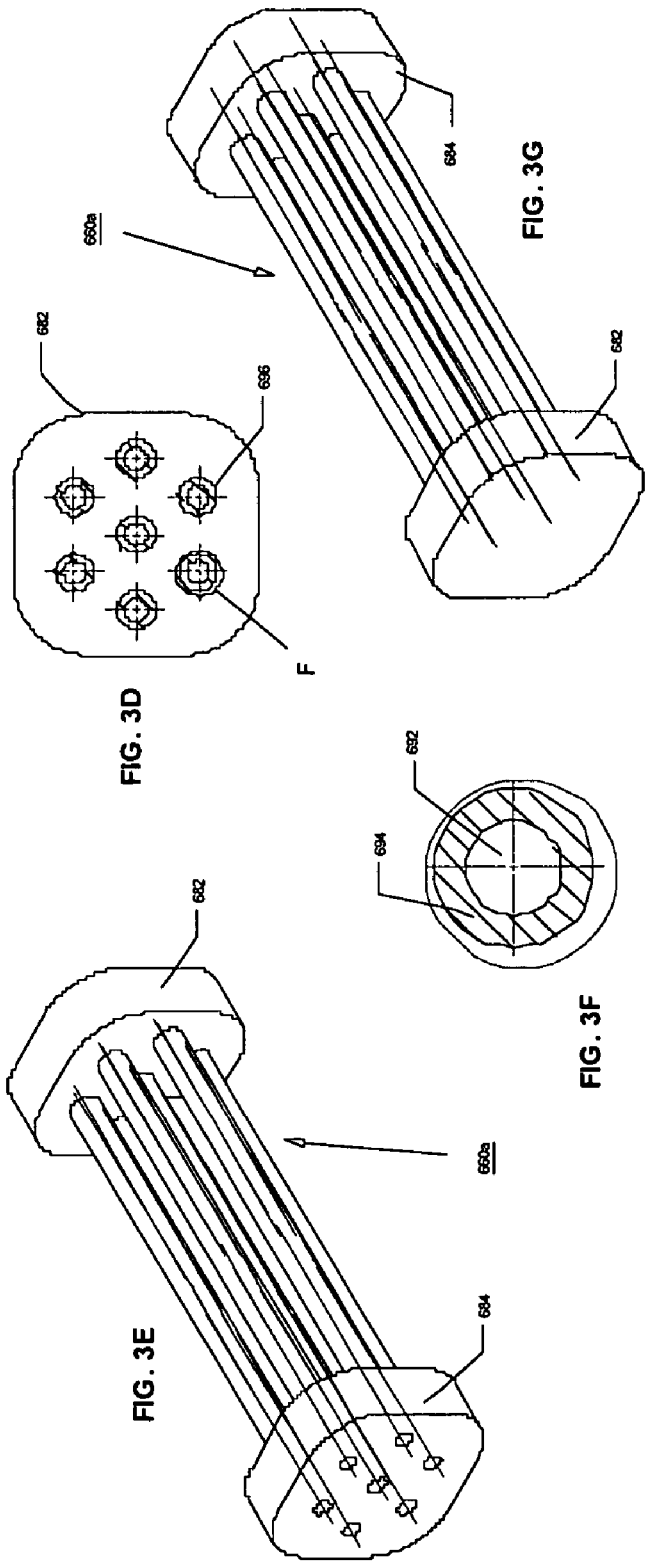

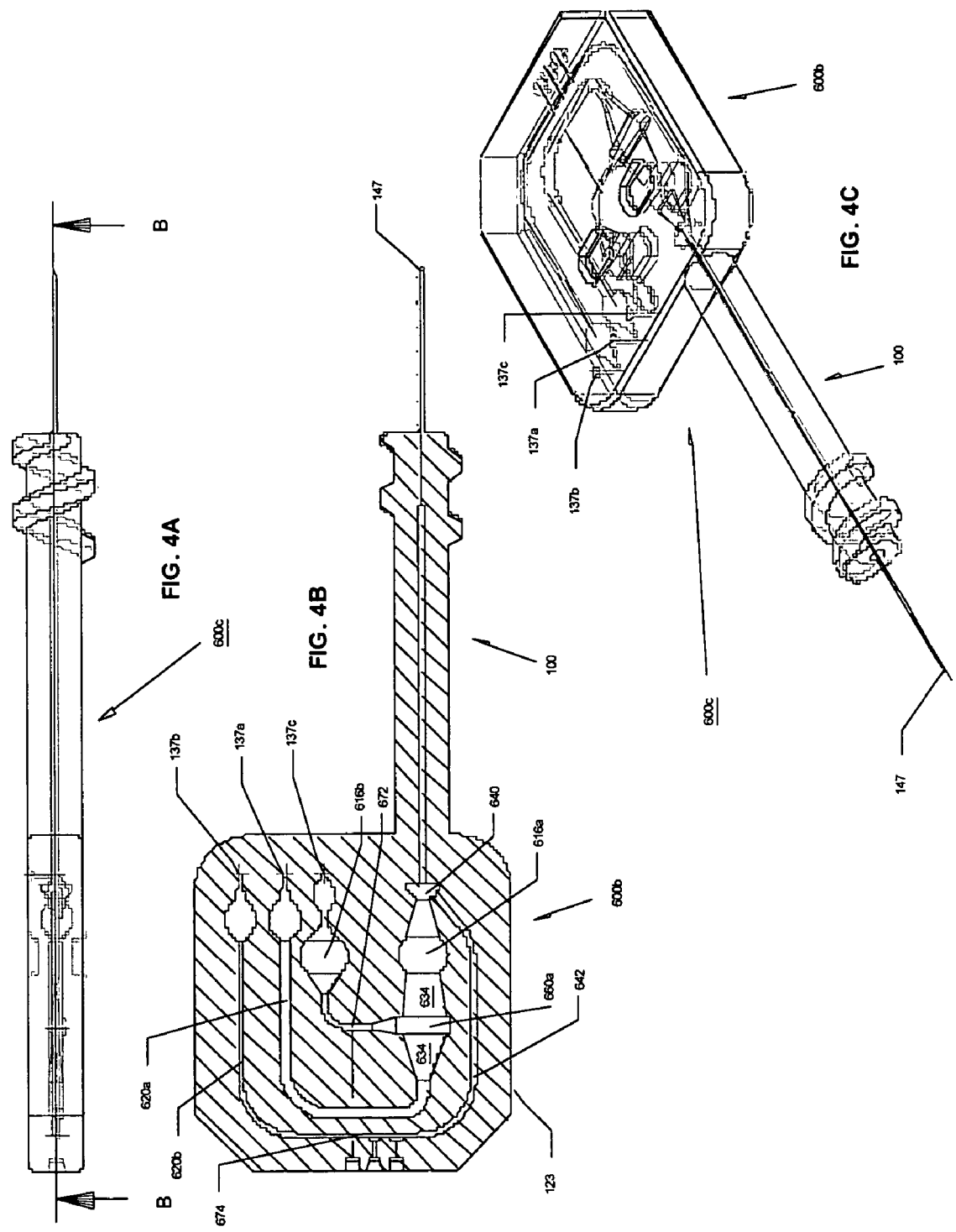

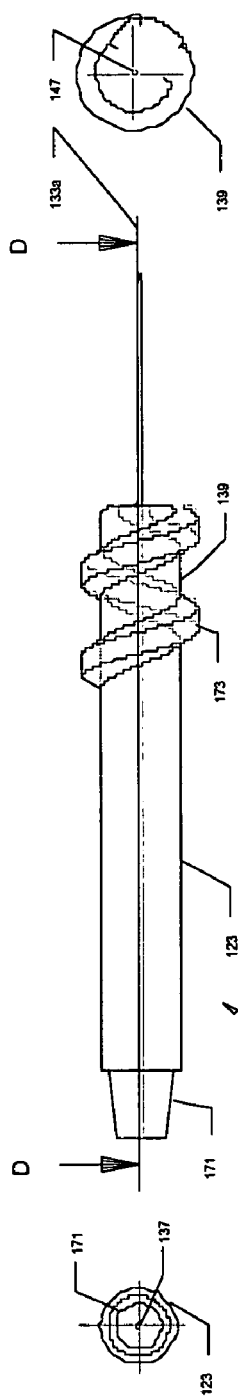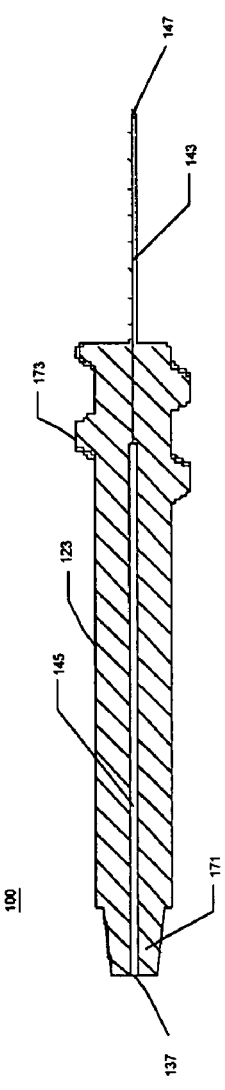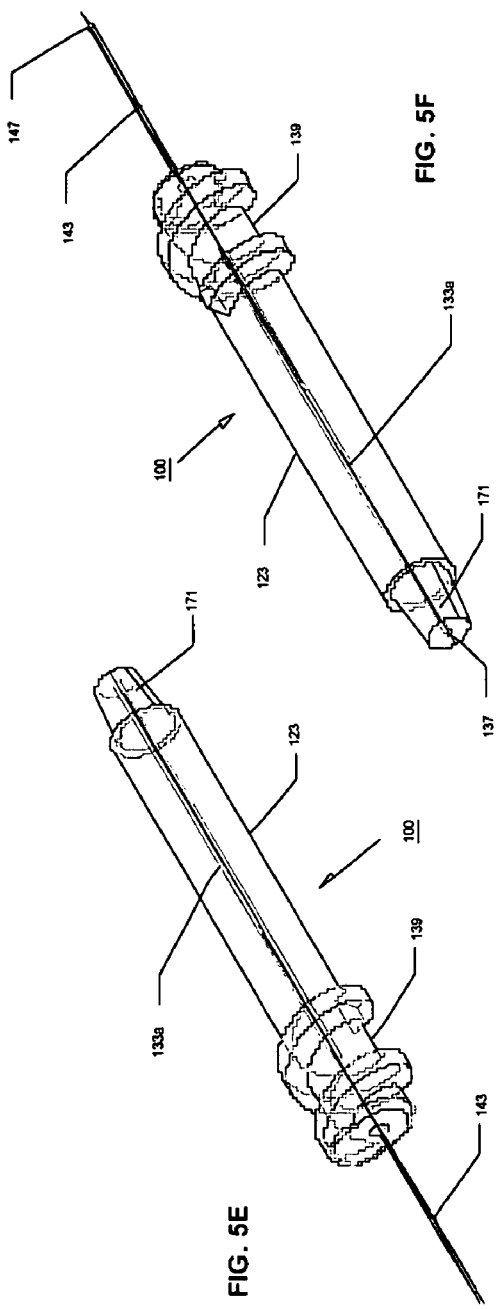

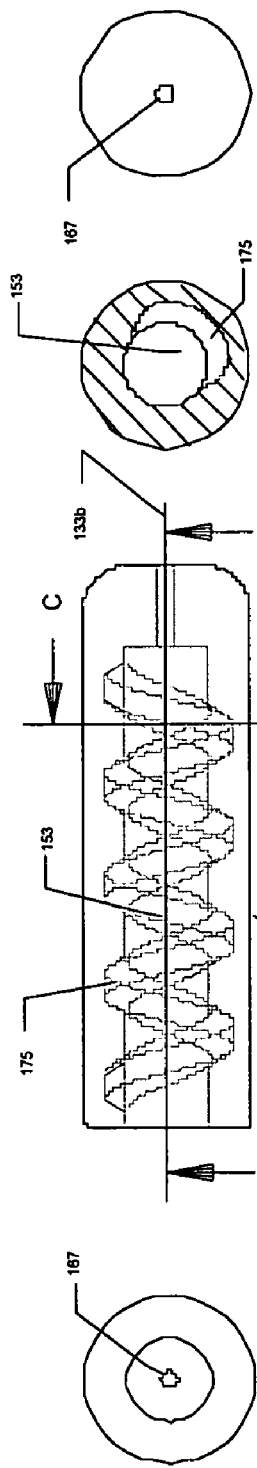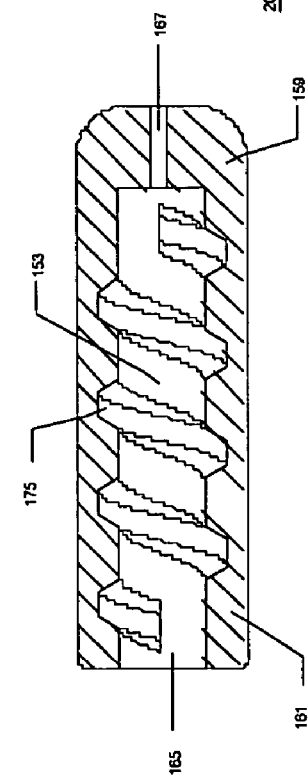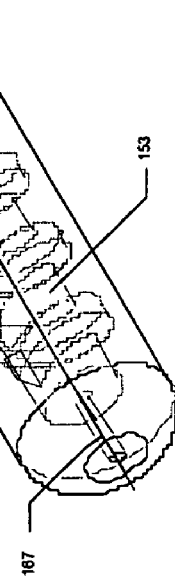
FIG. 6D
FIG. 6C
FIG. 6A
FIG. 6B
FIG. 6E
FIG. 6F

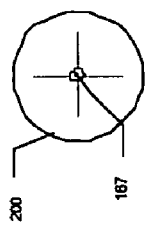
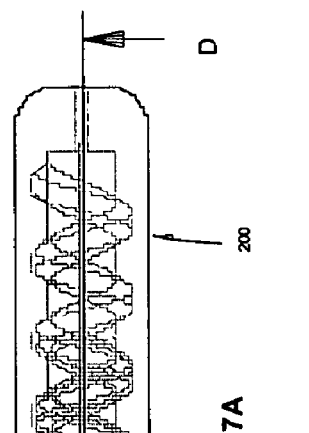
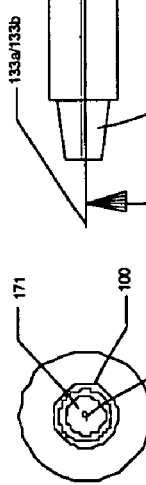
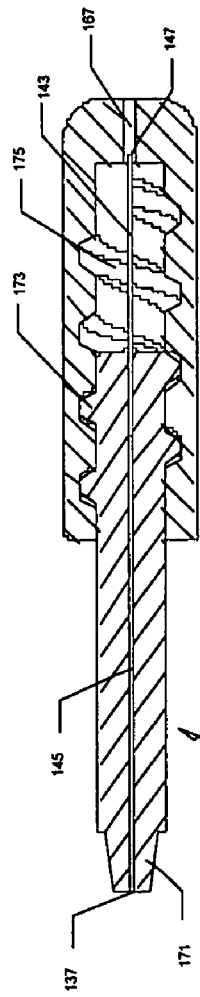
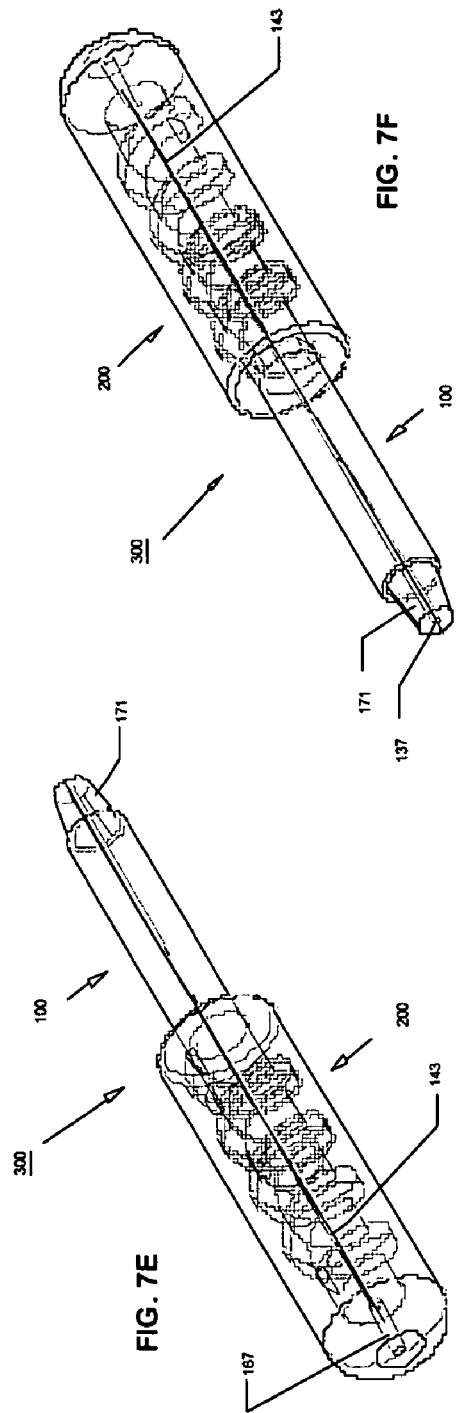
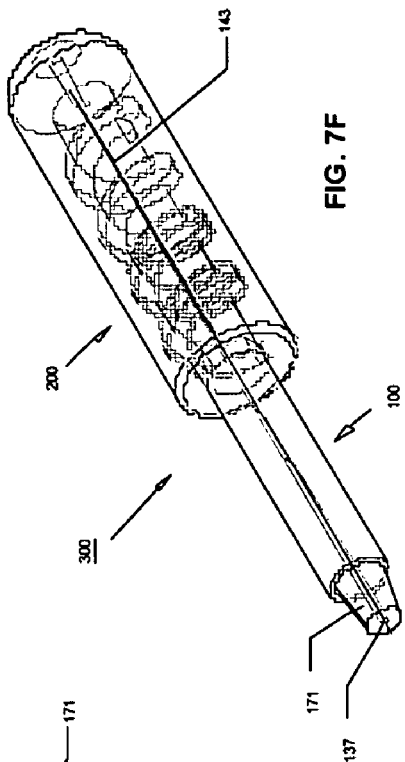

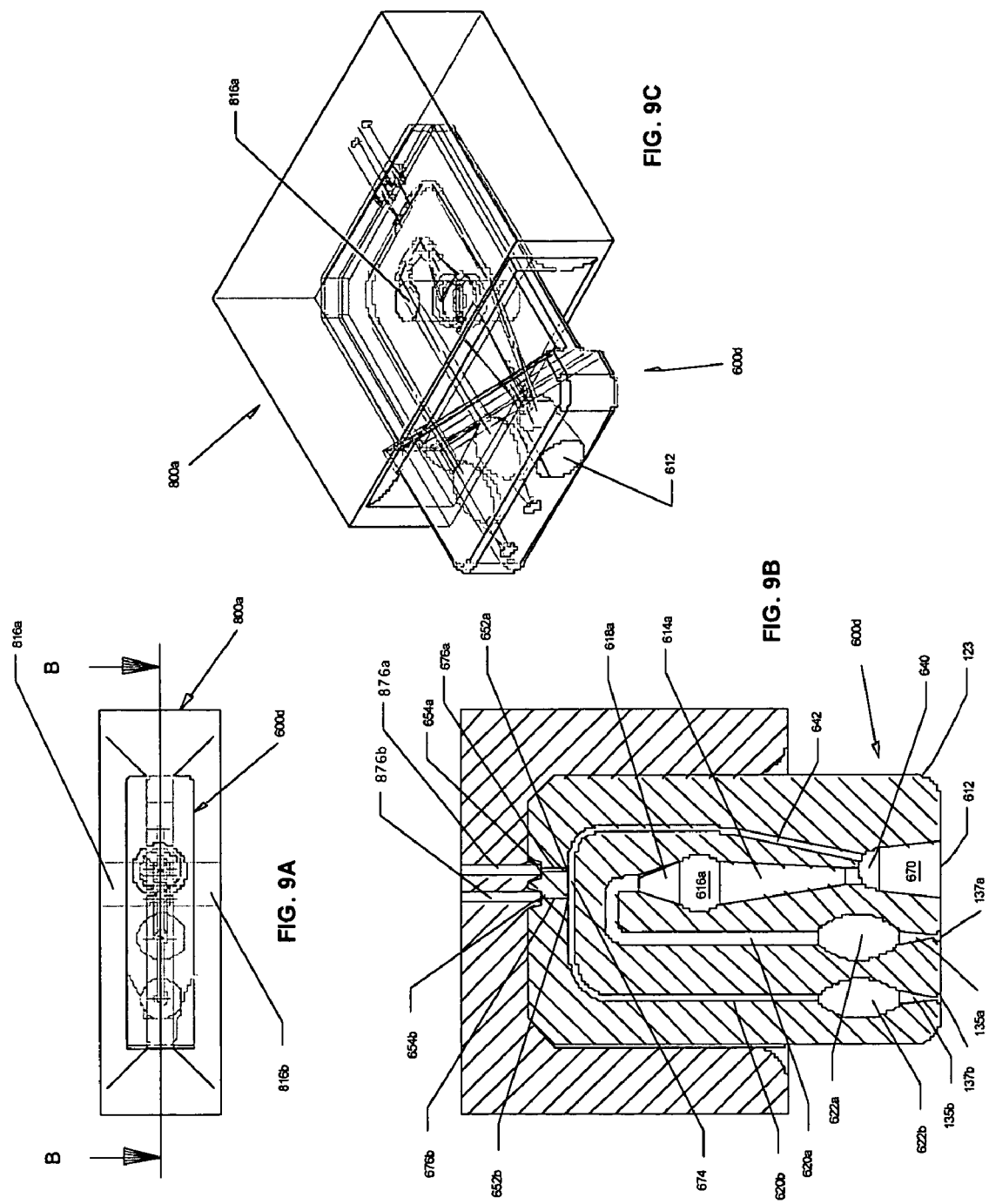

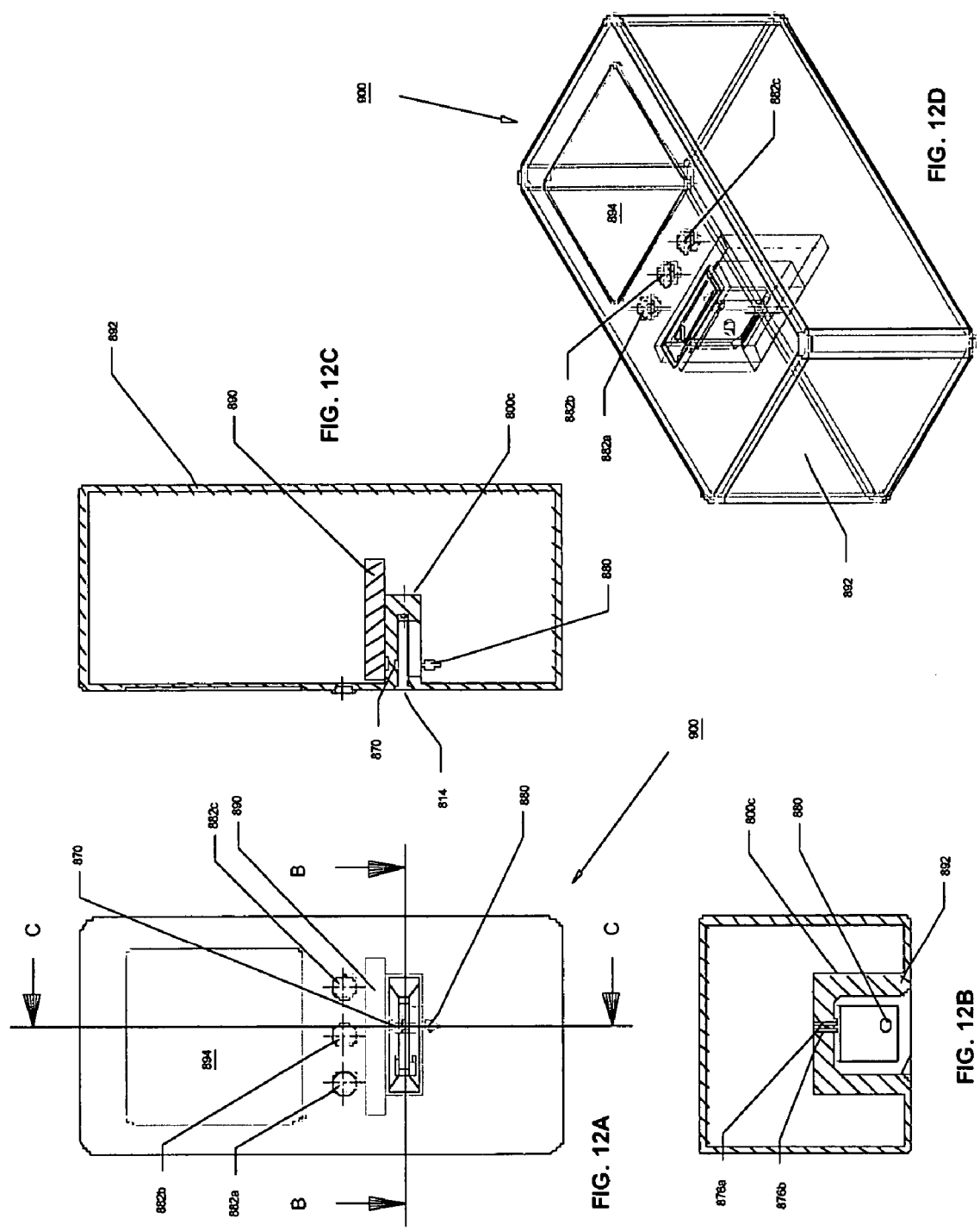

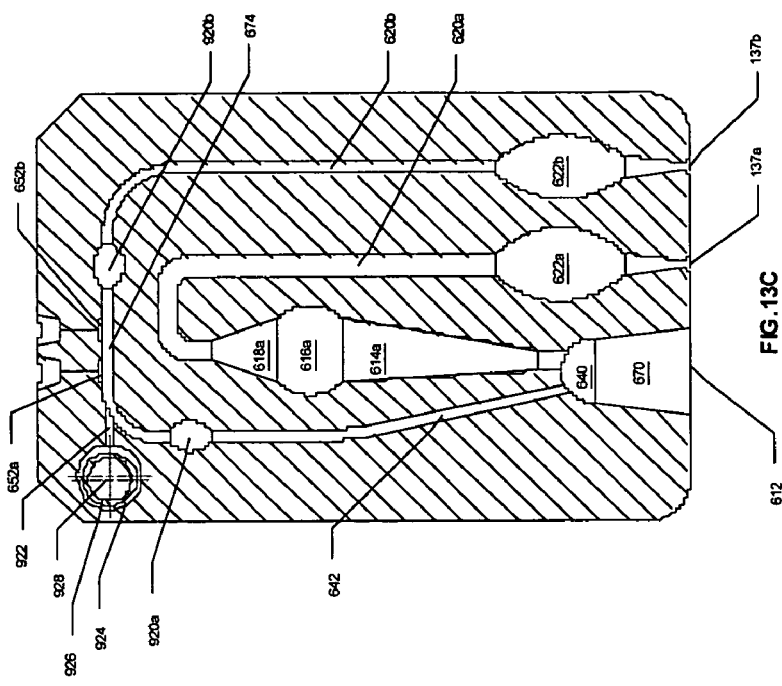
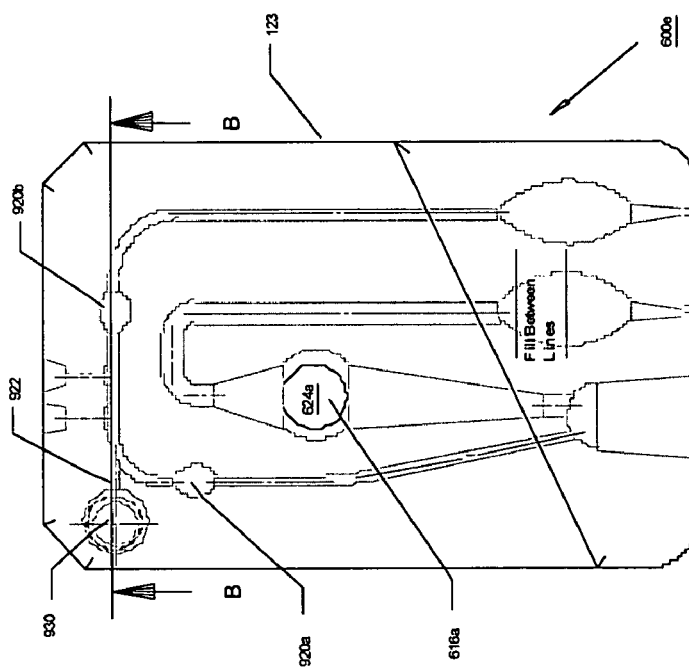
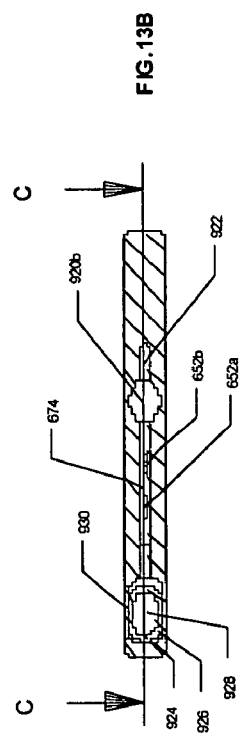
FIG. 13A
FIG. 13B
FIG. 13C

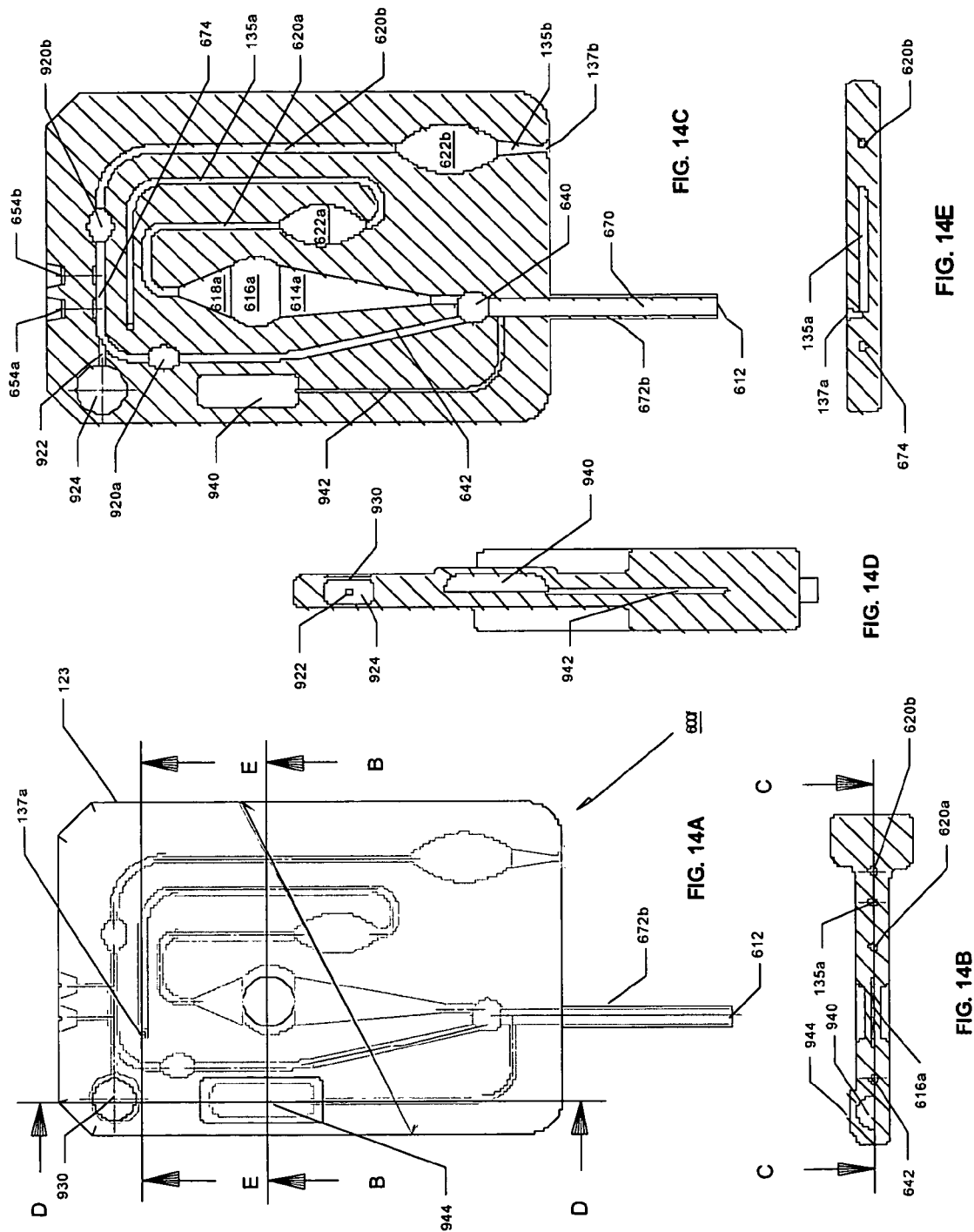

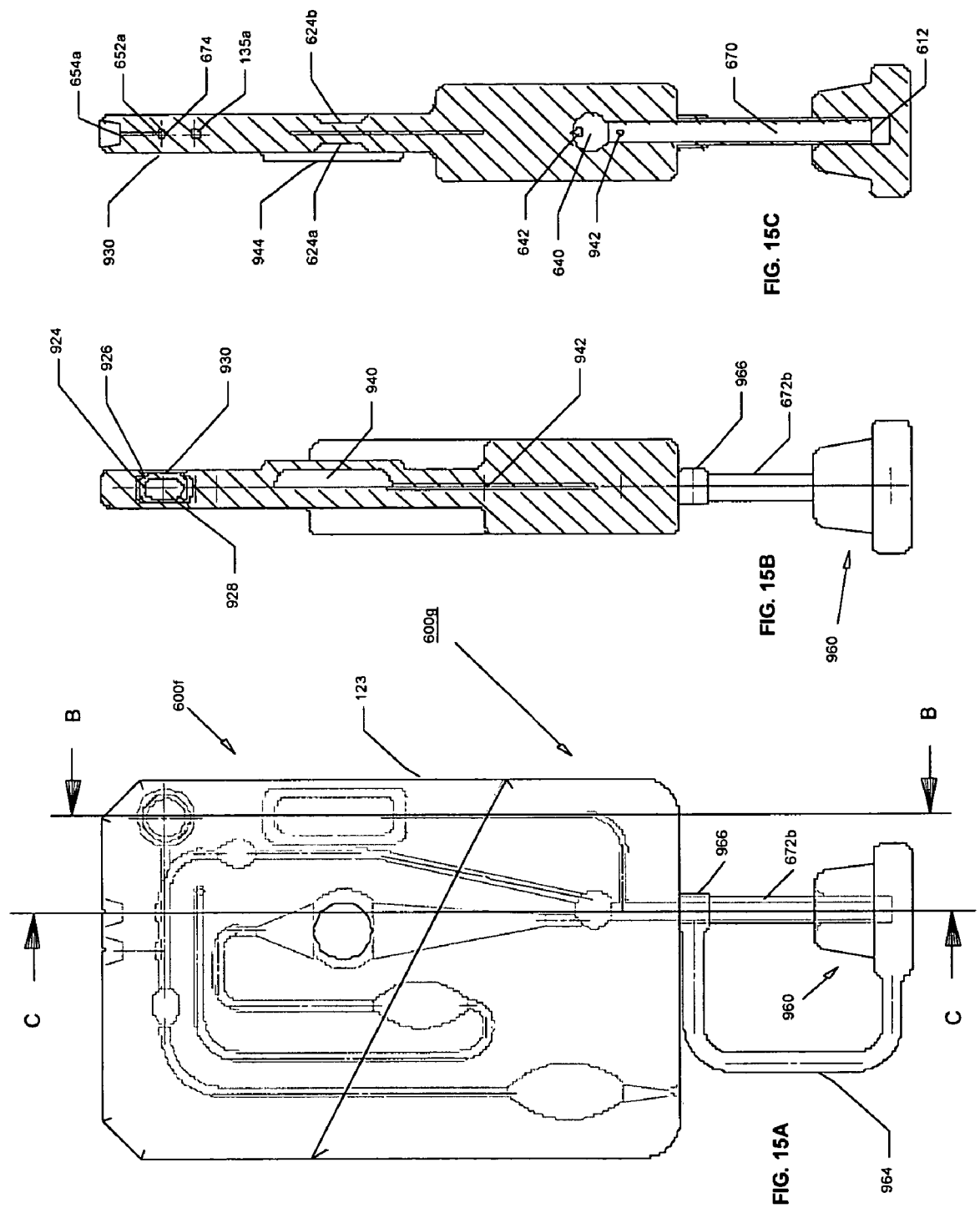

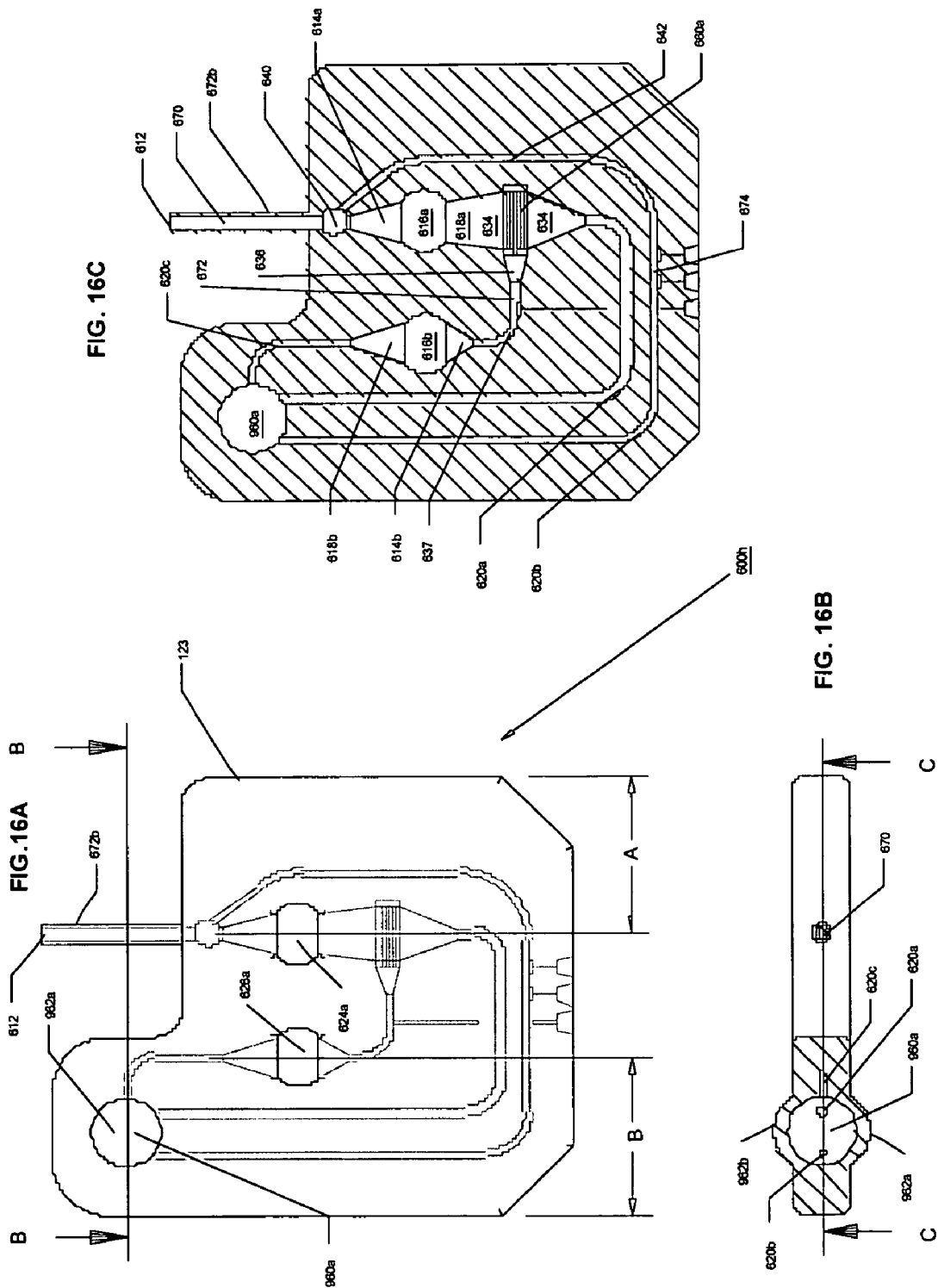

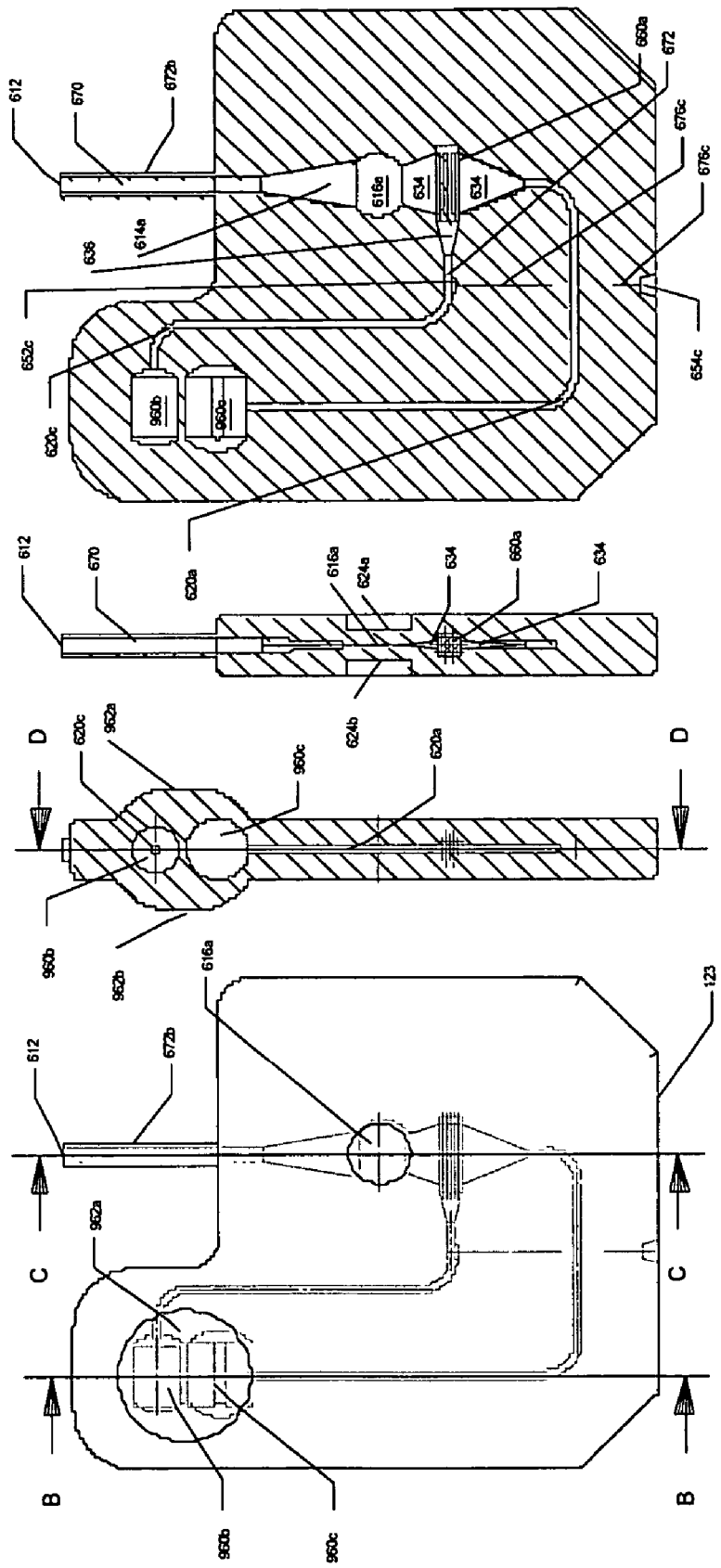

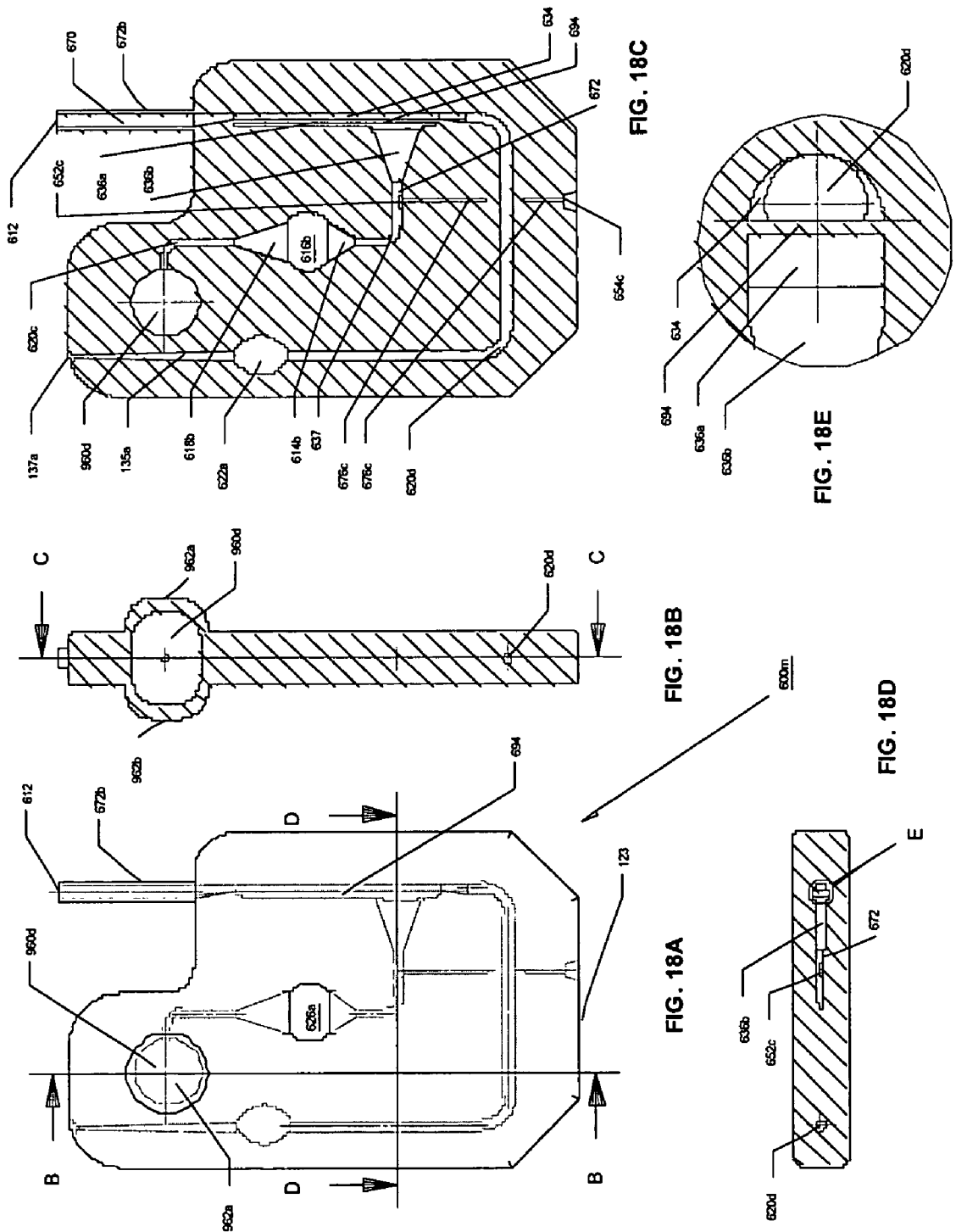

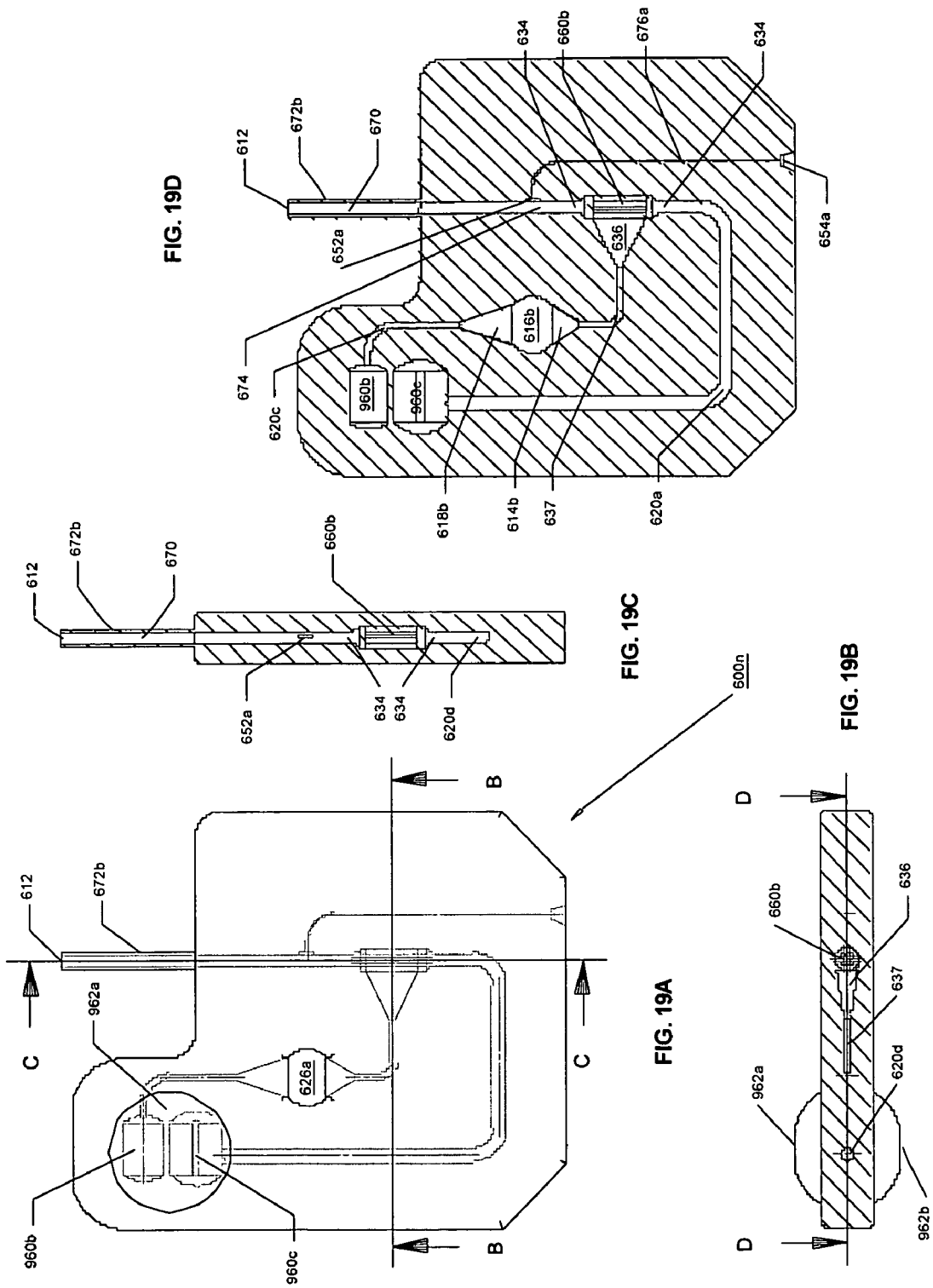

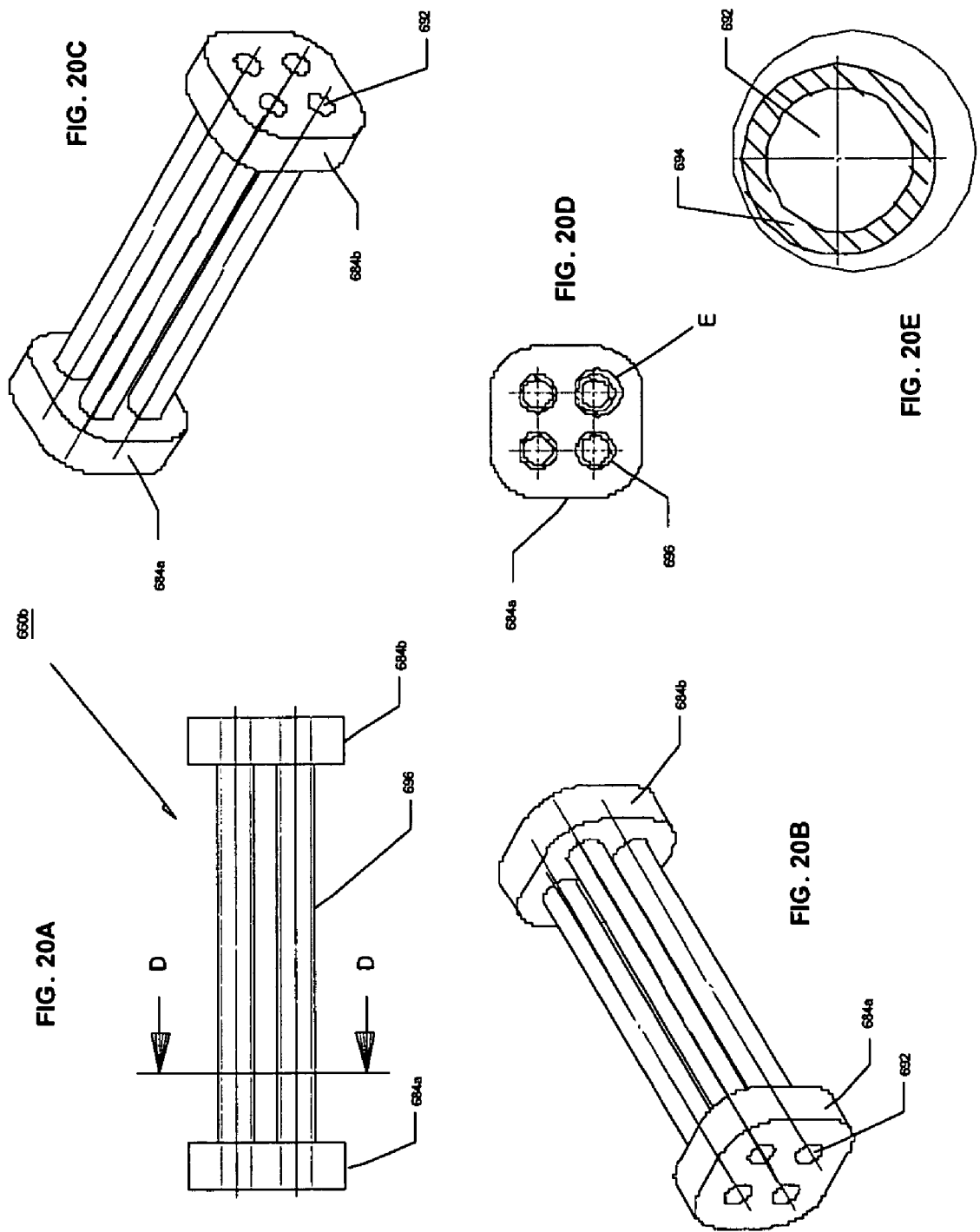

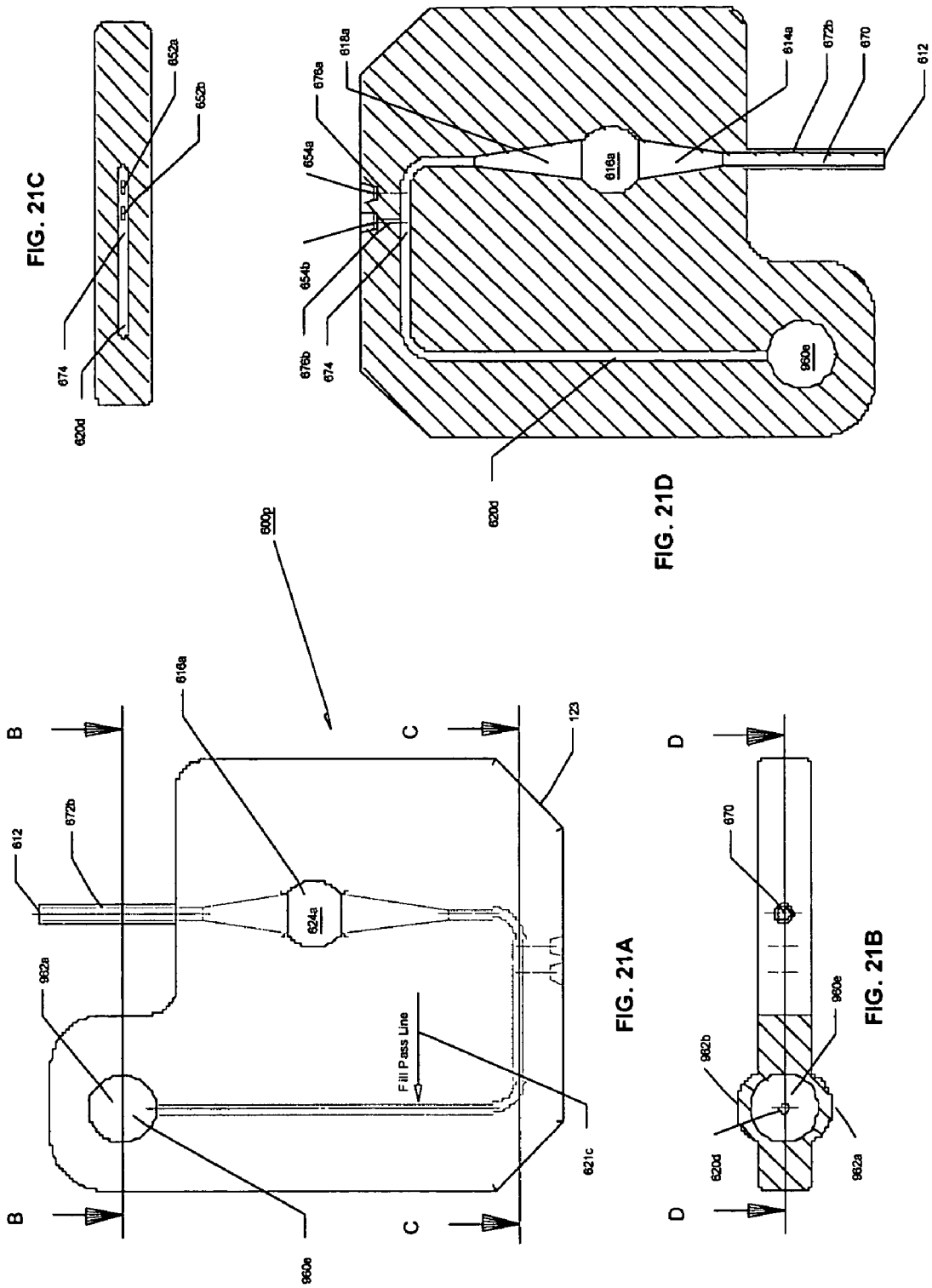

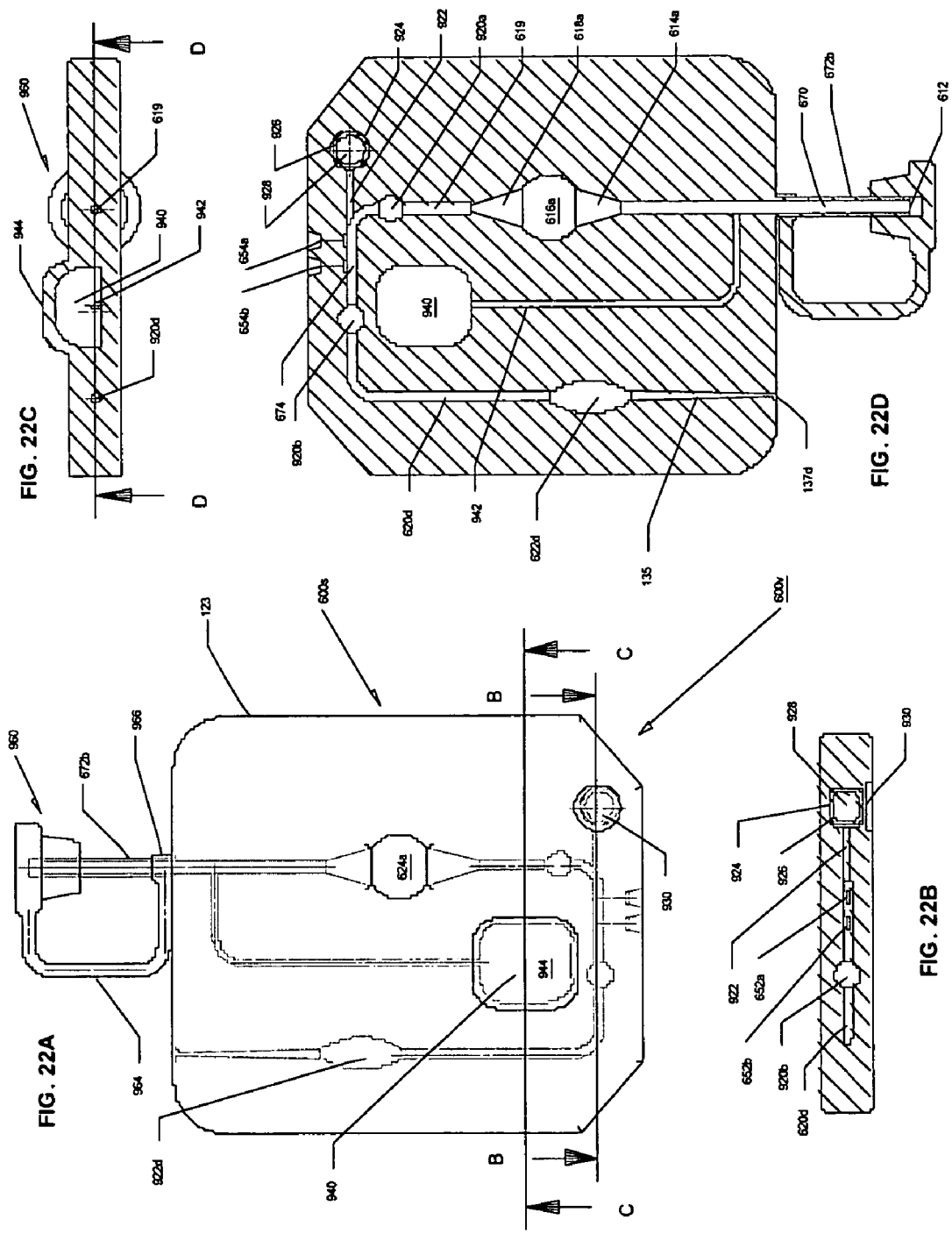

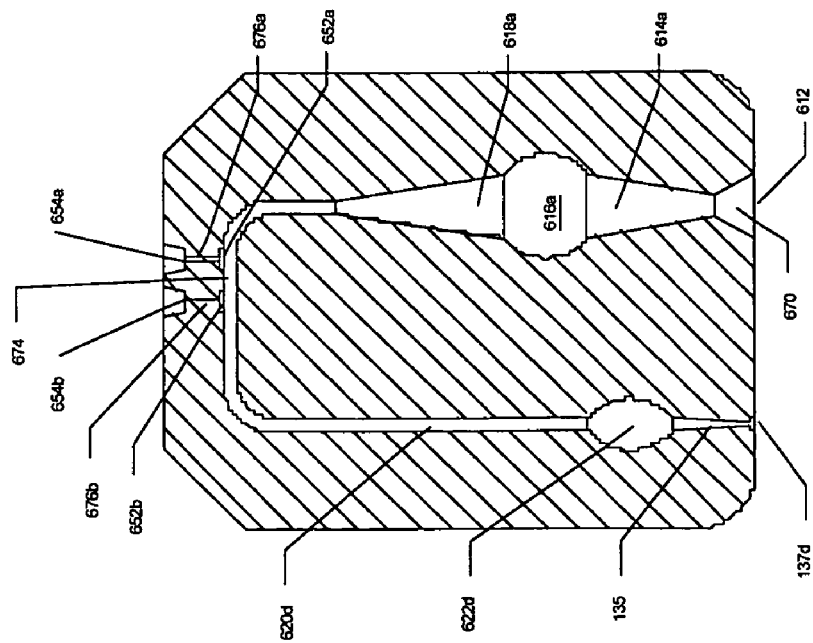
FIG. 23C
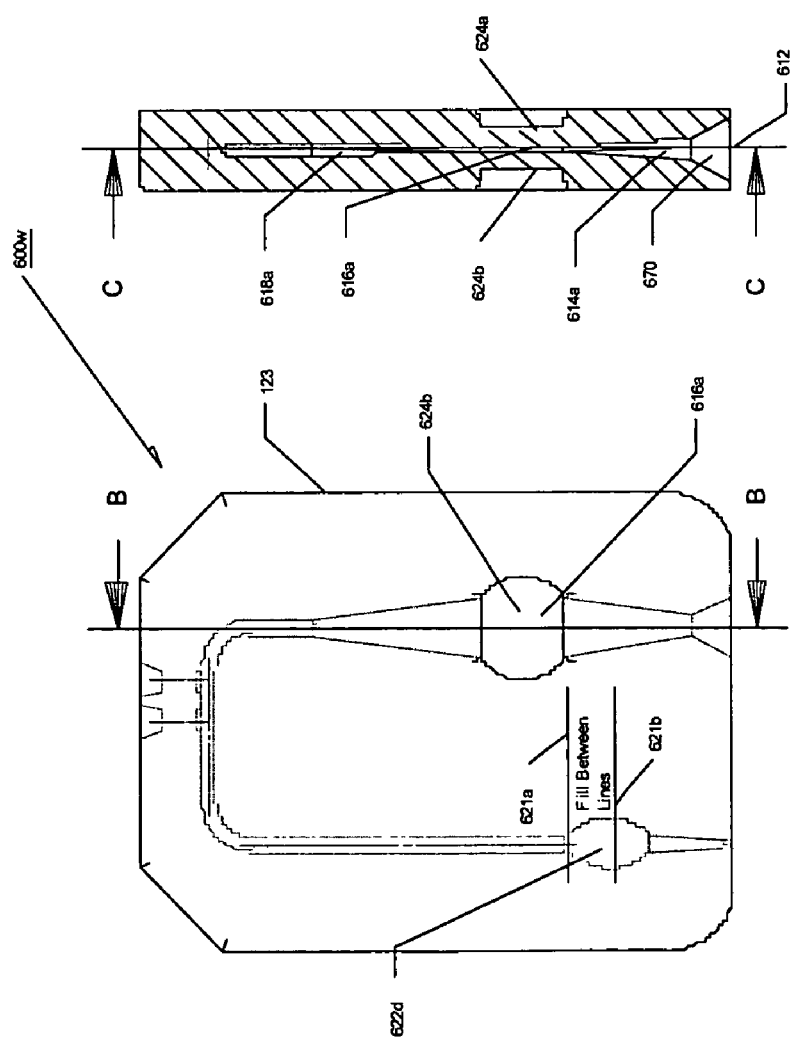
FIG. 23B
FIG. 23A

JOINT-DIAGNOSTIC SPECTROSCOPIC AND BIOSENSOR METER

RELATED APPLICATION

This application is a continuation-in-part of U.S. patent application Ser. No. 10/103,619 filed Apr. 12, 2005 and U.S. patent application Ser. No. 11/108,912 filed Apr. 19, 2005.

FIELD OF THE INVENTION

The invention relates to meters, which measure fluid samples contained in disposable microfluidic cartridges, using a combination of spectroscopic and biosensor technology.

BACKGROUND OF THE INVENTION

There are many medical diagnostic tests that require a fluid, for example without limitation, blood (sometimes referred to as whole blood, in order to differentiate blood from serum and plasma), serum, plasma, cerebrospinal fluid, synovial fluid, lymphatic fluid, calibration fluid, and urine. With respect to blood, a blood sample is typically withdrawn in either an evacuated tube containing a rubber septum (a vacutainer), or a syringe, and sent to a central laboratory for testing. The eventual transfer of blood from the collection site to the testing site results in inevitable delays. Moreover, the red blood cells are alive and continue to consume oxygen during any delay period, which in turn changes chemical composition of the blood sample in between the time the blood sample is obtained and the time the blood sample is finally analyzed.

One example of a blood analysis technique that is affected by the aforementioned sources of error is co-oximetry. Co-oximetry is a spectroscopic technique that can be used to measure the different Hemoglobin (Hb) species present in a blood sample. The results of co-oximetry can be further evaluated to provide Hb Oxygen Saturation (Hb $sO_2$) measurements. If the blood sample is exposed to air, the Hb $sO_2$ measurements are falsely elevated, as oxygen from the air is absorbed into the blood sample. Co-oximetry also typically requires hemolyzing of the red blood cells (hemolysis), using a sound generator, to make the blood sample suitable for spectroscopic measurement. Hemolysis can also be accomplished by chemical means. Parameters that can be measured in blood by spectroscopic techniques (or spectroscopy, sometimes referred to as spectrometry) are limited by the amount of electromagnetic radiation (EMR) absorbed by the analytes measured. For example, without limitation, hydrogen ions (which determine pH) and electrolytes (sodium, potassium, chloride and bicarbonate) do not absorb EMR in the approximate wavelength range of about 300 nm to 2500 nm. Therefore, if this wavelength range is used to conduct spectroscopic measurements of Hb species for example, then these important parameters, i.e., hydrogen ions and electrolytes, must be measured by other means.

Another example of a blood analysis technique that is affected by the aforementioned sources of error is blood gases. Traditionally, blood gas measurement includes the partial pressure of oxygen, the partial pressure of carbon dioxide, and pH. From these measurements, other parameters can be calculated, for example, Hb $sO_2$. Blood gas and electrolyte measurements usually employ biosensors. Bench-top analyzers are available, which (1) measure blood gases, (2) perform co-oximetry, or (3) measure blood gases and perform co-oximetry in combination. Some combinations of diagnostic measurement instruments also include electrolytes, making such bench-top analyzers even larger. Because these instruments are large and expensive, they are usually located in central laboratories. Biosensor technology is also limited by the blood parameters it can measure. To the inventor's knowledge, biosensors are not currently available for measuring the Hb species measured by co-oximeters.

Preferably, blood gases and co-oximetry are measured in arterial blood collected in a syringe, since arterial blood provides an indication of how well venous blood is oxygenated in the lungs. There are many benefits to providing these blood tests near or at the point of care of patients, but these are usually limited by the size and cost of the diagnostic measurement instruments. As a non-limiting example, assessment of the acid-base status of a patient requires both the measurement of hemoglobin (Hb) species in the blood and the blood pH. Therefore, there is a need for small portable meters, which combine spectroscopic technology with biosensor technology.

SUMMARY OF THE INVENTION

According to an aspect of an embodiment of the invention there is provided a spectroscopic and biosensor system for analyzing a blood sample taken from a patient, the system comprising a disposable cartridge and a meter. In one embodiment of the invention, the disposable cartridge comprises: a) a cartridge housing; b) an inlet opening in the cartridge housing for receiving the blood sample; c) one or more than one flow path to receive the blood sample from the inlet opening; d) an optical chamber in the one or more than one flow path, the optical chamber having at least one optical window to facilitate detection of an electromagnetic radiation-based signal derived from the blood; e) a biosensor chamber in the one or more than one flow path, the biosensor chamber comprising a pH biosensor, the cartridge housing further comprising an electrical output contact in electrical communication with the pH biosensor for receiving sample biosensor data from the pH biosensor after the blood sample makes contact with the pH biosensor; and f) at least one of an outlet vent and a compression suction chamber for facilitating flow of the blood sample inside the one or more than one flow path. The meter, absent one or more blood fluid connection with the disposable cartridge, comprises: a) a meter housing; b) a meter source of electromagnetic radiation; c) a slot in the meter housing for receiving the cartridge, the slot having an electrical input contact for mating with the output contact of the cartridge when the cartridge is inserted into the slot; and d) one or more than one photodetector for measuring electromagnetic radiation transmitted through or reflected from the blood sample within the optical chamber and for providing an electromagnetic radiation-based signal derived from the electromagnetic radiation transmitted through or reflected from the blood sample; and e) a processor, the processor comprising: 1) a blood hemoglobin oxygen saturation calibration algorithm for transforming the electromagnetic radiation-based signal into a blood hemoglobin oxygen saturation result; and 2) a pH calibration algorithm for transforming the sample biosensor data into a pH result, the processor being in communication with i) the one or more than one photodetector to receive the electromagnetic radiation-based signal, and ii) the electrical input contact to receive the sample biosensor data. The blood hemoglobin oxygen saturation result and the blood pH result will provide an assessment of the patient's oxygenation and acid-base status.

According to another aspect of an embodiment of the invention, there is provided a disposable cartridge for providing an EMR-based signal and sample biosensor data from a fluid sample, the disposable cartridge comprising: a) a cartridge housing; b) an inlet opening in the cartridge housing for receiving the fluid sample; c) a manifold for diverting the fluid sample received from the inlet opening into a spectroscopic flow path and a biosensor flow path separated from the spectroscopic flow path, wherein the spectroscopic flow path comprises at least one optical chamber having at least one optical window to facilitate detection of the EMR-based signal derived from the fluid sample, the spectroscopic flow path absent one or more biosensor for analyte measurement, and the biosensor chamber flow path comprises at least one biosensor comprising at least one of a pH biosensor, a transistor, an ion-selective membrane, a membrane-bound enzyme, a membrane-bound antigen, a membrane-bound antibody and a membrane-bound strand of nucleic acid for providing sample biosensor data, the cartridge housing further comprising an electrical output contact in electrical communication with each biosensor for receiving the sample biosensor data, the biosensor flow path absent one or more optical chamber for analyte measurement; and d) at least one of an outlet vent and a compression suction chamber for facilitating flow of the sample fluid inside the spectroscopic flow path and the biosensor flow path.

According to yet another aspect of an embodiment of the invention there is provided a system comprising a disposable cartridge and a meter for providing an electromagnetic radiation-based signal and sample biosensor data from a fluid sample. The disposable cartridge comprises: a) a cartridge housing; b) an inlet opening in the cartridge housing for receiving the fluid sample; c) one or more than one flow path in the cartridge housing for receiving the fluid sample from the inlet opening; d) an optical chamber in the one or more than one flow path, the optical chamber having at least one optical window to facilitate detection of an electromagnetic radiation-based signal derived from the fluid sample; e) a biosensor chamber in the one or more than one flow path, the biosensor chamber comprising a biosensor, wherein the cartridge housing further comprises an electrical output contact in electrical communication with the biosensor for receiving the sample biosensor data from the biosensor after the sample makes contact with the biosensor; f) a cartridge front end including an approximate location of the electrical output contact; and g) at least one of an outlet vent and a compression suction chamber for facilitating flow of the fluid sample inside the one or more than one flow path. The meter comprises: a) a slot for receiving the cartridge, the slot having a slot front end and a slot back end, the slot front end including the slot opening and the slot back end substantially remote from the front end, the slot back end including an electrical input contact; and b) a meter source of electromagnetic radiation. The system further comprises: a) a plane of entry of the cartridge through the slot opening, the cartridge front end being the first portion of the cartridge to enter the slot opening, wherein the plane of entry is substantially parallel to the at least one optical window; and b) means for sliding the cartridge along the plane of entry in order to concurrently align the optical chamber with the meter source of electromagnetic radiation and mate the electrical output contact with the electrical input contact. The electromagnetic-based signal and the sample biosensor data will be used to measure analytes in the fluid sample.

According to yet another aspect of an embodiment of the invention, there is provided a spectroscopic and biosensor system for analyzing a blood sample taken from a patient, the system comprises: i) a disposable cartridge; ii) spectroscopic means for measuring a blood hemoglobin oxygen saturation value; and iii) biosensor means for measuring a blood pH value. The disposable cartridge comprises: a) a cartridge housing; b) an inlet opening in the cartridge housing for receiving the blood sample; c) one or more than one flow path in the cartridge housing for receiving the blood sample from the inlet opening; d) an optical chamber in the one or more than one flow path, the optical chamber having at least one optical window to facilitate the spectroscopic means for measuring a blood hemoglobin oxygen saturation value; e) a biosensor chamber in the one or more than one flow path, the biosensor chamber comprising a pH biosensor to facilitate the biosensor means for measuring a blood pH value; and f) one of an outlet vent and a compression suction chamber for promoting flow of the blood sample inside the flow path. The blood hemoglobin oxygen saturation value and the blood pH value will provide an assessment the patient's oxygenation and acid-base status.

According to yet another aspect of an embodiment of the invention, there is provided aspectroscopic and biosensor method for analyzing a blood sample taken from a patient. The method comprises: a) obtaining a blood sample from the patient; b) providing a disposable cartridge; c) providing a meter; d) urging the blood into the one or more than one flow path in order to fill at least the optical chamber; e) positioning the optical chamber to receive the meter source of electromagnetic radiation by mating the electrical output contact with the electrical input contact and, at one of a period prior to urging the blood into the one or more than one flow path and a period after urging the blood into the one or more than one flow path; f) irradiating the blood in the optical chamber with the meter source of electromagnetic radiation and measuring electromagnetic radiation transmitted through or reflected from the blood with the one or more than one photodetector, thereby generating the electromagnetic radiation-based signal; g) urging the blood into the biosensor chamber for the blood to make contact with the pH biosensor, if the blood is not yet urged into the biosensor chamber, for generating blood biosensor data; and h) processing the electromagnetic radiation-based signal and the blood biosensor data to produce a blood hemoglobin oxygen saturation value and a blood pH value respectively. The disposable cartridge comprises: i) a cartridge housing; ii) an inlet opening in the cartridge housing for receiving the blood; iii) one or more than one flow path to receive the blood from the inlet opening; iv) an optical chamber in the one or more than one flow path, the optical chamber comprising at least one optical window to facilitate detection of an electromagnetic radiation-based signal derived from the blood; v) a biosensor chamber in the one or more than one flow path, the biosensor chamber comprising a pH biosensor; vi) an electrical output contact in communication with the pH biosensor; and vii) at least one of an outlet vent and a compression suction chamber to facilitate blood flow inside the one or more than one flow path. The meter comprises: i) a meter housing; ii) a meter source of electromagnetic radiation; iii) a slot in the meter housing for receiving the disposable cartridge, the slot comprising an electrical input contact; and iv) one or more than one photodetector. The blood hemoglobin oxygen saturation value and the blood pH value will provide an assessment of the patient's oxygenation and acid-base status.

The inlet opening of some embodiments of the disposable cartridge is a sharp open end of a needle, for entering the lumen of a blood vessel and receiving the blood.

In some embodiments of the disposable cartridge, the disposable cartridge further comprises: a) a cavity within the cartridge housing having a sealed calibration pouch containing a calibration fluid for calibrating the biosensor; b) a puncture element for puncturing the sealed calibration pouch and for releasing the calibration fluid from the sealed calibration pouch; c) a conduit for transporting the calibration fluid from the cavity to the biosensor chamber, the conduit being in fluid communication with the cavity and the biosensor chamber. In some more particular embodiments of the disposable cartridge, the disposable cartridge further comprises a first capillary break around an entrance to the biosensor chamber, and a second capillary break around an exit from the biosensor chamber, the first capillary break and the second capillary break being operable to retain the calibration fluid in the biosensor chamber.

In some embodiments of the disposable cartridge, the disposable cartridge further comprises a compressible air chamber in the cartridge housing, the compressible air chamber being fluidly connected to the biosensor chamber, the compressible air chamber being operable to displace the calibration fluid.

The inlet opening chamber of the disposable cartridge has one of several different configurations for receiving the sample, for example: a) configured to accept the end of a syringe; b) configured as a piece of capillary tubing; and c) configured with a flared opening, which can be placed over a pin prick.

A cartridge may contain one or more than one biosensor, depending on the embodiment. The biosensors used, comprise a transducer for converting at least one property of the fluid sample into an electrical signal. The transducer may comprise at least one active surface for contacting the fluid sample, and the active surface may be one of a chemical sensitive surface, or an ionic sensitive surface. The biosensor may comprise, at least one of a transistor, an ion-selective membrane, a membrane-bound enzyme, a membrane-bound antigen, a membrane-bound antibody, or a membrane-bound strand of nucleic acid.

In some embodiments of the system for analyzing a fluid sample, when the biosensors are not calibrated in each cartridge, the cartridge further comprises a barcode containing at least information regarding calibration of a biosensor, and the meter further comprises a barcode reader for reading the barcode.

In some embodiments of the system, the disposable cartridge further comprises a) a cavity within the cartridge housing having a sealed calibration pouch containing a calibration fluid for calibrating the biosensor; a puncture element for puncturing the sealed calibration pouch and for releasing the calibration fluid from the sealed calibration pouch; c) a conduit for transporting the calibration fluid from the cavity to the biosensor chamber, the conduit being in fluid communication with the cavity and the biosensor chamber; and d) a first capillary break around an entrance to the biosensor chamber, and a second capillary break around an exit from the biosensor chamber, the first capillary break and the second capillary break being operable to retain the calibration fluid in the biosensor chamber. Some examples of the puncture element includes: a) a projected member in the cavity; b) an object with projections on the object, the object being located inside the calibration pouch; and c) a weakened wall portion of the calibration pouch. In some embodiments of the disposable cartridge, the disposable cartridge further comprises a compressible air chamber within the cartridge housing, the compressible air chamber being fluidly connected to the one or more than one flow path at a point between the inlet opening and the biosensor chamber, the compressible air chamber being operable to displace the calibration fluid.

Other aspects and features of the present invention will become apparent, to those ordinarily skilled in the art, upon review of the following description of the specific embodiments of the invention.

BRIEF DESCRIPTION OF THE DRAWINGS

For a better understanding of the present invention, and to show more clearly how it may be carried into effect, reference will now be made, by way of example, to the accompanying drawings, which illustrate aspects of embodiments of the present invention and in which:

FIG. 1A is a schematic drawing showing details of a side view of a spectroscopic and biosensor cartridge 600a that can be used with a joint-diagnostic spectroscopic and biosensor meter according to an embodiment of the invention;

FIG. 1B is a cross-sectional view through the spectroscopic and biosensor cartridge 600a shown in FIG. 1A along line B-B;

FIG. 1C is a perspective view of the spectroscopic and biosensor cartridge 600a;

FIG. 2A is a schematic drawing showing details of the top view of a spectroscopic and biosensor whole blood and plasma cartridge 600b that can be used with a joint-diagnostic spectroscopic and biosensor meter according to an embodiment of the invention;

FIG. 2B is a first cross-sectional view through the spectroscopic and biosensor whole blood and plasma cartridge 600b shown in FIG. 2A along line B-B;

FIG. 2C is a second cross-sectional view through the spectroscopic and biosensor whole blood and plasma cartridge 600b shown in FIG. 2A along line C-C;

FIG. 2D is a third cross-sectional view through the spectroscopic and biosensor whole blood and plasma cartridge 600b shown in FIG. 2A along line D-D;

FIG. 2E is a fourth cross-sectional view through the spectroscopic and biosensor whole blood and plasma cartridge 600b shown in FIG. 2D along line E-E;

FIG. 3A is schematic drawing showing details of the hollow fiber filter bundle 660a shown in cartridge 600b, which is shown collectively in FIGS. 2A-2E;

FIG. 3B is the left side-view of the hollow fiber filter bundle 660a shown in FIG. 3A;

FIG. 3C is the right side-view of the hollow fiber filter bundle 660a shown in FIG. 3A;

FIG. 3D is a cross-sectional view through the hollow fiber filter bundle 660a shown in FIG. 3A along line D-D;

FIG. 3E is a perspective view of the hollow fiber filter bundle 660a;

FIG. 3F is a detailed view of the detail F shown in FIG. 3D;

FIG. 3G is an alternative perspective view of the hollow fiber filter bundle 660a;

FIG. 4A is a schematic drawing showing details of a side view of an integrated needle and cartridge 600c that can be used with a joint-diagnostic spectroscopic and biosensor meter according to an embodiment of the invention (the cartridge component 600b is shown collectively FIGS. 2A-2E, and the needle component 100 is shown collectively in FIGS. 5A-5F);

FIG. 4B is a cross-sectional view through the integrated needle and cartridge 600c shown in FIG. 4A along line B-B;

FIG. 4C is a perspective view of the integrated needle and cartridge 600c;

FIG. 5A is a schematic drawing showing details of a top view of a needle 100 that can be used with the cartridge 600b shown collectively in FIGS. 2A-2E, the cartridge 600d shown collectively in FIGS. 9A-9C, or the cartridge 600e shown collectively in FIGS. 13A-13C;

FIG. 5B is a left side view of the needle 100 shown in FIG. 5A;

FIG. 5C is a right side view of the needle 100 shown in FIG. 5A;

FIG. 5D is a cross-sectional view through the needle 100 shown in FIG. 5A along line D-D;

FIG. 5E is a perspective view of the needle 100;

FIG. 5F is an alternative perspective view of the needle 100;

FIG. 6A is a schematic drawing showing details of a top view of a barrel 200 for a needle 100 shown collectively in FIGS. 5A-5F, for sheathing and unsheathing the needle;

FIG. 6B is a left side view of the barrel 200 shown in FIG. 6A;

FIG. 6C is a first cross-sectional view through the barrel 200 shown in FIG. 6A along line C-C;

FIG. 6D is a right side-view of the barrel 200 shown in FIG. 6A;

FIG. 6E is a second cross-sectional view through the barrel 200 shown in FIG. 6A along line E-E;

FIG. 6F is a perspective view of the barrel 200;

FIG. 7A is a schematic drawing showing details of a top view of an assembly 300 of the needle 100 (shown collectively in FIGS. 5A-5F) and the barrel 200 (shown collectively in FIGS. 6A-6F), with the needle retracted into the barrel;

FIG. 7B is a left side view of the assembly 300 shown in FIG. 7A;

FIG. 7C is a right side view of the assembly 300 shown in FIG. 7A;

FIG. 7D is a cross-sectional view through the assembly 300 shown in FIG. 7A along line D-D;

FIG. 7E is a perspective view of the assembly 300;

FIG. 7F is an alternative perspective view of the assembly 300;

FIG. 8C is a perspective view of the cartridge slot 800a;

FIG. 9A is a schematic drawing showing details of a front view of a cartridge 600d fully inserted in the cartridge slot 800a (shown collectively in FIGS. 8A-8C), from a joint-diagnostic spectroscopic and biosensor meter according to an embodiment of the invention;

FIG. 9B is a cross-sectional view through the cartridge 600d and the cartridge slot 800a shown in FIG. 9A along line B-B;

FIG. 9C is a perspective view of the cartridge 600d fully inserted in the cartridge slot 800a;

FIG. 12A is a schematic drawing showing details of a front view of a joint-diagnostic spectroscopic and biosensor meter 900 according to an embodiment of the invention;

FIG. 12B is a first cross-sectional view through the joint-diagnostic spectroscopic and biosensor meter 900 shown in FIG. 12A along line B-B;

FIG. 12C is a second cross-sectional view through the joint-diagnostic spectroscopic and biosensor meter 900 shown in FIG. 12A along line C-C;

FIG. 12D is a perspective view of the joint-diagnostic spectroscopic and biosensor meter 900;

FIG. 13A is a schematic drawing showing a top view of a spectroscopic and biosensor cartridge 600e, which can be used with a joint-diagnostic spectroscopic and biosensor meter according to an embodiment of the invention;

FIG. 13B is a first cross-sectional view through the spectroscopic and biosensor cartridge 600e shown in FIG. 13A along line B-B;

FIG. 13C is a second cross-sectional view through the spectroscopic and biosensor cartridge 600e shown in FIG. 13B along line C-C;

FIG. 14A is a schematic drawing showing a top view of a spectroscopic and biosensor cartridge 600f, which can be used with a joint-diagnostic spectroscopic and biosensor meter according to an embodiment of the invention;

FIG. 14B is a first cross-sectional view through the spectroscopic and biosensor cartridge 600f shown in FIG. 14A along line B-B;

FIG. 14C is a second cross-sectional view through the spectroscopic and biosensor cartridge 600f shown in FIG. 14B along line C-C;

FIG. 14D is a third cross-sectional view through the spectroscopic and biosensor cartridge 600f shown in FIG. 14A along line D-D;

FIG. 14E is a fourth cross-sectional view through the spectroscopic and biosensor cartridge 600f shown in FIG. 14A along line E-E;

FIG. 15A is a schematic drawing showing the bottom view of a spectroscopic and biosensor cartridge (600f, shown collectively in FIGS. 14A-14E) and cap (960) assembly 600g, that can be used with a joint-diagnostic spectroscopic and biosensor meter according to an embodiment of the invention;

FIG. 15B is a first cross-sectional view through the spectroscopic and biosensor cartridge and cap assembly 600g shown in FIG. 15A along line B-B;

FIG. 15C is a second cross-sectional view through the spectroscopic and biosensor cartridge and cap assembly 600g shown in FIG. 15A along line C-C;

FIG. 16A is a schematic drawing showing a top view of a spectroscopic and biosensor whole blood and plasma cartridge 600h that can be used with a joint-diagnostic spectroscopic and biosensor meter according to an embodiment of the invention;

FIG. 16B is a first cross-sectional view through the spectroscopic and biosensor whole blood and plasma cartridge 600h shown in FIG. 16A along line B-B;

FIG. 16C is a second cross-sectional view through the spectroscopic and biosensor whole blood and plasma cartridge 600h shown in FIG. 16B along line C-C;

FIG. 17A is a schematic drawing showing a top view of a spectroscopic and biosensor whole blood and plasma cartridge 600k that can be used with a joint-diagnostic spectroscopic and biosensor meter according to an embodiment of the invention;

FIG. 17B is a first cross-sectional view through the spectroscopic and biosensor whole blood and plasma cartridge 600k shown in FIG. 17A along line B-B;

FIG. 17C is a second cross-sectional view through the spectroscopic and biosensor whole blood and plasma cartridge 600k shown in FIG. 17A along line C-C;

FIG. 17D is a third cross-sectional view through the spectroscopic and biosensor whole blood and plasma cartridge 600k shown in FIG. 17B along line D-D;

FIG. 18A is a schematic drawing showing a top view of a spectroscopic and biosensor whole blood and plasma cartridge 600m that can be used with a joint-diagnostic spectroscopic and biosensor meter according to an embodiment of the invention;

FIG. 18B is a first cross-sectional view through the spectroscopic and biosensor whole blood and plasma cartridge 600m shown in FIG. 18A along line B-B;

FIG. 18C is a second cross-sectional view through the spectroscopic and biosensor whole blood and plasma cartridge 600m shown in FIG. 18B along line C-C;

FIG. 18D is a third cross-sectional view through the spectroscopic and biosensor whole blood and plasma cartridge 600m shown in FIG. 18A along line D-D;

FIG. 18E is a detailed view of the detail E shown in FIG. 18D;

FIG. 19A is a schematic drawing showing a top view of a spectroscopic and biosensor whole blood and plasma cartridge 600n that can be used with a joint-diagnostic spectroscopic and biosensor meter according to an embodiment of the invention;

FIG. 19B is a first cross-sectional view through the spectroscopic and biosensor whole blood and plasma cartridge 600n shown in FIG. 19A along line B-B;

FIG. 19C is a second cross-sectional view through the spectroscopic and biosensor whole blood and plasma cartridge 600n shown in FIG. 19A along line C-C;

FIG. 19D is a third cross-sectional view through the spectroscopic and biosensor whole blood and plasma cartridge 600n shown in FIG. 19B along line D-D;

FIG. 20A is schematic drawing showing details of a hollow fiber filter bundle 660b shown in cartridge 600n (shown collectively in FIGS. 19A-19D);

FIG. 20B is a perspective view of the hollow fiber filter bundle 660b shown in FIG. 20A;

FIG. 20C is an alternative perspective view of the hollow fiber filter bundle 660b shown in FIG. 20A;

FIG. 20D is a cross-sectional view through the hollow fiber filter bundle 660b shown in FIG. 20A along line D-D;

FIG. 20E is a detailed view of detail E shown in FIG. 20D;

FIG. 21A is a schematic drawing showing details of a top view of a spectroscopic and biosensor cartridge 600p, that can be used with a joint-diagnostic spectroscopic and biosensor meter according to an embodiment of the invention;

FIG. 21B is a first cross-sectional view through the spectroscopic and biosensor cartridge 600p shown in FIG. 21A along line B-B;

FIG. 21C is a second cross-sectional view through the spectroscopic and biosensor cartridge 600p shown in FIG. 21A along line C-C;

FIG. 21D is a third cross-sectional view through the spectroscopic and biosensor cartridge 600p shown in FIG. 21B along line D-D;

FIG. 22A is a schematic drawing showing details of a top view of a spectroscopic and biosensor cartridge (600s) and cap (960) assembly 600v, that can be used with a joint-diagnostic spectroscopic and biosensor meter according to an embodiment of the invention;

FIG. 22B is a first cross-sectional view through the spectroscopic and biosensor cartridge and cap assembly 600v shown in FIG. 22A along line B-B;

FIG. 22C is a second cross-sectional view through the spectroscopic and biosensor cartridge and cap assembly 600v shown in FIG. 22A along line C-C;

FIG. 22D is a third cross-sectional view through the spectroscopic and biosensor cartridge and cap assembly 600v shown in FIG. 22C along line D-D;

FIG. 23A is a schematic drawing showing details of a top view of a spectroscopic and biosensor cartridge 600w, that can be used with a joint-diagnostic spectroscopic and biosensor meter according to an embodiment of the invention;

FIG. 23B is a first cross-sectional view through the spectroscopic and biosensor cartridge 600w shown in FIG. 23A along line B-B; and FIG. 23C is a second cross-sectional view through the spectroscopic and biosensor cartridge 600w shown in FIG. 23B along line C-C.

DETAILED DESCRIPTION OF PREFERRED ASPECTS OF THE INVENTION

Figure 8C:
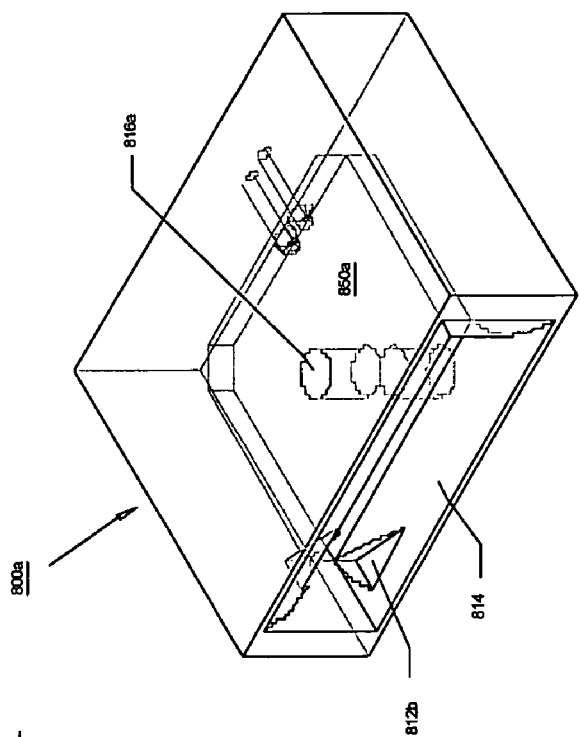

Some embodiments of the invention provide a joint-diagnostic spectroscopic and biosensor meter for analyzing at least one fluid sample confined to a disposable microfluidic cartridge, and some embodiments of the invention provide alternative designs of the disposable cartridge. The cartridges comprise: one or more than one flow path; one or more than one optical chamber; one or more than one biosensor chamber, with a biosensor chamber housing one or more than one biosensor, and one or more than one electrical output contact, with each biosensor in electrical communication with an electrical output contact, so that the electrical output contact can at least receive electrical signals from the biosensor. A flow path is a path that can be traced out by the flow of the fluid sample. As an example, the flow path sometimes begins at the sample inlet opening and sometimes terminates at a vent, which is used to relieve air pressure in the flow path. Sometimes the flow path terminates in a vacuum chamber, with means for generating negative pressure within the vacuum chamber, which is used to relieve air pressure in the flow path, promote flow along the flow path, or both. Several examples of cartridges will be shown, as examples of various combinations of features, and although some of the examples are specific schematic cartridge illustrations, the examples are not intended to limit the scope of the invention in any way. When the fluid samples are: whole blood, and plasma derived from the whole blood, the cartridge comprises at least two flow paths, the two flow paths being referred to as a whole blood flow path and a plasma flow path. In some embodiments comprising more that one whole blood flow path, the flow paths are sometimes referred to as a biosensor flow path, and a spectroscopic flow path, for clarity.

It should be understood that the term analyzing a sample may also be referred to as testing a sample or measuring a sample.

Some embodiments of the meter include the following:
a) a meter housing;
b) a power supply, which is preferably in the form of rechargeable batteries;
c) a source of electromagnetic radiation (EMR);
d) a slot in the meter housing for receiving the cartridge, the slot having an electrical input contact for mating with the electrical output contact of the cartridge when the cartridge is inserted into the slot. When the electrical input contact mates with the electrical output contact of the cartridge, the optical chamber becomes positioned to receive the EMR from the source;

e) a photodetector for measuring EMR transmitted through or reflected from the fluid sample within the optical chamber and for providing an EMR-based signal derived from the EMR transmitted through or reflected from the fluid sample; and f) a processor in communication with the photodetector for receiving the EMR-based signal, and the input contact for receiving the sample biosensor data. The EMR-based signal is used to prepare a spectroscopic test result, and the sample biosensor data is used to prepare a biosensor test result.

When the electrical input contact mates with the output contact of the cartridge, the optical chamber becomes positioned to receive the EMR for spectroscopic measurement of the fluid sample. In an embodiment, the processor also comprises a spectroscopic control module (not shown) that is linked to the electrical input contact to receive a control signal from the electrical input contact when the electrical input contact mates with the electrical output contact of the cartridge. The control signal could be at least a signal derived from the electrical signal generated when either a calibration fluid comes in contact with the biosensor, or when the fluid sample comes in contact with the biosensor. The calibration fluid must have at least one known property for measurement by the biosensor. The control signal provides a control condition to the spectroscopic control module, for initiating spectroscopic measurement. Alternatively, a control condition comprises receiving a control signal through a limit switch housed within the meter slot, wherein the limit switch becomes activated after the electrical input contact mates with the electrical output contact of the cartridge.

A disposable cartridge adapted for insertion into the meter for providing EMR-based signal and sample biosensor data from a fluid sample confined to the disposable cartridge, provide test results based on the EMR-based signal and the sample biosensor data. Some embodiments of a the cartridge include the following:

a) a cartridge housing;

b) an inlet opening in the cartridge housing for receiving the fluid sample;

c) one or more than one flow path within the cartridge housing for receiving the fluid sample from the inlet opening, the one or more than one flow path comprising an optical chamber having at least one optical window for providing the EMR-based signal and a biosensor chamber having at least one biosensor for providing sample biosensor data;

d) at least one of an outlet vent or a negative pressure generating means for relieving pressure inside the one or more than one flow path, the negative pressure generating means comprising a compressible chamber, the negative pressure being generated inside the chamber by manually compressing and releasing the chamber.

In some embodiment of disposable cartridges, the biosensors require calibration prior to sample measurement, and some biosensors are pre-calibrated. Pre-calibration is usually performed for a lot or batch of cartridges, and a barcode on the cartridge could contain calibration information, which is read by a barcode reader that is linked to the processor. In the embodiments of disposable cartridges that require calibration prior to sample measurement, calibration of biosensors is performed by flooding the biosensor chamber with an appropriate calibration fluid stored in a sealed calibration reservoir or pouch. In an embodiment of the meter where calibration of the biosensor is required for the individual cartridge, prior to sample measurement, the meter also comprises a means for rupturing the calibration pouch and delivering the calibration fluid to the biosensor(s) in the biosensor chamber. Those skilled in the art will appreciate that the electrical signals generated from the biosensor after it comes in contact with a calibration fluid of know composition, and the known concentration of the analyte in the calibration fluid, can be used to generate a calibration algorithm for the analyte, and therefore for the sake of brevity, the mathematics involved in biosensor calibration will not be discussed here. The biosensor calibration requires mating of the electrical output contact of the cartridge and the electrical input contact of the meter slot.

Depending on the design of the disposable microfluidic cartridge, as will be seen from the examples described later in details, the sample can enter the cartridge for measurement by any of the following means, or combination thereof: a) a negative pressure, for example, by squeezing and releasing a compressible chamber located at the end of the flow path; b) capillary action; c) positive pressure from the plunger in a syringe containing the sample; and d) positive pressure from a blood vessel. Positive pressure from a blood vessel is particularly useful when the inlet opening of the cartridge is a sharp open end of a needle, illustrated collectively in FIGS. 4A-4C, as a non-limiting example. The positive pressure is usually applied at the inlet opening of the cartridge.

Some embodiments of the cartridge, capillary breaks are provided along the flow path at strategic locations, for retaining the calibration fluid in the biosensor chamber. Sometimes a capillary break, located along the flow path between the inlet opening and the biosensor chamber, is used to retain the fluid sample away from the biosensor, prior to sample measurement. A capillary break is defined as an expansion in the flow path, which makes the flow path too large at the point of expansion to maintain fluid flow by capillary action. In some embodiments, where flow does not depend on capillary action, references are still made to capillary breaks. In such cases, the structure referred to as a capillary break, is simply an expansion in the flow path that functions as a buffer chamber for collecting excess fluid. After biosensor calibration, the fluid sample is used to flush out the calibration fluid from the biosensor chamber, and bring the fluid sample in contact with the biosensor. In an embodiment of the cartridge, illustrated collectively in FIGS. 13A-13C, blood from a syringe is forced into the cartridge, across the capillary breaks (920a and 920b) at the biosensor chamber, displacing the calibration fluid and filling the biosensor chamber with blood instead of calibration fluid. In another embodiment of the cartridge, illustrated collectively in FIGS. 14A-14E and FIGS. 15A-15C, there is provided, a sample retention chamber (670 and 642 combined) between the capillary break 920a and the inlet opening 612, a flexible air chamber 940 in the cartridge housing, a conduit 942 for connecting the air chamber to the sample retention chamber, a cap 960 for sealing the inlet opening 612 of the cartridge, and a means for sealing (not shown in the system) the spectroscopic vent 137a. As an example, the meter could carry a spring-loaded ball in the meter slot, which forcibly seats in the spectroscopic vent 137a after the cartridge is properly inserted in the meter slot, sealing the vent. Once all openings to the atmosphere in the housing of the cartridge, except the biosensor vent (shown as 137b in FIG. 14C) are sealed, the air chamber is depressed by some means in the system, forcing air out of the air chamber 940, into the conduit 942 connected to the sample retention chamber, and the air forces the sample from the sample retention chamber (in this example, the conduit is joined at the inlet chamber 670) into the biosensor chamber for sample measurement.

Before the cartridge is inserted in the meter slot, the fluid sample could already be inside the cartridge, but not in contact with the biosensor.

Some embodiments of the cartridge (for example cartridge 600e illustrated collectively in FIGS. 13A-13C), allow the sample to be injected into the cartridge after the biosensor is calibrated in the meter, either while the cartridge is inserted in the meter slot, or by having to remove the empty cartridge (i.e., without sample) after biosensor calibration, and reinsert the cartridge into the meter slot after filling the cartridge with sample. In the embodiment where the fluid sample is injected into the cartridge from a syringe, the air chamber is not essential because the force required to push the fluid sample is generated by advancing the syringe plunger. Many of these steps could be performed automatically under the control of the meter, and any manual steps could be performed by following instructions on the display screen of the meter.

In the specific embodiments of the invention, all the sample flow paths are restricted within the microfluidic cartridges and therefore, there is no pump or fluid lines connecting the microfluidic cartridges to the meter, which are usually seen in CO-oximeters and blood-gas instruments. Moreover, there is no permanent installation of a cartridge in the meter, as is the case with some CO-oximeters and blood-gas instruments, and the cartridges of the present invention are designed for single use.

When a cartridge is inserted properly in the slot of the meter, the electrical output contact of the cartridge mates with the electrical input contact of the meter slot, bringing the optical chamber of the cartridge in position to receive EMR from the EMR source. Those skilled in the art will appreciate that the EMR could also be channeled to the optical chamber by optical fibers. The EMR transmitted through the fluid sample in the cartridge, or reflected from the fluid sample, impinges upon a photodetector within the meter. Calibration algorithms for spectroscopic measurements are preferably installed within the processor of the meter, for transforming the spectroscopic signals into analyte measurements. Calibration algorithms for biosensor measurements are preferably installed within the processor of the meter, for transforming the biosensor signals into analyte measurements, but some biosensors require calibration prior to sample measurement. The measurements are usually in concentration units, but those skilled in the art will appreciate that other parameters can be measured, for example without limitations, the ratio of the concentrations of two different analytes.

Those skilled in the art will appreciate the various ways a spectroscopic measurement instrument can be constructed, and various elements that make up such instruments. Accordingly, for the sake of brevity, description of basic spectroscopy and a list and function of the elements that make up a spectroscopic apparatus will not be discussed here. However, it should be noted that a joint-diagnostic spectroscopic and biosensor meter according to the invention, requires at least one source of EMR, and the preferred source of EMR is a tungsten lamp, but without limitation, the source of EMR may be one or more than one Light Emitting Diode (LED), or one or more than one laser, or combination thereof. Those skilled in the art will appreciate that when the source of EMR is a single source, the single source could be split by a multichannel optical fiber for providing more than one light path.

With respect to the detection system, the preferred detector is an array of photodiodes, but those skilled in the art will appreciate that a single photodiode or one or more than one charged coupled detector (CCD) can be used.

With respect to spectroscopic measurements, the examples shown describe an apparatus that operates in transmission mode. Those skilled in the art will appreciate that the spectroscopic apparatus of a joint-diagnostic spectroscopic and biosensor meter can also operate in reflectance mode by placing a reflecting member in the cartridge slot, on one side of the optical chamber 616a (FIG. 1B and FIG. 9B), such that the EMR transmitted through the sample would be reflected off the reflecting member, and the reflected EMR would enter the sample for the second time. Examples of cartridge slots are shown schematically as 800a in FIG. 8C, 800a in FIG. 9C, 800b in FIGS. 10C and 800c in FIG. 11C and FIGS. 12B & C. In a diagnostic measurement instrument operating in the reflectance mode, both the EMR source and the photodetector would be on the same side of the optical chamber 616a (FIG. 1B and FIG. 9B). Moreover, those skilled in the art will also appreciate that instead of installing a reflecting member around the slot in the housing of the meter, one side of the wall-portions (624a or 624b, FIG. 1A) of the optical chamber 616a (FIG. 1B and FIG. 9B) could be coated with a reflecting material.

In some embodiments, the joint-diagnostic spectroscopic and biosensor meter further comprises a display screen for viewing the results and aiding the operator in use of the meter, as well as buttons for manipulating the display function. Those skilled in the art will appreciate that the meter could be connected to a host computer. Therefore, some embodiments of the system also comprise at least one communication port for interfacing with other instruments. Other non-limiting examples of other instruments are a printer, and diagnostic testing instruments like a pulse oximeter or some other non-invasive testing instrument. The optional communication port is also used to upgrade information in the meter's processor, as well as to download information from the meter's processor. Another optional port in the housing of some embodiments of the joint-diagnostic spectroscopic and biosensor meter is provided for charging the power supply within the meter. Those skilled in the art will appreciate that a single port can be used for both data transfer and a power supply, for example without any limitation, a USB (Universal Serial Bus) port.

Some embodiments of the joint-diagnostic spectroscopic and biosensor meter comprise one photodetector (photodiode), or more than one photodetector assembled as an array of detectors in a spectrometer, wherein the spectrometer comprises a grating for dispersing EMR emerging from the fluid sample, into wavelength components. The meter optionally comprises a focusing lens between the disposable cartridge and the spectrometer, show as 870 in FIGS. 11a & 11c and FIGS. 12A & 12C.

Some embodiments of disposable cartridges are shown with vents for relieving pressure inside the flow paths, or facilitating airflow out of the flow paths. Other embodiments of cartridges will be shown, where there are no vents for facilitating airflow out of the flow path. Instead of the vent, the housing of the cartridge includes a vacuum chamber (a compressible chamber) located at the end of the flow path, replacing the vent(s), and means for generating negative pressure within the vacuum chamber. There can be one or more than one vacuum chamber, for regulating flow of fluids. In some embodiments, the vacuum chamber is of particular use in plasma extraction from whole blood. Those skilled in the art will appreciate that other embodiments of cartridges can operate with a combination of at least one vent and at least one vacuum chamber.

Although the examples of cartridges illustrate separate flow paths for the optical chamber and the biosensor chamber, those skilled in the art will appreciate that a microfluidic cartridge can comprise an optical chamber and a biosensor chamber in series along a single flow path, with the biosensor chamber positioned either before or after the optical chamber. An example of a cartridge comprising a single flow path is illustrated collectively in FIGS. 23A-23C.

In some embodiments, the interior walls of the cartridges are treated with a hydrophillic coating to promote even spreading of the blood within the optical chamber, and to promote movement of blood along the flow path.

The optical chamber is located along a flow path, and the optical chamber has at least one optical window for spectroscopic analysis of the fluid sample. The fluid sample could also be an extract of the fluid sample, for example which should not be considered limiting in any way, plasma extracted from the whole blood by a flow-through filtration (or plasma extraction) system within a specific embodiment of the disposable microfluidic cartridge, illustrated collectively in FIGS. 2A-2E and FIGS. 3A-3G. Optionally, the disposable microfluidic cartridges contain more than one flow path, and more than one optical chamber in one or more than one flow path. A flow path may also contain one or more reagents, anywhere along the flow path, for example without limitation, an anticoagulant, a hemolyzing reagent, or a reagent that reacts with an analyte to enhance the absorbance of EMR. In a preferred embodiment, the optical chamber is specifically designed to reduce the average attenuation of EMR due to scattering of EMR by the red blood cells in a blood sample, without having to hemolyze the red blood cells using sound waves or hemolyzing chemicals. Preferably the depth of the optical chamber, i.e., the internal distance between the optical windows, is about 0.1 mm, but those skilled in the art will appreciate that the depth of the optical chamber is preferably larger for plasma. An average depth of an optical chamber is in an approximate range of about 0.02 mm to about 5 mm.

The biosensor chamber is located along a flow path, and the biosensor chamber may have one or more than one biosensor for analyzing the fluid sample. Optionally, the disposable cartridge contains more than one biosensor chamber as illustrated in FIG. 2E, identified as 672 (a plasma biosensor chamber) and 674 (a whole blood biosensor chamber). A flow path that includes a biosensor chamber is specifically designed with at least one active surface of the biosensor exposed to the fluid sample. Those skilled in the art will appreciate that biosensors may include various transducer arrangements that convert at least one property of the fluid sample into an electrical signal, wherein the transducer comprises at least one active surface for contacting the fluid sample. The at least one active surface is one of a chemical sensitive surface, or an ionic sensitive surface, and wherein the at least one biosensor comprises at least one of a transistor, an ion-selective membrane, a membrane-bound enzyme, a membrane-bound antigen, a membrane-bound antibody, or a membrane-bound strand of nucleic acid. The disposable cartridge also comprises at least one electrical output contact, and the cartridge slot of the meter also comprises at least one electrical input contact, wherein the electrical output contact mates with the electrical input contact after the disposable cartridge is properly inserted into the slot, as illustrated collectively in FIGS. 9A-9C. Although the example illustrated collectively in FIGS. 9A-9C shows the cartridge electrical output contact in a female configuration, and also shows the meter slot electrical input contact in a male configuration, those skilled in the art will appreciate that the electrical output contacts can mate with the electrical input contacts in other ways.

In a specific embodiment of a disposable cartridge illustrated collectively in FIGS. 2A-2E, the cartridge contains a flow-through filtration chamber, which comprises a hollow fiber filter bundle 660a. More details on plasma extraction are disclosed in Canadian Patent Application No. 2,507,323 (Samsoondar, the entire contents of which are incorporated herein by reference). Details of the hollow fiber filter bundle 660a are illustrated collectively in FIGS. 3A-3G. The hollow fiber filters may run in parallel with the flow path within the filtration chamber, as illustrated as 660b in FIGS. 19C & D, but in a preferred embodiment, illustrated as 660a in FIG. 2E and FIG. 17D, for example, the hollow fiber filters in the bundle 660a run approximately perpendicular to the whole blood flow path.

In some embodiments, the inlet chamber 670 of the disposable cartridge illustrated collectively in FIGS. 2A-2E and FIGS. 9A-9C is dimensioned to accommodate a male end of a traditional syringe. In other embodiments, the inlet of the cartridge is also dimensioned to resemble the end of a capillary tubing, illustrated collectively in FIGS. 1A-1C as 672a, to receive the fluid sample from a pin prick drop of blood. As an alternative, the inlet of the disposable cartridge is the sharp end 147 of a needle, as illustrated collectively in FIGS. 4A-4C. The needle is allowed to enter the lumen of a blood vessel for receiving the blood directly into the disposable cartridge, eliminating the need of a syringe. The sharp end 147 of the needle 100 is preferably encased in a moveable barrel 200, illustrated collectively in FIGS. 6A-6F, for sheathing and unsheathing the sharp end, to protect the user from accidental injury. An example of a needle, barrel, and the assembly of the two, which should not be considered limiting in any way, are illustrated collectively in FIGS. 5A-5F, FIGS. 6A-6F and FIGS. 7A-7F respectively. Other embodiments of similar needles are disclosed in Canadian Patent Application No. 2,517,299 (Samsoondar, the entire contents of which are incorporated herein by reference). The outlet 171 of the needle assembly 300, illustrated collectively in FIGS. 7A-7F, mates with the inlet 670 of the cartridges illustrated collectively in FIGS. 2A-2E and FIGS. 9A-9C, eliminating the need of a syringe. The cartridge could be inserted into the meter slot, with the needle still attached. As another alternative, as illustrated collectively in FIGS. 23A-23C, the inlet opening 670 is flared so that the inlet opening 612 can be placed over a pin prick, either before or after the drop of blood develops. The blood is then allowed to freely flow into the cartridge. The flow may be assisted by some squeezing of the body part around the pin prick. It is well known that excessive squeezing, commonly referred to as milking, should be avoided if contamination of the blood with interstitial fluid compromises the accuracy of the analyte measurement.

When an arterial blood sample is tested, the arterial blood is usually collected in a traditional syringe. After the blood is collected, the syringe needle must be removed and the end of the syringe must be capped immediately to avoid atmospheric contamination. The arterial blood in the syringe is usually transferred in ice to a central laboratory for testing. Prior to testing, the capped syringe must be uncapped before the sample is injected or aspirated into the measurement instrument. The delays, potential for air bubbles becoming trapped in the blood, the exposure of the healthcare provider to blood, and the risk of infection through accidental needle stick, are all disadvantages in the current system. A further disadvantage is that when the plunger of the syringe is pulled too forcefully, turbulence in the blood flow can cause air bubbles to develop in the blood. Moreover, the smaller the bore or lumen of the needle, the greater the potential for hemolysis to occur. This limits the minimum thickness of the needle; the smallest (thinnest) needle is preferred to minimize pain experienced by the patient during an arterial puncture. Also, because of the dead space inside a traditional syringe, a minimum of about half to one milliliter of blood must be drawn, even though the volume of blood required by the cartridge could be much less. The aforementioned disadvantages are minimized with the use of the needle like for example, the one collectively illustrated in FIGS. 7A-7F. Some embodiments of cartridges illustrated as examples, will allow the use of an arterialized capillary blood sample, instead of an arterial blood sample. This aspect of the invention is especially useful for blood gas and co-oximetry measurements in babies.

In some embodiment of a microfluidic cartridge, illustrated collectively in FIGS. 4A-4C, there is provided an integrated cartridge and needle 600c. The barrel 200 illustrated collectively in FIGS. 6A-6F is not shown. The integrated cartridge and needle 600c is a safer and more convenient alternative, to assembling a cartridge (shown collectively as FIGS. 2A-2E) and a needle (shown collectively as FIGS. 5A-5F) before use.

Some embodiment of a joint-diagnostic spectroscopic and biosensor meter optionally comprises a barcode reader for reading a barcode on the disposable cartridge (not shown), the barcode containing at least information regarding calibration of a biosensor. The barcode also optionally contains information about the joint-diagnostic spectroscopic and biosensor meter. Alternatively, the disposable cartridge further comprises a calibration pouch 928 (illustrated in FIGS. 13B, 13C, 15B, 22B & 22D), containing a calibration fluid, that is arranged in fluid connection with the at least one biosensor chamber, after the calibration pouch is ruptured. For cartridges with calibration pouches, the joint-diagnostic spectroscopic and biosensor meter further comprises a means for rupturing the calibration pouches, for example, which should not be considered limiting in any way, a rotating cam, or a reciprocating plunger. In some embodiments, the pouch cavity 924, illustrated in FIG. 14C, contains a projection (not shown), which ruptures the calibration pouch when pressure is applied to a flexible member at the surface of the calibration pouch, shown as 930. In some embodiments, a portion of the wall of the calibration pouch is weakened by design, for easy rupture after pressure is applied.

As mentioned previously, some embodiment of a disposable cartridge for use with a joint-diagnostic spectroscopic and biosensor meter comprises a flow-through filtration chamber for extracting plasma from whole blood, and further comprises a first optical chamber along a whole blood flow path, and a second optical chamber along the plasma flow path. In an embodiment illustrated in FIG. 16A, the distance from the first optical chamber to its adjacent edge (A) of the disposable cartridge, is approximately equal to the distance from the second optical chamber to its adjacent edge (B) of the disposable cartridge. An embodiment of a meter that operates with such a cartridge is provided with at least one source of EMR and at least one light path. For the embodiment of a meter that provides a single light path, the single light path travels through the first optical chamber when the disposable cartridge is inserted properly in a first orientation. When the disposable cartridge is inserted properly in a second orientation, the second orientation being 180 degrees to the first orientation, the single light path travels through the second optical chamber. Therefore, the plasma and the whole blood can be measured sequentially using the same light path. Because of the absorbance signals for whole blood and plasma are significantly different, the software in the meter could discriminate whole blood from plasma. Those skilled in the art will appreciate that there are other methods of analyzing the plasma and whole blood using a single light path, for example, a prompt in the display screen could provide appropriate instructions for cartridge insertion.

In embodiments of the cartridges shown as examples and in the relevant incorporated references, the optical chamber (e.g., 616a, FIG. 1B) is designed to spread blood into a thin film, thereby reducing the incidences of trapped air bubbles in the blood sample in the optical chamber. Instead, air bubbles are pushed through the optical chamber and guided out of the apparatus through a vent (e.g., 137a, FIG. 1B). In the same embodiments, the second flow path includes at least one biosensor (e.g., 652a, FIG. 1B). The optical chamber could provide spectroscopic blood measurements for determination of, for example without limitation, Hb species, and the biosensor could provide blood measurements for determination of, for example without limitation, blood pH. The apparatus is particularly useful for a combination of blood gas and co-oximetry measurement.

Moreover, in these embodiments blood within the optical chamber is further isolated from contamination by room air by providing an inlet transition chamber (e.g., 614a, FIG. 1B) and an overflow chamber (e.g., 618a, FIG. 1B) at a respective entrance and exit of the optical chamber. In use, blood in the inlet transition chamber and the overflow chamber serve as barriers between blood in the optical chamber and room air, thereby isolating the blood in the optical chamber from oxygen contamination. In the rare incident of a trapped air bubble, those skilled in the art will appreciate that various calibration algorithms for many specific analytes measured in the blood sample can be developed that could compensate for measurement inaccuracies caused by trapped air bubbles, except for those analytes such as the partial pressure of oxygen and oxy-hemoglobin, which become falsely elevated as a result of oxygen introduced into the blood sample from the air bubble. Similarly in the same embodiments, the biosensor chamber (e.g., 674, FIG. 1B) is also isolated from contamination by room air by providing an inlet transition chamber (e.g., 642, FIG. 1B) and an overflow chamber (e.g., 620b, FIG. 1B) at a respective entrance and exit of the biosensor chamber 674. Those skilled in the art will appreciate that a microfluidic cartridge could comprise an optical chamber and a biosensor in series along a single flow path, with the biosensor positioned either before or after the optical chamber. As an example, a cartridge with a single flow path is illustrated collectively in FIGS. 23A-23C. The overflow chamber 618a of the optical chamber 616a serves as the inlet transition chamber of the biosensor chamber 674. In some embodiments (not shown), the overflow chamber of the biosensor chamber serves as the inlet transition chamber of the optical chamber.

Optionally the microfluidic cartridges also include at least one visible fill line or indicator serving as a marker providing a user with a visual indicator relating to the sufficiency of the blood sample in the optical chamber and biosensor chamber. In some embodiments, the visible fill line is located in a position between the overflow chamber and the capillary break, and is indicative of whether or not a volume of blood drawn into the cartridge is present in sufficient amount to: i) ensure that the blood in the optical chamber and biosensor chamber is substantially free from contaminants that may have been introduced during the filling of the apparatus with blood; and/or, ii) ensure that there is an effective amount of blood surrounding the optical chamber and biosensor chamber to isolate the blood in the optical chamber and biosensor chamber from room air. As examples, visible fill lines 621a and 621b (with instructions) are shown in the cartridge embodiments illustrated in FIGS. 13A and 23A. As a third example, a single visible fill line 621c (with instructions) is shown in the cartridge embodiment illustrated in FIG. 21A.

Referring collectively to FIGS. 1A-1C, shown are schematic drawings illustrating details of a disposable cartridge 600a, suitable for use with a joint-diagnostic spectroscopic and biosensor meter. Other embodiments of cartridges like 600a will be shown, which can be used with a meter like the meter shown collectively in FIGS. 12A-12D, for example, for providing both spectroscopic and biosensor measurements of a fluid sample. Also shown collectively in FIGS. 1A-1C, are schematic drawings of a cartridge 600a suitable for attachment to a needle via the internal threads in a female receptor of a needle (not shown), and the matching threads in the inlet tubing 672a (FIG. 1A and FIG. 1B). The embodiment of the needle is similar to the needle assembly shown collectively in FIGS. 7A-7F except that the needle outlet 137 comprises internal threads that are complimentary to the threads on the inlet tubing 672a (FIGS. 1A &B). Optionally, blood from a pin prick could be drawn directly into the cartridge by capillary action by inserting the inlet opening 612 into the drop of blood. Referring to FIG. 1A, shown is a side view of the housing 123 of cartridge 600a, with inlet opening 612, and an electrical output contact 654a in electrical connection with the biosensor 652a (shown in FIG. 1B), and with optical wall-portions 624a and 624b. Referring to FIG. 1C, shown is a perspective view of the cartridge 600a, with the inlet opening 612 and the optical wall portion 624a.

Referring to FIG. 1B, shown is a cross-sectional view through the cartridge 600a shown in FIG. 1A along line B-B showing the sample inlet opening 612 and the threaded inlet tubing 672a. As already mentioned, capillary blood obtained from a pinprick could be allowed to flow into the cartridge 600a through the inlet 612, arriving at the manifold 640 via the inlet chamber 670; from the manifold 640, the blood is distributed into the two independent flow paths, which begin at the manifold 640: the first flow path, referred to as the whole blood biosensor flow path, includes in series, the biosensor inlet transition chamber 642, the biosensor chamber 674, the biosensor outflow chamber (or a combined overflow and outflow chamber) 620b, the biosensor capillary break 622b, and terminating at the biosensor vent 137b, with a conduit 135b which is not essential, but it provides some distance between the vent 137b and the capillary break 622b; the second flow path, referred to as the whole blood spectroscopic flow path, which also begins at the manifold 640, includes in series, the spectroscopic inlet transition chamber 614a, the optical chamber 616a, the spectroscopic overflow chamber 618a, the spectroscopic outflow chamber 620a, the spectroscopic capillary break 622a, and terminating at the spectroscopic vent 137a via the conduit 135a. It should be understood that both the overflow chamber 618a and the outflow chamber 620a could be considered as a single chamber, as was alluded to previously regarding the biosensor overflow chamber 620b. Two biosensors are shown as 652a and 652b, which are connected to their respective electrical output contacts 654a and 654b, through respective electrical conductors 676a and 676b.

Referring collectively to FIGS. 2A-2E, shown are schematic drawings illustrating details of the measurement cartridge 600b. The cartridge 600b is capable of extracting or filtering plasma from whole blood, and the measurement technology includes spectroscopy with the optional use of one or more than one reagent, and biosensors. Referring to FIG. 2A is a bottom view of the housing 123 of the disposable cartridge 600b showing the sample inlet opening 612, the inlet chamber 670, a whole blood optical chamber wall-portion 624a, and a plasma optical chamber wall-portion 626a. The cartridge 600b contain three flow paths illustrated in FIG. 2E.

Referring to FIG. 2B, shown is a first cross-sectional view through cartridge 600b illustrated in FIG. 2A along line B-B, showing parts identified later in FIG. 2E.

Referring to FIG. 2C, shown is a second cross-sectional view through cartridge 600b illustrated in FIG. 2A along line C-C, showing parts identified later in FIG. 2E. In addition, shown are the conduits 135a, 135b and 135c which connect the capillary breaks 622a, 622b and 622c respectively, with the respective vents 137a, 137b and 137c.

Referring to FIG. 2D, shown is a third cross-sectional view through cartridge 600b illustrated in FIG. 2A along line D-D, showing parts identified later in FIG. 2E. In addition, shown are the blood optical wall portions 624a and 624b. For convenience and as deemed appropriate, same reference numerals are used as those used for the disposable microfluidic cartridge illustrated collectively in FIGS. 1A-1C, and the reference numerals will also be used for other embodiments as deemed appropriate.

Referring to FIG. 2E, shown is a fourth cross-sectional view through cartridge 600b illustrated in FIG. 2D along line E-E. The cartridge can be filled with blood from a traditional syringe, after the male end of the syringe is inserted through the inlet opening 612, into the inlet chamber 670. Alternatively, the male end 171 of the needle 100 illustrated collectively in FIGS. 5A-5F is first fitted into the cartridge inlet opening 670. Then the sharp open end 147 of the needle is inserted into a blood vessel, allowing the blood to flow into the cartridge 600b. The needle 100 assembled with a safety barrel 200 (shown collectively in FIGS. 6A-6F) is also shown collectively in FIGS. 7A-7F as 300. Whether a traditional syringe or the needle illustrated collectively in FIGS. 5A-5F and FIGS. 7A-7F is used, the blood arrives first at the manifold 640; from the manifold 640, the blood is distributed into two whole blood flow paths, which begin at the manifold 640: the first flow path includes in series, the whole blood biosensor inlet transition chamber 642, the whole blood biosensor chamber 674, the whole blood biosensor outflow chamber 620b, the whole blood biosensor capillary break 622b, and terminating at the whole blood biosensor vent 137b via a conduit 135b; the second flow path, which also begins at the manifold 640, includes in series, the whole blood spectroscopic inlet transition chamber 614a, the whole blood optical chamber 616a, the whole blood spectroscopic overflow chamber 618a, the flow-through filtration chamber 634 (for extracting plasma from the whole blood using the hollow fiber filter bundle 660a with closed flange 682 shown; details of 660a are shown collectively in FIGS. 3A-3G), the filtration chamber outflow 620a, the filtration chamber capillary break 622a, and terminating at the filtration chamber vent 137a via conduit 135a. Also shown in the second flow path is the spectroscopic overflow chamber 618a overlapping with the filtration chamber 634, which is the reason for not showing the spectroscopic overflow chamber 618a in the embodiment illustrated in FIG. 17D. A third flow path, defined as the plasma flow path, begins at the plasma collection chamber 636 (the plasma compartment of the filtration chamber 634, shown more clearly in the embodiment illustrated collectively in FIGS. 18A-18E), and includes in series the plasma biosensor chamber 672, the plasma spectroscopic inlet transition chamber 614b, the plasma optical chamber 616b, the plasma spectroscopic overflow chamber 618b, the plasma capillary break 622c, and terminating at the plasma vent 137c via a conduit 135c. A conduit 637 is also shown making fluid connection between the plasma biosensor chamber 672 and the plasma spectroscopic inlet transition chamber 614b. Those skilled in the art will appreciate that the conduit 637 can be considered to be a part of the plasma biosensor chamber 672. One plasma biosensor is shown as 652c, which is electrically connected through a medium or electrical conductor 676c to the biosensor electrical output contact 654c. Two whole blood biosensors are shown as 652a and 652b, which are connected to their respective biosensor electrical output contacts 654a and 654b, through respective electrical conductors 676a and 676b. In this embodiment of a disposable microfluidic cartridge, the force from a syringe plunger, or the arterial blood pressure, is essential for blood flow from the inlet opening 612 towards the blood vents 137a-b, and plasma filtration from the filtration chamber 634 towards the plasma vent 137c. In the embodiment of a disposable microfluidic cartridge shown collectively in FIGS. 1A-C, capillary action is essential for blood flow from the inlet opening 612 to the vents 137a-b. Other embodiments will be shown later, where the vents are replaced by one or more vacuum chambers, and the negative pressure created by the one or more vacuum chambers promotes blood flow and plasma filtration.

Referring collectively to FIGS. 3A-3G, shown are schematic drawings illustrating details of the hollow fiber filter bundle 660a shown inside the plasma filtration chamber 634 illustrated collectively in FIGS. 2A-2E. The hollow fiber filter bundle 660a comprises several hollow fiber filters, held together by two flanges 682 and 684.

Referring to FIG. 3A, shown is a top view of the hollow fiber filter bundle 660a, illustrating the perforated flange 684, and the closed flanged 682, and identifying a single hollow fiber 696.

Referring to FIG. 3B, shown is a left side view of the hollow fiber filter bundle 660a, illustrating the perforated flange 684, and identifying the lumen 692 of a single hollow fiber filter.

Referring to FIG. 3C, shown is a right side view of the hollow fiber filter bundle 660, illustrating the closed flange 682. The flanges 682 and 684, illustrates schematically that the blood can only flow through the filtration chamber 634, and no blood can enter the plasma collection chamber 636. Plasma filters into the lumen 692 of the hollow fiber filters, through the pores in the membrane 694. The filtration process is enhanced by, increased blood flow, increased size and number of pores in the membrane 694, decreased thickness of the membrane 694, and increased surface area of the membrane 694. Those skilled in the art will appreciate that these conditions have to become optimized, for example, if the flow is too forceful, hemolysis could occur, and if the pores are too large, red blood cells could enter the plasma chamber 636. It should be noted that the plasma chamber 636 actually begins in the lumen 692 of the hollow fiber filters. This compartmentalization of blood and plasma is better understood when the membrane 694 is flat, as illustrated collectively in FIGS. 18A-18E. It should be understood that although the hematocrit of the whole blood is altered after plasma filters through the membrane, the whole blood with the altered hematocrit is still referred to as whole blood.

Referring to FIG. 3D, shown is a cross-sectional view through the bundle 660a shown in FIG. 3A along line D-D, showing the closed flange 682, the cross-section of the single fiber 696, and detail F.

Referring to FIG. 3E, shown is a perspective view of the hollow fiber filter bundle 660a, showing a clear view of the perforated flange 684.

Referring to FIG. 3F, shown is a detailed view of the cross-section of a single hollow fiber, according to detail F identified in FIG. 3D, showing the lumen 692 of the fiber, and the wall of the fiber 694 (also referred to as a membrane).

Referring to FIG. 3G, shown is an alternative perspective view of the hollow fiber filter bundle 660a, showing a clear view of the closed flange 682. As an example, seven hollow fiber filters are shown inserted inside perforations in the flange 684 and sealed at the juncture of the hollow fiber and the flange 682. The wall 694 of the fiber is porous, with pores having an approximate distribution of pore diameters ranging from about 0.1 micrometer to about 10 micrometers, in some embodiments. In some embodiments, the internal diameter of the hollow fiber filters ranges approximately from about 0.1 mm to about 1 mm. Those skilled in the art will appreciate that blood flow decreases the viscosity of the blood and therefore enhances separation (or filtration, or extraction) of plasma from blood; extraction of plasma from blood also increases by, increasing the pore sizes of the membrane 694, decreasing thickness of the membrane 694, and increasing membrane 694 surface area. The surface area increases in proportion to the number of hollow fiber filters used.

The membrane 694 is a partition between the blood compartment, which is also identified as the filtration chamber 634, and the plasma compartment, which is identified as 636. In this embodiment of the invention, the plasma compartment includes the lumen 692 of the hollow fiber filters, and the blood compartment includes the exterior of the hollow fiber filters. A reversed design is illustrated collectively in FIGS. 19A-19D, where the blood compartment includes the lumen of the hollow fiber filters, both flanges identified as 684a and 684b collectively in FIGS. 20A-20E are perforated, and the plasma compartment includes the exterior of the hollow fiber filters. A third design is illustrated collectively in FIGS. 18A-18E, where the membrane 694 is not arranged as hollow fiber filters, but instead is a flat member erected as a partition between the blood compartment (which includes the chamber 634) and the plasma compartment (which includes the chamber 636a). These embodiments will be described in more details later.

Referring collectively to FIGS. 4A-4C, shown are schematic drawings illustrating details of an integrated needle and cartridge 600c.

Referring to FIG. 4A, shown is a schematic drawing illustrating a side view of an integrated needle and cartridge 600c, the hub of the needle 100 also comprising a cartridge 600b, similar to the cartridge identified as 600b and shown collectively in FIGS. 2A-2E.

FIG. 4B illustrates a cross-sectional view through the cartridge shown in FIG. 4A along line B-B, and showing parts already identified in FIG. 2E.

FIG. 4C is a perspective view of the integrated needle and cartridge 600c shown in FIG. 4A. Details of the cartridge 600b are already provided collectively with reference to FIGS. 2A-E, and further details of the needle 100, showing the sharp open end 147, are provided collectively in FIGS. 5A-5F and FIGS. 7A-7F. Details of the hollow fiber filter bundle identified as 660a are not shown. The integrated needle and cartridge eliminates the need for a traditional syringe.

Referring collectively to FIGS. 5A-5F, shown are schematic drawings illustrating details of a needle 100 that can be used with the cartridge 600b illustrated collectively in FIGS. 2A-2E and the cartridge 600d illustrated collectively in FIGS. 9A-9C.

Referring to FIG. 5A, shown is a schematic drawing illustrating a top view of the needle 100; FIG. 5B illustrates a left side view of the needle 100 shown in FIG. 5A; FIG. 5C illustrates a right side view of the needle shown in FIG. 5A; FIG. 5D illustrates a cross-sectional view through the needle 100 shown in FIG. 5A along line D-D; FIG. 5E illustrates a perspective view of the needle 100; and FIG. 5F illustrates an alternative perspective view of the needle 100. Those skilled in the art will appreciate that other suitable mating ends between needle and cartridge can be used, for example without limitations, threads as illustrated in capillary inlet tubing 672a of cartridge 600a shown in FIGS. 1A & B, and Luer lock mechanisms.

Still referring to FIGS. 5A-5F, the needle 100 comprises a shaft 143 and a hub with a front end 139 and a back end 123. It should be understood that the front end refers to a general area of the hub, and does not specifically identify any point or local area. Similarly, it should be understood that the back end refers to a general area of the hub, and does not specifically identify any point or local area. The shaft 143 has a sharp open end 147 and a second end, which is mounted in the passage 145 of the hub at the front end 123. The sharp open end 147 is usually the beveled end of the shaft, which is usually a hollow metal tube. The hollow portion of the shaft 143 is also referred to as the lumen (not shown). The bevel provides a point for piercing a blood vessel. Also shown collectively in FIG. 5A and FIG. 5F is the central axis 133a, which runs through the center of the shaft 143, along its length. The section of the shaft 143 mounted inside the hub is not shown. The passage 145 of the hub is fluidly connected to the lumen of the shaft, and a flow path is defined by the sharp open end 147, which leads into the lumen of the shaft 143, which leads into the passage 145 of the hub, and terminates at a blunt open end 137 of the hub. The blunt open end 137 is located at the back end 123 of the hub. The front end of the hub 139 contains external threads 173 for mating with complementary internal threads 175 in a barrel 200 illustrated collectively in FIGS. 6A-6F, and the blunt open end 137 is housed in a tapered projection 171, which resembles the male end of a syringe. In other embodiments of a needle 100, the blunt open end 137 is threaded with threads complementary to the threads in the inlet tubing 672a of a cartridge collectively illustrated in FIGS. 1A-1C. In an embodiment of a needle with a threaded open end 137, the tapered projection 171 is no longer necessary, since the mating end with the cartridge is the female opening 137, containing threads.

Referring collectively to FIGS. 6A-6F, shown are schematic drawings illustrating details of a barrel 200 for the needle 100 illustrated collectively in FIGS. 5A-5F.

Referring to FIG. 6A, shown is a schematic drawing illustrating a top view of the barrel 200; FIG. 6B illustrates a left side view of the barrel 200 shown in FIG. 6A; FIG. 6C illustrates a cross-sectional view through the barrel 200 shown in FIG. 6A along line C-C; FIG. 6D illustrates a right side view of the barrel 200 shown in FIG. 6A; FIG. 6E illustrates an alternative cross-sectional view through the barrel 200 shown in FIG. 6A along line E-E; and FIG. 6F illustrates a perspective view of the barrel 200.

Also illustrated collectively in FIGS. 6A-6F is: an opening 167 in the open anterior end (159) of the barrel 200, for movement of the needle shaft 143; an opening 165 in the open posterior end (161) of the barrel 200, for movement of the back end 123 of the needle hub shown in FIGS. 5A, E & F; and an axis 133b which runs through the center of the barrel, along the length of the barrel. The barrel 200 comprises an internal chamber 153 for housing the front end 139 of the hub shown in FIG. 5. The central axis 133a of the needle 100 and axis 133b of the barrel 200 are shown to be coaxial (illustrated in FIG. 7A), but the axes could also be parallel without being coaxial for example, if the outer design of the barrel is not cylindrical. Also shown collectively in FIGS. 6A-6F are internal threads 175. In this particular embodiment of the barrel 200, the threads 175 do not run continuously throughout the length of the barrel, and prevents the front end 139 of the needle hub from moving beyond the threaded area in the barrel 200.

Referring collectively to FIGS. 7A-7F, shown are schematic drawings illustrating details of a needle (100) and barrel (200) assembly 300 with the needle shaft 143 retracted into the barrel 200.

Referring to FIG. 7A, shown is a schematic drawing illustrating a top view of the needle and barrel assembly 300; FIG. 7B illustrates a left side view of the assembly 300 shown in FIG. 7A; FIG. 7C illustrates a right side view of the assembly 300 shown in FIG. 7A; FIG. 7D illustrates a cross-sectional view through the assembly 300 shown in FIG. 7A along line D-D; FIG. 7E illustrates a perspective view of the assembly 300; and FIG. 7F illustrates an alternative perspective view of the assembly 300. The assembly 300 illustrated collectively in FIGS. 7A-7F is an assembly of the needle 100 illustrated collectively in FIGS. 5A-5F, and the barrel 200 illustrated collectively in FIGS. 6A-6F, and accordingly, elements common to these share common reference numerals.

Figure 8A:
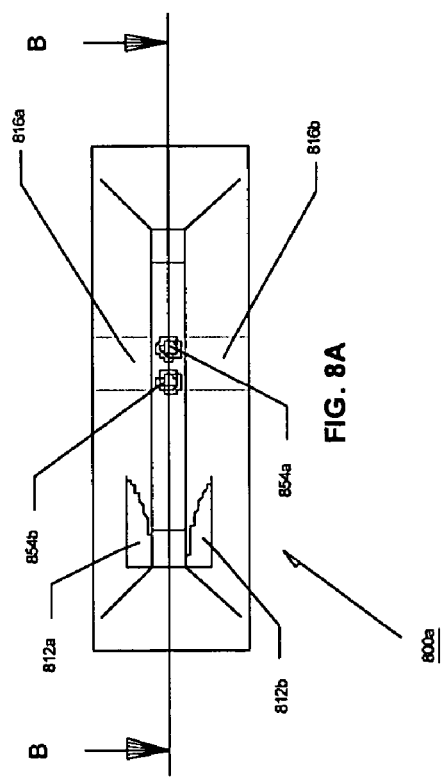
FIG. 8A is a schematic drawing showing details of a front view of a cartridge slot 800a, from a joint-diagnostic spectroscopic and biosensor meter according to an embodiment of the invention.
Figure 8B:
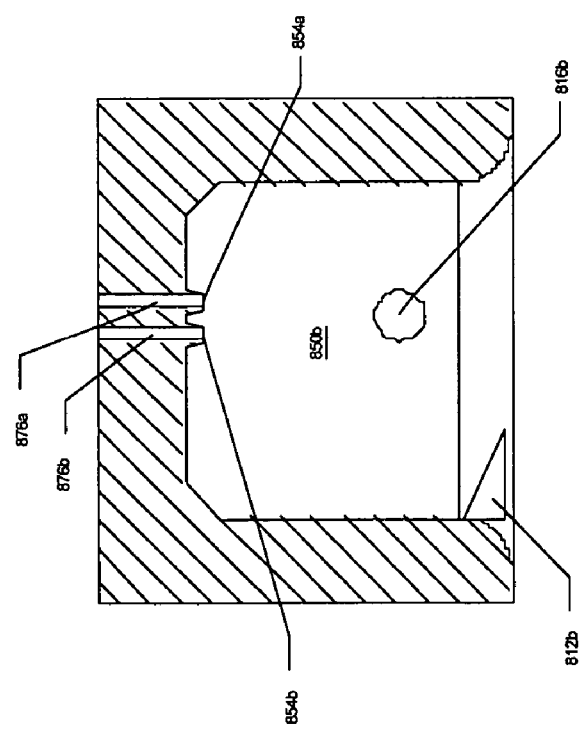
FIG. 8B is a cross-sectional view through the cartridge slot 800a shown in FIG. 8A along line B-B.

Referring collectively to FIGS. 8A-8C, shown are schematic drawings illustrating details of a cartridge slot 800a, for a joint-diagnostic spectroscopic and biosensor meter according to an embodiment of the invention. The cartridge slot is shown schematically as a removable part of the joint-diagnostic spectroscopic and biosensor meter, but those skilled in the art will appreciate that the slot could be an integral part of the meter, as illustrated collectively in FIGS. 12A-12D, as an example.

Referring to FIG. 8A, shown is a schematic drawing of a front view of the cartridge slot 800a; FIG. 8B is a cross-sectional view through the cartridge slot 800a shown in FIG. 8A along line B-B; and FIG. 8C is a perspective view of the cartridge slot 800a. Also shown is a top aperture 816a and a bottom aperture 816b, wherein both apertures are aligned with the optical chamber 616 as illustrated in FIG. 8C, and wherein EMR can either enter the sample through aperture 816a and exit through aperture 816b, or enter the sample through aperture 816b and exit through aperture 816a, depending on the location of the EMR source and the photo-detector. Those skilled in the art will appreciate that the apertures 816a and 816b are not essential, as illustrated in the other embodiments of the invention, shown collectively in FIGS. 10A-10C and FIGS. 11A-11C.

Referring to FIG. 8A and FIG. 8B, shown are electrical input contacts 854a and 854b, for mating with the respective biosensor electrical output contacts 654a and 654b illustrated in FIG. 9B. Passages 876a and 876b are schematic representation of passages used to facilitate communication between respective electrical input contacts 854a and 854b and a processor, by means of electrical conductors, which is well known to those skilled in the art. Also shown are notches 812a and 812b, which are not essential, but can ensure that cartridge 600d, illustrated in FIG. 9C, is inserted in the correct orientation. Those skilled in the art will appreciate that there are other means for ensuring correct insertion of the cartridge 600d, and also that the cartridge slots must be designed to fit the various embodiments of disposable microfluidic cartridges. It should be noted that, as an example, the slot 800a was not designed to accept the cartridge collectively illustrated in FIGS. 2A-2E.

Referring to FIG. 8B and FIG. 8C, the aperture 816a is located in the wall-portion 850a of the cartridge slot 800a, and aperture 816b is located in the wall-portion 850b of the cartridge slot 800a. Parts of the wall-portions 850a and 850b serve to hold the slot 800a together, and parts serve as sliding tracks for insertion of the cartridge 600d shown in FIG. 9C.

Those skilled in the art will appreciate that the wall-portions 850a and 850b are not essential, since in some embodiments of the meter, the slot 800a is an integral part of the housing 892 of the meter, for example meter 900 illustrated collectively in FIGS. 12A-12D.

Referring collectively to FIGS. 9A-9C, shown are schematic drawings illustrating details of a cartridge 600d fully inserted inside the cartridge slot 800a (illustrated collectively in FIGS. 8A-8C), of a joint-diagnostic spectroscopic and biosensor meter according to an embodiment of the invention.

Referring to FIG. 9A, shown is a schematic drawing of a front view of the cartridge 600d fully inserted inside the cartridge slot 800a; FIG. 9B is a cross-sectional view through the cartridge 600d and the cartridge slot 800a shown in FIG. 9A along line B-B; and FIG. 9C is a perspective view of the cartridge 600d fully inserted in the cartridge slot 800a. The cartridge 600d illustrated collectively in FIGS. 9A-9C is similar to the cartridge 600a illustrated collectively in FIGS. 1A-1C, and accordingly, elements common to them share common reference numerals. The primary difference is that cartridge 600d does not have the inlet opening 612 in a piece of threaded capillary tubing 672a. Instead, the inlet opening 612 illustrated in FIGS. 9B & C is an opening to the inlet chamber 670, which can accommodate the male end of a traditional syringe or the male end 171 of the needle assembly 300 shown collectively in FIGS. 7A-7F.

Figure 10C:
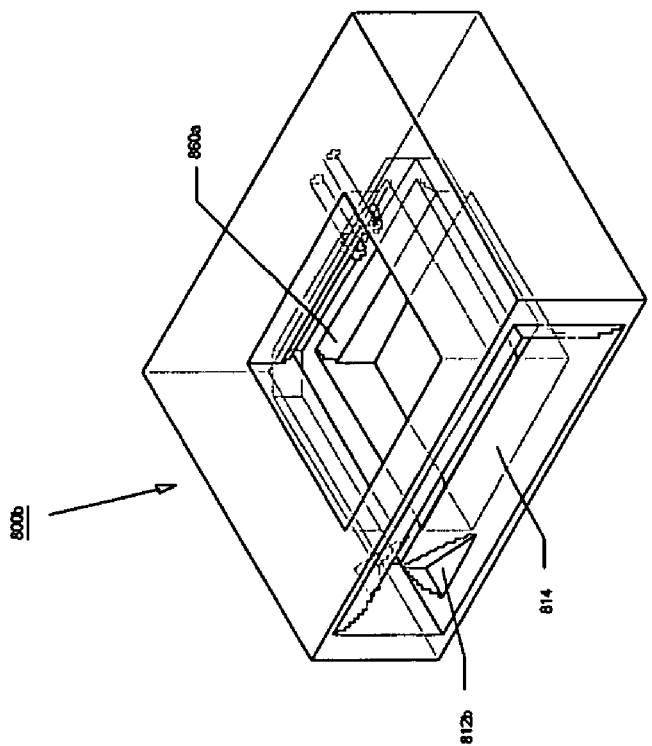
FIG. 10C is a perspective view of the cartridge slot 800b.
Figure 10A:
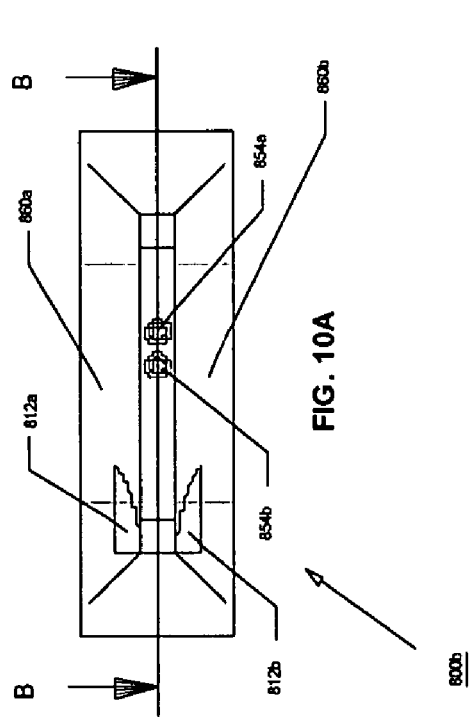
FIG. 10A is a schematic drawing showing details of a front view of a cartridge slot 800b, from a joint-diagnostic spectroscopic and biosensor meter according to an embodiment of the invention.
Figure 10B:
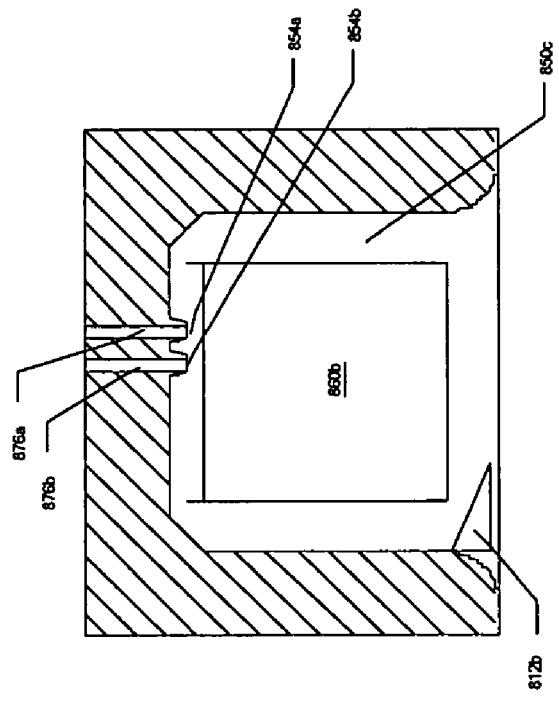
FIG. 10B is a cross-sectional view through the cartridge slot 800b shown in FIG. 10A along line B-B.

Referring collectively to FIGS. 10A-10C, shown are schematic drawings illustrating details of a cartridge slot 800b, for a joint-diagnostic spectroscopic and biosensor meter according to an embodiment of the invention.

Referring to FIG. 10A, shown is a schematic drawing of a front view of the cartridge slot 800b; FIG. 10B is a cross-sectional view through the cartridge slot 800b shown in FIG. 10A along line B-B; and FIG. 10C is a perspective view of the cartridge slot 800b. The cartridge slot 800b illustrated collectively in FIGS. 10A-10C is similar to the cartridge slot 800a illustrated collectively in FIGS. 8A-8C, and accordingly, elements common to them share common reference numerals. The primary difference is that aperture 816b in the wall-portion 850b is replaced with a large cutout section shown as 860b in FIG. 10B, and the surrounding section, identified as 850c, still functions as an aid for insertion of the cartridge. Similarly, the aperture 816a in the wall-portion 850a (FIG. 8C) is replaced with a large cutout section shown as 860a in FIG. 10C. Therefore, there is no aperture to channel EMR from the EMR source (shown collectively in FIGS. 12A-12C as 880) to the cartridge, and also there is no aperture to channel EMR emerging from the sample, to the photodetector (included in part 890 shown in FIGS. 12A & C).

Figure 11C:
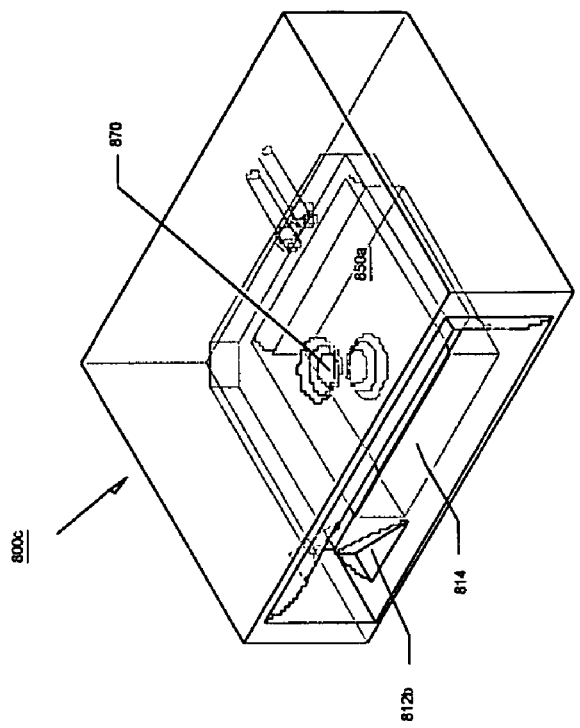
FIG. 11C is a perspective view of the cartridge slot 800c.
Figure 11A:
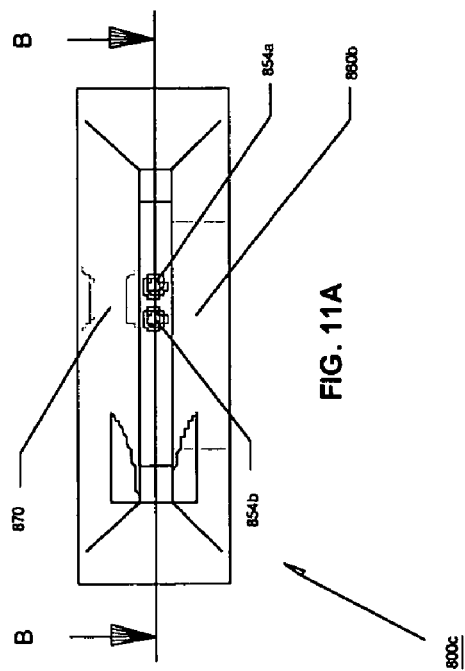
FIG. 11A is a schematic drawing showing details of a front view of a cartridge slot 800c, from a joint-diagnostic spectroscopic and biosensor meter 900 (shown collectively in FIGS. 12A-12D) according to an embodiment of the invention.
Figure 11B:
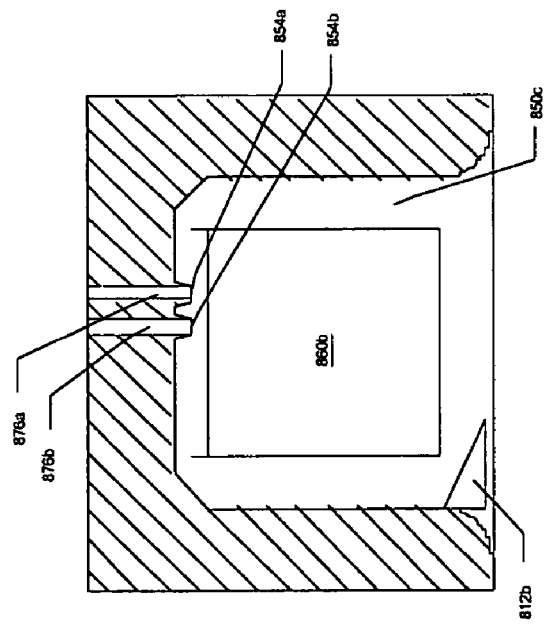
FIG. 11B is a cross-sectional view through the cartridge slot 800c shown in FIG. 11A along line B-B.

Referring collectively to FIGS. 11A-11C, shown are schematic drawings illustrating details of a cartridge slot 800c, for a joint-diagnostic spectroscopic and biosensor meter according to an embodiment of the invention.

Referring to FIG. 11A, shown is a schematic drawing of a front view of the cartridge slot 800c; FIG. 11B is a cross-sectional view through the cartridge slot 800c shown in FIG. 11A along line B-B; and FIG. 11C is a perspective view of the cartridge slot 800c. The cartridge slot 800c illustrated collectively in FIGS. 11A-11C is similar to the cartridge slot 800a illustrated collectively in FIGS. 8A-8C, and accordingly, elements common to them share common reference numerals. The primary difference is that aperture 816b in the wall-portion 850b (FIG. 8B) is replaced with a large cutout section shown as 860b in FIG. 11B, and the surrounding section, identified as 850c, still functions as an aid for insertion of the cartridge. The second difference is a focusing lens 870 located in the wall-portion 850a of the cartridge slot, which is positioned to focus the EMR emerging from the sample, onto the detector included in part 890 shown in FIG. 12A and FIG. 12C, after the cartridge electrical output contacts (shown as 654a and 654b in FIG. 9B) mate with the corresponding electrical input contacts 854a and 854b in the meter slot 800c.

Referring collectively to FIGS. 12A-12D, shown are schematic drawings illustrating details of a joint-diagnostic spectroscopic and biosensor meter 900 according to an embodiment of the invention. In this embodiment of the invention, there is no aperture for channeling the EMR from the EMR source 880 to the sample, and there is a lens 870 for focusing EMR emerging from the sample, unto the photodetector included in part 890.

Referring to FIG. 12A, shown is a schematic drawing of a front view of the joint-diagnostic spectroscopic and biosensor meter 900; FIG. 12B is a first cross-sectional view through the joint-diagnostic spectroscopic and biosensor meter 900 shown in FIG. 12A along line B-B, showing the slot 800c as an integral part of the housing 892 of the meter 900; FIG. 12C is a second cross-sectional view through the joint-diagnostic spectroscopic and biosensor meter 900 shown in FIG. 12A along line C-C; and FIG. 12D is a perspective view of the joint-diagnostic spectroscopic and biosensor meter 900, showing the housing 892, a display screen 894, three buttons 882a, 882b and 882c, for manipulating the display functions. The cartridge slot 800c illustrated collectively in FIGS. 12A-12D is similar to the cartridge slot 800c illustrated collectively in FIGS. 11A-11C, and accordingly, elements common to them share common reference numerals.

Referring collectively to FIG. 13A to FIG. 23C are schematic drawings illustrating details of alternative embodiments of disposable cartridges. Those skilled in the art will appreciate the various ways parts of the cartridges illustrated can be combined, and are all considered to be a part of the present invention.

Referring collectively to FIGS. 13A-13C, shown are schematic drawings illustrating details of a spectroscopic and biosensor cartridge 600e that can be used with a joint-diagnostic spectroscopic and biosensor meter according to an embodiment of the invention.

Referring to FIG. 13A is a schematic drawing showing a top view of the cartridge 600e; FIG. 13B is a first cross-sectional view through the spectroscopic and biosensor cartridge 600e shown in FIG. 13A along line B-B; FIG. 13C is a second cross-sectional view through the spectroscopic and biosensor cartridge 600e shown in FIG. 13B along line C-C. The cartridge 600e illustrated collectively in FIGS. 13A-13C is similar to the cartridge 600a shown collectively in FIGS. 1A-1C, and accordingly, elements common to them share common reference numerals. The first difference is that cartridge 600e does not have the inlet opening 612 in a piece of threaded capillary tubing 672a. Instead, the inlet opening 612 shown in FIG. 13C is an opening to the inlet chamber 670, which can accommodate the male end of a traditional syringe. The second difference is that the biosensors in cartridge 600e can be calibrated prior to sample measurement.

Some biosenors, for example a pH biosensor, require a one point calibration for accurate measurement of pH. Shown collectively in FIGS. 13A-13C is a sealed calibration pouch 928 containing an appropriate calibration fluid, seated in a calibration pouch cavity 924. The pouch cavity 924 is slightly larger than the pouch 928 and the shape of the pouch 928 is similar to the shape of the pouch cavity 924, which is fluidly connected to the biosensor chamber 674, via a conduit 922. The cartridge housing 123 includes a flexible member 930, which allows compression of the pouch 928 when the flexible member 930 is compressed, under control of the meter. The base of the cavity 928 is fitted with a projected member (not shown), which ruptures the pouch 928 when pressure is applied to the flexible member 930. Those skilled in the art will appreciate that the projected member is sharp enough to penetrate the wall 926 of the pouch 928, only after pressure is applied to the flexible member 930. The pressure within the pouch cavity 924 dispels the calibration fluid from the ruptured pouch, into the biosensor chamber 674. Contact between the calibration fluid and the biosensors 652a and 652b, facilitate calibration of the biosensors, under control of the meter. Those skilled in the art will appreciate that calibration of all the biosensors with the calibration fluid may not be required, and the composition of the calibration fluid is appropriate for the biosensors that require calibration. In order to maintain contact between the calibration fluid and the biosensors, the biosensor chamber 674 is fitted with two capillary breaks 920a and 920b. The capillary break 920a prevents the calibration fluid from flowing towards the inlet opening 612, and the capillary break 920b prevents the calibration fluid from flowing towards the vent 137b. In operation, the sample is contained in a syringe with a male outlet end that mates with the inlet chamber 670.

In the embodiment of the meter using cartridge 600e, the cartridge is preferably inserted into the cartridge slot (for example 800a illustrated in FIG. 9C) before it is filled with sample. The syringe carrying the sample may be inserted into the inlet chamber 670 before or after the cartridge is inserted into the cartridge slot 800a. Upon proper insertion and under the control of the meter, the calibration pouch 928 becomes ruptured, and the pressure forces the calibration fluid into the biosensor chamber 674. The volume of the calibration fluid and the pressure applied to the pouch 928 is sufficient to fill the biosensor chamber with calibration fluid, without pushing any fluid beyond the capillary breaks 920a and 920b. It will be appreciated by those skilled in the art that there are several methods that can be used to rupture the calibration pouch. In another embodiment of the cartridge 600e, the wall 926 of the calibration pouch 928 possesses a weak section, where rupture of the pouch 928 occurs when pressure is applied to the flexible member 930. In such an embodiment, there is no need of the projection member at the base of the cavity 924. In some embodiments, the calibration pouch may contain an object with projections on the object, so that when pressure is applied to the calibration pouch, the projections in the object will rupture the calibration pouch. Those skilled in the art will appreciate that other means of rupturing the pouch 928 could be used. The meter must include means for delivering pressure to the flexible member 930, and as non-limiting examples, the pressure could be delivered by a plunger or a rotating cam in contact with the flexible member 930 in the joint-diagnostic spectroscopic and biosensor meter.

After calibration of the biosensors, under control of the meter, the syringe carrying the sample is inserted into the inlet chamber 670 if it is not already inserted, and the sample is injected from the syringe into the cartridge 600e. In the embodiment of the spectroscopic and biosensor meter that uses the cartridge 600e, preferably the display screen provides instructions for injecting the sample into the cartridge, and how to begin measurement after the sample is properly injected into the cartridge.

The injected sample first reaches the manifold 640, which distributes sample to the spectroscopy inlet transition chamber 614a and the biosensor inlet transition chamber 642. The sample in the biosensor inlet transition chamber 642 is forced across the capillary break 920a and through the biosensor chamber 674, replacing the calibration fluid with sample. Simultaneously, sample is forced from the spectroscopy inlet transition chamber 614a, through the optical chamber 616a, out into the overflow chamber 618a, and into the outflow chamber 620a. The pressure is applied to the syringe plunger until sample appears in the spectroscopy capillary break 622a. In this embodiment of the invention, capillary action is not essential for sample movement, and the capillary break 622a also serves as a buffer chamber for excess sample. The cartridge 600e is sufficiently translucent or transparent so that the operator can observe the sample as it travels. As a guide to the operator, two fill-between-lines 621a and 621b are displayed around the capillary break 622a, with instructions on the surface of the cartridge 600e. Having the leading end of the sample anywhere between the lines is an indication that the cartridge is filled with sufficient sample for both spectroscopic and biosensor measurement. Optionally, there could also be two similar fill-between-lines around the biosensor capillary break 622b. The expelled calibration fluid is preferably colorless, allowing the leading end of the blood sample to be seen easily, and the leading end of the blood should be located between the two fill-between-lines 621a and 621b. The volume of the capillary break 622b is sufficiently large to accommodate the calibration fluid and prevent any fluid from reaching the vent 137b. Although the capillary breaks 622a and 622b are shown to be located the same distance from their respective vents 137a and 137b, it will be appreciated by those skilled in the art that this is not essential. In this embodiment, the chambers are designed so that an indication that the spectroscopic flow path is sufficiently filled, is also an indication that the biosensor flow path is sufficiently filled.

Referring collectively to FIGS. 14A-14E, shown are schematic drawings illustrating details of a spectroscopic and biosensor cartridge 600f that can be used with a joint-diagnostic spectroscopic and biosensor meter according to an embodiment of the invention.

Referring to FIG. 14A is a schematic drawing showing a top view of the cartridge 600f; FIG. 14B is a first cross-sectional view through the spectroscopic and biosensor cartridge 600f shown in FIG. 14A along line B-B; FIG. 14C is a second cross-sectional view through the spectroscopic and biosensor cartridge 600f shown in FIG. 14B along line C-C; FIG. 14D is a third cross-sectional view through the spectroscopic and biosensor cartridge 600f shown in FIG. 14A along line D-D; and FIG. 14E is a fourth cross-sectional view through the spectroscopic and biosensor cartridge 600f shown in FIG. 14A along line E-E. The cartridge 600f illustrated collectively in FIGS. 14A-14D is similar to the cartridge 600a shown collectively in FIGS. 1A-1C and cartridge 600e illustrated collectively in FIGS. 13A-13C, and accordingly, elements common to them share common reference numerals. The first difference is that cartridge 600f has an inlet opening 612 in a piece of capillary tubing 672b, and depends on capillary action to fill the cartridge 600f with sample. The inlet chamber 670 is shown as the inside of the piece of capillary tubing 672b, and blood sample can be drawn from a pin prick drop of blood. Alternative views of cartridge 600f are shown collectively in FIGS. 15A-15C, as a cartridge and cap assembly 600g. The cap is shown as 960, tethered to the inlet tubing 672b by a ring 966 and a tether 964. An empty calibration pouch cavity 924 is shown in FIGS. 14A, C and D, but the calibration pouch 928 is shown in the cavity 924 in FIG. 15B. Referring to FIG. 15A is a schematic drawing showing the bottom view of a spectroscopic and biosensor cartridge (600f) and cap (960) assembly 600g. It should be understood that the labels top view and the bottom view are labels used to indicate the position of one view relative to the other, and does not suggest the orientation of the cartridge relative to the meter. FIG. 15B is a first cross-sectional view through the spectroscopic and biosensor cartridge and cap assembly 600g shown in FIG. 15A along line B-B; and FIG. 15C is a second cross-sectional view through the spectroscopic and biosensor cartridge and cap assembly 600g shown in FIG. 15A along line C-C.

Referring again collectively to FIGS. 14A-14E and 15A-15C, the second difference in cartridge 600f, is the inclusion of an air chamber 940, in fluid connectivity with the inlet chamber 670, via a conduit 942. The air chamber 940 can displace air through the conduit 942, by compressing a flexible member 944, under control of the meter. A third difference is the relocation of the vent 137a, to a position adjacent to and on the same plane as the flexible member 630 of the calibration pouch cavity 924. The vent 137a is in fluid connectivity with the capillary break 622a, via a conduit 135a. In order for a joint-diagnostic spectroscopic and biosensor meter to use a cartridge like 600f, the meter must further comprise means for compressing the flexible member 944 of the air chamber 940, for example without any limitation, a plunger or rotating cam, and the meter must also comprise a means for sealing the vent 137a during use.

To test a patient's blood using a pin prick drop of blood on the patient's skin as the sample, for example, the inlet opening 612 of cartridge 600f is inserted inside the drop of blood. The blood is drawn into the inlet chamber 670, and then into the manifold 640 where the blood diverges into a spectroscopic flow path and a biosensor flow path up to the capillary breaks 622a and 920a. The blood is drawn in by capillary action, therefore the manifold 640 is not too large to impede blood flow. The capillary break 920a keeps the blood away from the biosensors, to allow calibration of the biosensors prior to sample measurement, and the capillary break 622a keeps the blood away from the vent 137a. The spectroscopic flow path is defined as the flow path beginning at the manifold 640 and terminating at the vent 137a; the biosensor flow path is defined as the flow path beginning at the manifold 640 and terminating at the vent 137b.

After blood is drawn into the spectroscopic flow path and the biosensor flow path up to capillary breaks 622a and 920a respectively, the inlet opening 612 is then sealed with the cap 960. Those skilled in the art will appreciate that other types of caps may be used, for example without limitations, a threaded cap that fits on the threaded piece of capillary tube at the inlet opening 612, in FIGS. 1A & B, identified as 672a. At this time, the flow paths in the cartridge housing 123 of cartridge 600f are still open at vents 137a and 137b. The cartridge and cap assembly 600g containing blood sample is then inserted into the cartridge slot, for example 800c shown in FIGS. 12B and 12C. After insertion, the biosensor electrical output contacts 654a and 654b mate with the meter slot electrical input contacts 854a and 854b shown in FIG. 11B, a signal is sent to the meter to begin biosensor calibration: the calibration pouch 928 becomes ruptured, under control of the meter, the biosensor chamber 674 becomes filled with calibration fluid; the biosensors generate biosensor electrical signals after calibration fluid come in contact with the biosensors; the calibration biosensor electrical signals provide calibration biosensor data to the meter processor for calibrating the biosensors. A control signal generated from the biosensor electrical signals could also be sent to a spectroscopic control module in the processor, to signal the start of the spectroscopic measurement. As mentioned, a device like a plunger must press on the flexible member 930 in order to rupture the calibration pouch 928, and release its contents into the biosensor chamber 674. The plunger used for biosensor calibration, in this embodiment of the joint-diagnostic spectroscopic and biosensor meter, has a second arm (not shown) with a blunt tip, which enters the vent 137a and creates a seal. After the plunger second arm seals vent 137a, the only opening in the cartridge and cap assembly 600g, is the vent 137b. The next step is compression of the air chamber 940, under control of the meter, via the flexible member 944 using for example, which should not be considered limiting in any way, a plunger or a rotating cam. The compression of the air chamber 940 propels air into the inlet chamber 670, via the conduit 942. The propelled air forces some of the blood in the biosensor inlet transition chamber 642 and the manifold 640 across the capillary break 920a, and then into the biosensor chamber 674, replacing the calibration fluid with blood. After a predetermined time applying pressure to the air chamber, and with the blood in contact with the biosensors, the biosensors generate biosensor electrical signals. The sample biosensor electrical signals provide sample biosensor data to the meter processor for sample measurement. Because the embodiment of a disposable cartridge comprises two flow paths, in order for the air in the air chamber to displace the blood into the biosensor chamber 674, displacing the calibration fluid into the biosensor outflow 620b, both the inlet opening 612 and the spectroscopic vent 137a must be sealed. The biosensor vent 137b must remain open during the propulsion of air from the air chamber 940.

In another embodiment of the system (not shown), the vent 137a is sealed with a spring loaded ball (instead of the blunt tip mentioned previously) strategically located in the cartridge slot 800c, so that the ball becomes seated in the vent 137a, when the cartridge is properly inserted in the slot 800c. It will be appreciated by those skilled in the art, that other means of sealing openings may be used, to facilitate the flushing action of the air from the air chamber. In the embodiment of the disposable cartridge illustrated collectively in FIGS. 22A-22D, the cartridge 600v comprises a single flow path and biosensor calibration means. In this embodiment, sealing of the inlet opening 612 with the cap 960 provides the required sealing for operating the air chamber 940.

Referring collectively to FIGS. 16A-16C, shown are schematic drawings illustrating details of a spectroscopic and biosensor whole blood and plasma cartridge 600h that can be used with a joint-diagnostic spectroscopic and biosensor meter according to an embodiment of the invention.

Referring to FIG. 16A is a schematic drawing showing a top view of the spectroscopic and biosensor whole blood and plasma cartridge 600h; FIG. 16B is a first cross-sectional view through the spectroscopic and biosensor whole blood and plasma cartridge 600h shown in FIG. 16A along line B-B, and FIG. 16C is a second cross-sectional view through the spectroscopic and biosensor whole blood and plasma cartridge 600h shown in FIG. 16B along line C-C. The cartridge 600h illustrated collectively in FIGS. 16A-16C is similar to the cartridge illustrated collectively in FIGS. 2A-2E, and accordingly, elements common to them share common reference numerals. The first difference is that cartridge 600h does not have an inlet opening 612 in an inlet chamber 670 that is designed to accommodate the male end of a syringe. Instead, the inlet opening 612 shown collectively in FIGS. 16A and 16C is the opening in a piece of capillary tubing 672b. The second difference is the absence of vents 137a, 137b and 137c, and capillary breaks 622a, 622b and 622c shown in FIG. 2E. Instead, the filtration chamber outflow 620a, the blood biosensor outflow 620b, and the plasma outflow 620c converge into a vacuum chamber 960a. The vacuum chamber 960a is a cavity in the housing 123 with flexible members 962a and 962b (FIG. 16B). By manually squeezing and releasing the flexible members 962a and 962b, a negative pressure is generated in the vacuum chamber 960a. The third difference is the location of the center of the blood optical chamber 616*a* and the plasma optical chamber 616*b*, as shown in FIG. 16A, where the distances A and B are equal. The only opening in cartridge 600*h* is the inlet opening 612, which can be capped, for example, with a cap 960 shown in FIGS. 15A-15B. Those skilled in the art will appreciate that one flexible member (962*a* or 962*b*) could perform the same function. The volume of the vacuum chamber 960*a*, and the maximum depression of the flexible members 962*a* and 962*b*, determines the maximum volume of fluids that could be drawn into the flow paths. Also, the rigidity of the flexible members 962*a* and 962*b*, which contributes to the rate at which the members 962*a* and 962*b* are restored to their original shape after squeezing and releasing (the rebound of the flexible members 962*a* and 962*b*), determines the velocity of the fluids in the flow paths. In this embodiment of a disposable cartridge, there are two whole blood flow paths, and one plasma flow path: the first whole blood flow path is defined as the flow path that includes the blood biosensor chamber 674, beginning at the manifold 640 and terminating at the vacuum chamber 960*a*; the second whole blood flow path is defined as the flow path that includes the whole blood optical chamber 616*a* and the flow-through filtration chamber 634, beginning at the manifold 640 and terminating at the vacuum chamber 960*a*; the third flow path, referred to as the plasma flow path, is defined as the flow path that includes the plasma biosensor chamber 672 and the plasma optical chamber 616*b*, beginning at the plasma collection chamber 636 and terminating at the vacuum chamber 960*a*.

To test a patient's blood, the flexible members 962*a* and 962*b* must first be squeezed, preferably between two fingers, to dispel air from the vacuum chamber 960*a*. With air inside the pouch 960*a* dispelled, the inlet opening 612 of the cartridge 600*f* is then inserted into a blood sample, which could be a drop of blood on the patient's skin, generated from a pin prick. To draw the blood into the cartridge 600*h*, the flexible members 962*a* and 962*b* must be released, creating a negative pressure within the vacuum chamber 960*a*. The extraction of plasma from the blood depends on the capillary action, the negative pressure created in the vacuum chamber 960, the surface area of the hollow fiber filters in bundle 660*a*, and the pore size in the membrane. The surface area is increased by increasing the number of hollow fiber filters. Details of the hollow fiber filter bundle 660*a* are shown collectively in FIGS. 3A-3G.

The joint-diagnostic spectroscopic and biosensor meter could have a single EMR path or two EMR paths. The cartridge 600*b* illustrated collectively in FIGS. 2A-2E requires two EMR paths: one for the whole blood optical chamber 616*a*, and another for the plasma optical chamber 616*b*, because the optical chambers are not located approximately equidistant from their respective sides of the cartridge 600*b*, shown as distances A and B in FIG. 16A. The cartridge illustrated collectively in FIGS. 16A-16C could operate with either a single EMR path or two EMR paths, since the distance A is about equal to the distance B (FIG. 16A).

When the cartridge 600*h* containing sample is inserted into a slot providing a single EMR path, the biosensor measurement and one spectroscopic measurement is performed. The spectroscopic measurement is performed either on the blood or on the plasma. In order to perform the second spectroscopic measurement, the cartridge 600*h* must be removed and flipped over 180 degrees before reinsertion in the cartridge slot. In an embodiment of the joint-diagnostic spectroscopic and biosensor meter, the software allows the meter to detect whether the sample in the EMR path is plasma or whole blood, and the appropriate spectroscopic algorithm is applied.

It must also be noted that the biosensor electrical output contact is not affected after flipping the cartridge, due to the central location of the contact.

Referring collectively to FIGS. 17A-17D, shown are schematic drawings illustrating details of a spectroscopic and biosensor whole blood and plasma cartridge 600*k* that can be used with the joint-diagnostic spectroscopic and biosensor meter according to an embodiment of the invention.

Referring to FIG. 17A is a schematic drawing showing a top view of the cartridge 600*k*; FIG. 17B is a first cross-sectional view through the cartridge 600*k* shown in FIG. 17A along line B-B; FIG. 17C is a second cross-sectional view through the cartridge 600*k* shown in FIG. 17A along line C-C; and FIG. 17D is a third cross-sectional view through the cartridge 600*k* shown in FIG. 17B along line D-D. The cartridge 600*k* illustrated collectively in FIGS. 17A-17D is similar to the cartridge illustrated collectively in FIGS. 16A-16C, and accordingly, elements common to them share common reference numerals. The first difference is that cartridge 600*k* has a single whole blood flow path, for facilitating plasma filtration and spectroscopic measurement. The second difference is that the whole blood flow path terminates in a first vacuum chamber 960*c*, and the plasma flow path terminates in a second vacuum chamber 960*b*. Vacuum chamber 960*c* is not fluidly connected to vacuum chamber 960*d*, except through pores of the filter 660*a*, shown collectively in FIGS. 3A-3G. However, this fluid connection does not exist when the hollow fiber filter bundle 660*a* is surrounded by blood in the flow-through filtration chamber 634. Those skilled in the art will appreciate that the vacuum capacity or the draw in pouch 960*b* and pouch 960*c* must be optimized for efficient plasma extraction and measurements. No whole blood optical chamber overflow chamber 618*a* (FIG. 16C) is shown, because the overflow 618*a* overlaps with the blood filtration chamber 634, and the initial segment of the filtration chamber 634 is regarded as the overflow chamber 618*a*.

Referring collectively to FIGS. 18A-18E, shown are schematic drawings illustrating details of an alternative embodiment a spectroscopic and biosensor whole blood and plasma cartridge 600*m* that can be used with the joint-diagnostic spectroscopic and biosensor meter according to an embodiment of the invention.

Referring to FIG. 18A is a schematic drawing showing a top view of the cartridge 600*m*; FIG. 18B is a first cross-sectional view through the whole blood and plasma cartridge 600*m* shown in FIG. 18A along line B-B; FIG. 18C is a second cross-sectional view through the whole blood and plasma cartridge 600*m* shown in FIG. 18B along line C-C; FIG. 18D is a third cross-sectional view through the whole blood and plasma cartridge 600*m* shown in FIG. 18A along line D-D; and FIG. 18E is a detailed view of the detail E shown in FIG. 18D. The cartridge 600*m* illustrated collectively in FIGS. 18A-18E is similar to the cartridge illustrated collectively in FIGS. 17A-17D, and accordingly, elements common to them share common reference numerals. The first difference is that cartridge 600*m* has a combination of a vent 137*a* at the end of the whole blood flow path, and a vacuum chamber 960*d* at the end of the plasma flow path. The second difference is that the flow-through filtration chamber comprises a flat membrane 694 instead of the hollow fiber filter bundle 660*a* shown in FIGS. 17C & 17D. The filtration chamber 634 could also be referred to as the section of the whole blood flow path 634 in contact with the membrane 694, because the blood compartment 634 is easily distinguishable from the plasma compartment 636*a* and 636*b* in FIG. 18C. The section of the plasma compartment in contact with the membrane 694 is referred to as 636*a*, and the plasma collection chamber (shown as 636 in FIG. 17D) is referred to as 636b. For clarity, 634 represents the part of the blood compartment in contact with one side of the membrane, 636 represents the part of the plasma compartment in contact with the second side of the membrane, and 694 represents the membrane, whether the membrane is flat as illustrated collectively in FIGS. 18A-18E, or tubular as illustrated collectively in FIGS. 3A-3G.

In the embodiment illustrated collectively in FIGS. 18A-18E, capillary action is required for the flow of blood along the whole blood flow path, and a combination of capillary action and negative pressure is required for plasma extraction and flow. The third difference is that in this embodiment, the whole blood flow path does not include a measurement facility.

Referring collectively to FIGS. 18A-18E, shown are schematic drawings illustrating details of an alternative embodiment of a spectroscopic and biosensor whole blood and plasma cartridge 600n that can be used with the joint-diagnostic spectroscopic and biosensor meter according to an embodiment of the invention.

Referring to FIG. 19A is a schematic drawing showing a top view of the cartridge 600n; FIG. 19B is a first cross-sectional view through the cartridge 600n shown in FIG. 19A along line B-B; FIG. 19C is a second cross-sectional view through the cartridge 600n shown in FIG. 19A along line C-C; and FIG. 19D is a third cross-sectional view through the cartridge 600n shown in FIG. 19B along line D-D. The cartridge 600n illustrated collectively in FIGS. 19A-19D is similar to the cartridge illustrated collectively in FIGS. 17A-17D, and accordingly, elements common to them share common reference numerals. The major difference is that the fiber bundle 660b, illustrated collectively in FIGS. 20A-20E in details, comprise perforated flanges on both ends (684a and 684b), and the whole blood flows through the hollow fiber filters instead of around the hollow fiber filters. A second difference is the whole blood biosensor chamber 674 replaces the optical chamber 616a shown in FIG. 17D. The whole blood biosensor chamber 674 must be located before the filtration chamber 634, because the blood emerging from the filtration chamber has a higher hematocrit. Those skilled in the art will appreciate that the lumen 692 of the hollow fiber filters must be larger than the lumen in the embodiment illustrated in FIGS. 3A-3G, to avoid plugging of the lumen with blood.

Referring collectively to FIGS. 20A-20E, shown are schematic drawings illustrating details of an embodiment of a hollow fiber filter bundle 660b shown in cartridge 600n (illustrated collectively in FIGS. 19A-19D).

Referring to FIG. 20A is schematic drawing showing details of a top view of the hollow fiber filter bundle 660b; FIG. 20B is a perspective view of the hollow fiber filter bundle 660b, showing a first perforated flange 684a in clear view; FIG. 20C is an alternative perspective view of the hollow fiber filter bundle 660b, showing a second perforated flange 684b in clear view; FIG. 20D is a cross-sectional view through the hollow fiber filter bundle 660b shown in FIG. 20A along line D-D; and FIG. 20E is a detailed view of the detail E shown in FIG. 20D. The hollow fiber filter bundle 660b illustrated collectively in FIGS. 20A-20E is similar to the cartridge illustrated collectively in FIGS. 3A-3G, and accordingly, elements common to them share common reference numerals. The major differences are that both flanges 684a and 684b are perforated, and hollow fiber filter bundle 660b comprises four hollow fiber filters instead of seven.

Referring collectively to FIGS. 21A-21D, shown are schematic drawings illustrating details of a spectroscopic and biosensor cartridge 600p, that can be used with a joint-diagnostic spectroscopic and biosensor meter according to an embodiment of the invention.

Referring to FIG. 21A is a schematic drawing showing details of a top view of the cartridge 600p; FIG. 21B is a first cross-sectional view through the spectroscopic and biosensor cartridge 600p shown in FIG. 21A along line B-B; FIG. 21C is a second cross-sectional view through the spectroscopic and biosensor cartridge 600p shown in FIG. 21A along line C-C; and FIG. 21D is a third cross-sectional view through the spectroscopic and biosensor cartridge 600p shown in FIG. 21B along line D-D. The cartridge 600p illustrated collectively in FIGS. 21A-21D is similar to the cartridge 600a illustrated collectively in FIGS. 1A-1C, and accordingly, elements common to them share common reference numerals. The major difference is that cartridge 600p comprises a single flow path, defined by the inlet opening 612 at the beginning, and terminating at a vacuum chamber 960e. The single flow path includes an optical chamber 616a, followed by a biosensor chamber 674. A second difference is that the piece of capillary tubing 672p housing the inlet opening 612 is not threaded. In this embodiment, there is an indicator line 621c with instructions for adequate filling. Because there is no open vent as 137a and 137b shown in FIG. 1B, any excess sample past the line 621c, would remain in the confines of the flow path, which begins at the inlet opening 612 and terminates at the vacuum chamber 960e.

Referring collectively to FIGS. 22A-22D, shown are schematic drawings illustrating details of a spectroscopic and biosensor cartridge (600s) and cap (960) assembly 600v, that can be used with a joint-diagnostic spectroscopic and biosensor meter according to an embodiment of the invention.

Referring to FIG. 22A is a schematic drawing showing details of a top view of the cartridge (600s) and cap (960) assembly 600v; FIG. 22B is a first cross-sectional view through the spectroscopic and biosensor cartridge and cap assembly 600v shown in FIG. 22A along line B-B; FIG. 22C is a second cross-sectional view through the spectroscopic and biosensor cartridge and cap assembly 600v shown in FIG. 22A along line C-C; and FIG. 22D is a third cross-sectional view through the spectroscopic and biosensor cartridge and cap assembly 600v shown in FIG. 22C along line D-D. The cartridge and cap assembly 600v illustrated collectively in FIGS. 22A-22D is similar to the cartridge 600f illustrated collectively in FIGS. 14A-15C, and accordingly, elements common to them share common reference numerals. The major difference is that this embodiment comprises a single flow path.

Referring collectively to FIGS. 23A-23D, shown are schematic drawings illustrating details of a spectroscopic and biosensor cartridge 600w, that can be used with a joint-diagnostic spectroscopic and biosensor meter according to an embodiment of the invention.

Referring to FIG. 23A is a schematic drawing showing details of a top view of the cartridge 600w; FIG. 23B is a first cross-sectional view through the spectroscopic and biosensor cartridge 600w shown in FIG. 23A along line B-B; and FIG. 23C is a second cross-sectional view through the spectroscopic and biosensor cartridge 600w shown in FIG. 23B along line C-C. The cartridge 600w illustrated collectively in FIGS. 23A-23C is similar to the cartridge 600p illustrated collectively in FIGS. 21A-21D, and accordingly, elements common to them share common reference numerals. The first difference is a vent 137d and a capillary break 622d is shown instead of the vacuum chamber 960e shown in FIG. 21D. The second difference is the inlet opening 612 is housed in a flared inlet chamber 670, instead of a piece of capillary tubing 672b shown in FIG. 21D. In use, the inlet opening 612 of the flared inlet chamber 670 is placed over a pin prick, before or after a drop of blood is generated at the skin of the body party, and the blood is allowed to flow into the cartridge 600w, with slight squeezing of the body part around the pin prick. It is well known that excessive squeezing will contaminate the blood with interstitial fluid, and the amount of squeezing tolerated depends on the analytes being measured.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

The invention claimed is:

1. A spectroscopic and biosensor system for analyzing a blood sample taken from a patient, the system comprising:
   a disposable cartridge, the disposable cartridge comprising:
      a cartridge housing;
      an inlet opening in the cartridge housing for receiving the blood sample;
      one or more than one flow path to receive the blood sample from the inlet opening;
      an optical chamber in the one or more than one flow path, the optical chamber having at least one optical window to facilitate detection of an electromagnetic radiation-based signal derived from the blood;
      a biosensor chamber in the one or more than one flow path, the biosensor chamber comprising a pH biosensor, the cartridge housing further comprising an electrical output contact in electrical communication with the pH biosensor for receiving sample biosensor data from the pH biosensor after the blood sample makes contact with the pH biosensor
      at least one of an outlet vent and a compression suction chamber for facilitating flow of the blood sample inside the one or more than one flow path; and
   a meter absent one or more blood fluid connection with the disposable cartridge, the meter further comprising:
      a meter housing;
      a meter source of electromagnetic radiation;
      a slot in the meter housing for receiving the cartridge, the slot having an electrical input contact for mating with the output contact of the cartridge when the cartridge is inserted into the slot; and
      one or more than one photodetector for measuring electromagnetic radiation transmitted through or reflected from the blood sample within the optical chamber and for providing an electromagnetic radiation-based signal derived from the electromagnetic radiation transmitted through or reflected from the blood sample; and
      a processor, the processor comprising:
         a blood hemoglobin oxygen saturation calibration algorithm for transforming the electromagnetic radiation-based signal into a blood hemoglobin oxygen saturation result; and
         a pH calibration algorithm for transforming the sample biosensor data into a pH result,
      the processor being in communication with i) the one or more than one photodetector to receive the electromagnetic radiation-based signal, and ii) the electrical input contact to receive the sample biosensor data;
   whereby the blood hemoglobin oxygen saturation result and the blood pH result will provide an assessment of the patient's oxygenation and acid-base status.

2. The system according to claim 1, wherein
the disposable cartridge further comprises:
   a cavity within the cartridge housing having a sealed calibration pouch containing a calibration fluid for calibrating the pH biosensor;
   a puncture element for puncturing the sealed calibration pouch and for releasing the calibration fluid from the sealed calibration pouch;
   a conduit for transporting the calibration fluid from the cavity to the biosensor chamber, the conduit being in fluid communication with the cavity and the biosensor chamber;
   a compressible air chamber within the cartridge housing, the compressible air chamber being fluidly connected to the biosensor chamber at a point in the one or more than one flow path located between the inlet opening and the biosensor chamber, the compressible air chamber being operable to displace the calibration fluid; and
the system further comprises:
   means for facilitating operation of the compressible air chamber when the one or more than one flow path comprises a plurality of openings.

3. A spectroscopic and biosensor system for analyzing a blood sample taken from a patient, the system comprising:
   a disposable cartridge;
   spectroscopic means for measuring a blood hemoglobin oxygen saturation value; and
   biosensor means for measuring a blood pH value;
      wherein the disposable cartridge comprises:
         a cartridge housing;
         an inlet opening in the cartridge housing for receiving the blood sample;
         one or more than one flow path in the cartridge housing for receiving the blood sample from the inlet opening;
         an optical chamber in the one or more than one flow path, the optical chamber having at least one optical window to facilitate the spectroscopic means for measuring a blood hemoglobin oxygen saturation value;
         a biosensor chamber in the one or more than one flow path, the biosensor chamber comprising a pH biosensor to facilitate the biosensor means for measuring a blood pH value; and
         one of an outlet vent and a compression suction chamber for promoting flow of the blood sample inside the flow path;
      whereby the blood hemoglobin oxygen saturation value and the blood pH value will provide an assessment the patient's oxygenation and acid-base status.

4. The system according to claim 3, wherein
the biosensor means further comprises;
   a cavity within the cartridge housing having a sealed calibration pouch containing a calibration fluid for calibrating the pH biosensor;
   a capillary break disposed between the optical chamber and the biosensor chamber, the capillary break being operable to retain at least one of the fluid sample and a calibration fluid away from the biosensor chamber and the optical chamber, respectively.

5. The system according to claim 3, wherein the spectroscopic means further includes means for reducing average attenuation of electromagnetic radiation due to scattering of electromagnetic radiation by red blood cells in the blood in order to measure the blood hemoglobin oxygen saturation value in the blood absent induced hemolysis.

6. A spectroscopic and biosensor method for analyzing a blood sample taken from a patient, the method comprising:

obtaining a blood sample from the patient;
providing a disposable cartridge comprising:
a cartridge housing;
an inlet opening in the cartridge housing for receiving the blood;
one or more than one flow path to receive the blood from the inlet opening;
an optical chamber in the one or more than one flow path, the optical chamber comprising at least one optical window to facilitate detection of an electromagnetic radiation-based signal derived from the blood;
a biosensor chamber in the one or more than one flow path, the biosensor chamber comprising a pH biosensor;
an electrical output contact in communication with the pH biosensor; and
at least one of an outlet vent and a compression suction chamber to facilitate blood flow inside the one or more than one flow path;
providing a meter comprising:
a meter housing;
a meter source of electromagnetic radiation;
a slot in the meter housing for receiving the disposable cartridge, the slot comprising an electrical input contact; and
one or more than one photodetector;
urging the blood into the one or more than one flow path in order to fill at least the optical chamber;
positioning the optical chamber to receive the meter source of electromagnetic radiation by mating the electrical output contact with the electrical input contact and, at one of
a period prior to urging the blood into the one or more than one flow path and
a period after urging the blood into the one or more than one flow path;
irradiating the blood in the optical chamber with the meter source of electromagnetic radiation and measuring electromagnetic radiation transmitted through or reflected from the blood with the one or more than one photodetector, thereby generating the electromagnetic radiation-based signal;
urging the blood into the biosensor chamber for the blood to make contact with the pH biosensor, if the blood is not yet urged into the biosensor chamber, for generating blood biosensor data; and
processing the electromagnetic radiation-based signal and the blood biosensor data to produce a blood hemoglobin oxygen saturation value and a blood pH value respectively, whereby the blood hemoglobin oxygen saturation value and the blood pH value will provide an assessment of the patient's oxygenation and acid-base status.

7. The method according to claim 6, wherein the cartridge comprises one flow path, wherein the optical chamber is fluidly connected to the inlet opening, and the biosensor chamber is fluidly connected to the inlet opening via the optical chamber.

8. The method according to claim 6, wherein the cartridge further comprises a manifold for splitting the blood into a first flow path comprising an optical chamber and a second flow path comprising a biosensor chamber.

9. The method according to claim 6, further comprising calibrating the pH biosensor prior to urging the blood to fill the optical chamber.

10. The method according to claim 6, further comprising calibrating the pH biosensor prior to urging the blood into the biosensor chamber.

11. The method according to claim 6, further comprising maintaining red blood cells in the blood substantially intact during irradiating the blood absent induced hemolysis.

12. The method according to claim 6, further comprising maintaining the one or more than one flow path restricted to the cartridge housing absent one or more blood fluid connection between the cartridge and the meter.

13. The method according to claim 9, wherein the cartridge further comprises a compressible air chamber fluidly connected to the biosensor chamber, and the method further comprises:
closing at least one opening in the one or more than one flow path;
compressing the compressible air chamber; and
displacing the calibration fluid from the calibration chamber with the blood, using air from the air chamber.

14. The method according to claim 10, wherein the cartridge further comprises a compressible air chamber fluidly connected to the biosensor chamber, and the method further comprises:
closing at least one opening in the one or more than one flow path;
compressing the compressible air chamber; and
displacing the calibration fluid from the calibration chamber with the blood, using air from the air chamber.

* * * * *